United States Patent
Schoenfisch et al.

(10) Patent No.: US 12,173,090 B2
(45) Date of Patent: Dec. 24, 2024

(54) NITRIC OXIDE-RELEASING ANTIBACTERIAL POLYMERS AND SCAFFOLDS FABRICATED THEREFROM AND METHODS PERTAINING THERETO

(71) Applicant: THE UNIVERSITY OF NORTH CAROLINA AT CHAPEL HILL, Chapel Hill, NC (US)

(72) Inventors: Mark H. Schoenfisch, Chapel Hill, NC (US); Mona Jasmine R. Ahonen, Chapel Hill, NC (US); Lei Yang, Carrboro, NC (US); Haibao Jin, Carrboro, NC (US); Evan Scott Feura, Carrboro, NC (US); Sara Elizabeth Maloney, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 28 days.

(21) Appl. No.: 17/806,323

(22) Filed: Jun. 10, 2022

(65) Prior Publication Data
US 2023/0174679 A1   Jun. 8, 2023

Related U.S. Application Data

(62) Division of application No. 16/725,566, filed on Dec. 23, 2019, now Pat. No. 11,421,044.

(60) Provisional application No. 62/786,098, filed on Dec. 28, 2018.

(51) Int. Cl.
| | | |
|---|---|---|
| C08B 37/08 | (2006.01) | |
| A61K 9/06 | (2006.01) | |
| A61K 31/717 | (2006.01) | |
| A61K 31/726 | (2006.01) | |
| A61K 31/728 | (2006.01) | |
| A61L 27/34 | (2006.01) | |
| C08B 15/04 | (2006.01) | |
| C08B 37/00 | (2006.01) | |

(52) U.S. Cl.
CPC .............. *C08B 15/04* (2013.01); *A61K 9/06* (2013.01); *A61K 31/717* (2013.01); *A61K 31/726* (2013.01); *A61K 31/728* (2013.01); *A61L 27/34* (2013.01); *C08B 37/0063* (2013.01); *C08B 37/0072* (2013.01); *A61L 2300/404* (2013.01)

(58) Field of Classification Search
CPC .............. C08B 11/10–12; C08B 31/12; A61K 31/717–718; A61K 47/61; A61L 27/20
See application file for complete search history.

(56) References Cited

U.S. PATENT DOCUMENTS

| | | | |
|---|---|---|---|
| 4,169,079 A | 9/1979 | Tabushi et al. | |
| 5,234,933 A | 8/1993 | Marnett et al. | |
| 5,326,902 A | 7/1994 | Seipp et al. | |
| 5,525,357 A | 6/1996 | Keefer et al. | |
| 5,574,027 A | 11/1996 | Bernstein | |
| 5,632,981 A | 5/1997 | Saavedra et al. | |
| 5,650,442 A | 7/1997 | Mitchell et al. | |
| 5,650,447 A | 7/1997 | Keefer et al. | |
| 5,691,423 A * | 11/1997 | Smith ................. | A61P 9/10 424/78.17 |
| 5,714,511 A | 2/1998 | Saavedra et al. | |
| 5,814,666 A | 9/1998 | Green et al. | |
| 5,840,759 A | 11/1998 | Mitchell et al. | |
| 5,910,316 A | 6/1999 | Keefer et al. | |
| 6,110,453 A | 8/2000 | Keefer et al. | |
| 6,121,441 A | 9/2000 | Simensen et al. | |
| 6,180,082 B1 | 1/2001 | Woltering et al. | |
| 6,200,558 B1 | 3/2001 | Saavedra et al. | |
| 6,261,594 B1 | 7/2001 | Smith et al. | |
| 6,451,337 B1 | 9/2002 | Smith et al. | |
| 6,911,433 B2 | 6/2005 | Saavedra et al. | |
| 7,553,656 B2 | 6/2009 | Gimmestad et al. | |
| 7,928,079 B2 | 4/2011 | Hrabie et al. | |
| 8,158,580 B2 | 4/2012 | Judice et al. | |
| 8,518,362 B2 * | 8/2013 | Smith ................. | C01B 21/24 423/405 |
| 8,603,454 B2 | 12/2013 | Cheng et al. | |
| 8,815,831 B2 | 8/2014 | Onsoyen et al. | |
| 8,841,279 B2 | 9/2014 | Taylor et al. | |
| 8,987,215 B2 | 3/2015 | Taylor et al. | |
| 9,238,038 B2 | 1/2016 | Schoenfisch et al. | |
| 9,539,233 B2 | 1/2017 | Ohtake et al. | |
| 9,850,322 B2 | 12/2017 | Schoenfisch et al. | |
| 10,759,877 B2 | 9/2020 | Schoenfisch et al. | |

(Continued)

FOREIGN PATENT DOCUMENTS

| | | |
|---|---|---|
| CA | 2205564 C | 7/2006 |
| CN | 1868544 | 11/2006 |

(Continued)

OTHER PUBLICATIONS

Taubner, T. et al "Preparation of amidated derivatives of carboxymethylcellulose" Int. J. Biol. Macromol., vol. 72, pp. 11-18. (Year: 2015).*

Kastner, U. et al "Structure and solution properties of sodium carboxymethyl cellulose" Colloids and Surfaces, vol. 123-124, pp. 307-328. (Year: 1997).*

Reuben, J. et al "Analysis of the carbon-13 NMR spectrum . . . " Carbohyd. Res., vo 115, pp. 1-13. (Year: 1983).*

Ahonen et al., "Nitric oxide-releasing alginate as a biodegradable antibacterial scaffold," 253rd National Metting of the American Chemical Society (ACS) on Advanced Materials, Technologies, Systems, and Processes; San Francisco, CA, Apr. 2-6, 2017 - Abstracts of Papers, p. 600, (2017).

Ahonen et al., "Nitric oxide-releasing alginates as mucolytic agents," ACS Biomater. Sci. Eng., 5:3409-3418, (2019).

(Continued)

*Primary Examiner* — Leigh C Maier
(74) *Attorney, Agent, or Firm* — Alston & Bird LLP

(57) ABSTRACT

Several embodiments of NO releasing structures are disclosed. In some embodiments, the structures are covalently modified to store and release nitric oxide. Some embodiments pertain to methods of making and use of these structures. The covalently modified polymer structures may be tailored to release nitric oxide in a controlled manner and are useful for treatment of various medical conditions.

20 Claims, 31 Drawing Sheets

(56) References Cited

U.S. PATENT DOCUMENTS

| | | |
|---|---|---|
| 11,026,965 B2 | 6/2021 | Schoenfisch et al. |
| 11,072,668 B2 | 7/2021 | Schoenfisch et al. |
| 2001/0000039 A1 | 3/2001 | Toone et al. |
| 2002/0122857 A1 | 9/2002 | Asai et al. |
| 2003/0078365 A1 | 4/2003 | Stamler et al. |
| 2003/0093143 A1 | 5/2003 | Zhao et al. |
| 2004/0038947 A1 | 2/2004 | Wink et al. |
| 2005/0009789 A1 | 1/2005 | Wink et al. |
| 2005/0085413 A1 | 4/2005 | Jin et al. |
| 2005/0228184 A1 | 10/2005 | Haj-Yehia |
| 2005/0265956 A1 | 12/2005 | Liu et al. |
| 2006/0199785 A1 | 9/2006 | Fahmi et al. |
| 2007/0243131 A1 | 10/2007 | Chen et al. |
| 2008/0305004 A1 | 12/2008 | Anderson et al. |
| 2009/0214618 A1 | 8/2009 | Schoenfisch et al. |
| 2009/0222088 A1 | 9/2009 | Chen et al. |
| 2009/0232863 A1 | 9/2009 | Cheng et al. |
| 2010/0197631 A1 | 8/2010 | Reiner et al. |
| 2010/0262238 A1 | 10/2010 | Chen et al. |
| 2010/0305062 A1 | 12/2010 | Onsoyen et al. |
| 2010/0305489 A1 | 12/2010 | Liu et al. |
| 2011/0002999 A1 | 1/2011 | Chen et al. |
| 2011/0150999 A1 | 6/2011 | Chu et al. |
| 2011/0218139 A1 | 9/2011 | Robinson et al. |
| 2012/0034169 A1 | 2/2012 | Schoenfisch et al. |
| 2012/0107229 A1 | 5/2012 | Huang et al. |
| 2013/0096078 A1 | 4/2013 | Yoon et al. |
| 2013/0196951 A1 | 8/2013 | Schoenfisch et al. |
| 2013/0337033 A1 | 12/2013 | Balkus, Jr. et al. |
| 2014/0256658 A1 | 9/2014 | Sinha et al. |
| 2015/0126467 A1 | 5/2015 | Onsøyen et al. |
| 2015/0225488 A1 | 8/2015 | Schoenfisch et al. |
| 2016/0185891 A1 | 6/2016 | Chambers et al. |
| 2016/0331777 A1 | 11/2016 | Dessen et al. |
| 2016/0346313 A1 | 12/2016 | Nordgard et al. |
| 2016/0361342 A1 | 12/2016 | Hansson et al. |
| 2017/0333456 A1 | 11/2017 | Miranda et al. |
| 2018/0055873 A1 | 3/2018 | Dessen et al. |
| 2019/0197631 A1 | 6/2019 | Schneider |
| 2019/0225747 A1 | 7/2019 | Schoenfisch et al. |
| 2019/0322770 A1 | 10/2019 | Schoenfisch et al. |
| 2019/0343869 A1 | 11/2019 | Schoenfisch et al. |
| 2020/0021657 A1 | 1/2020 | Brinkmann et al. |
| 2020/0030362 A1 | 1/2020 | Schoenfisch et al. |
| 2020/0216571 A1 | 7/2020 | Schoenfisch et al. |
| 2020/0332061 A1 | 10/2020 | Schoenfisch et al. |
| 2021/0346424 A1 | 11/2021 | Schoenfisch et al. |
| 2021/0347918 A1 | 11/2021 | Schoenfisch et al. |

FOREIGN PATENT DOCUMENTS

| | | |
|---|---|---|
| CN | 101049513 A | 10/2007 |
| CN | 102083862 A | 6/2011 |
| CN | 106046382 A | 10/2016 |
| EP | 0726768 B1 | 5/2000 |
| EP | 2547660 B1 | 1/2015 |
| EP | 3185853 A1 | 7/2017 |
| IN | 2010 | 11/2010 |
| JP | 2001-524991 A | 12/2001 |
| JP | 2002-518557 A | 6/2002 |
| JP | 2005047979 A | 2/2005 |
| JP | 4285775 B2 | 6/2009 |
| NO | 20050480 L | 4/2005 |
| WO | WO 93/25521 A1 | 12/1993 |
| WO | WO 1996/015797 A1 | 5/1996 |
| WO | WO 1996/032136 | 10/1996 |
| WO | WO 1998/005689 A1 | 2/1998 |
| WO | WO 1998/013358 A1 | 4/1998 |
| WO | WO 00/30658 A1 | 6/2000 |
| WO | WO 2007/085254 A1 | 8/2007 |
| WO | WO 2009/049208 A1 | 4/2009 |
| WO | WO 2010/037179 A1 | 4/2010 |
| WO | WO 2010/096320 A2 | 8/2010 |
| WO | WO 2010/139957 A1 | 12/2010 |
| WO | WO 2010/139958 A1 | 12/2010 |
| WO | WO 2010/139959 A2 | 12/2010 |
| WO | WO 2011/003172 A1 | 1/2011 |
| WO | WO 2012/046994 A2 | 4/2012 |
| WO | WO 2012/116177 A2 | 8/2012 |
| WO | WO 2013/029009 A1 | 2/2013 |
| WO | WO 2014/028847 A1 | 2/2014 |
| WO | WO 2017/060388 A1 | 4/2017 |
| WO | WO 2018/067838 A1 | 4/2018 |
| WO | WO 2018/127819 A1 | 7/2018 |
| WO | WO 2018/178902 A1 | 10/2018 |
| WO | WO 2019/099525 A1 | 5/2019 |
| WO | WO 2019/173539 A1 | 9/2019 |
| WO | WO 2020/139857 A1 | 7/2020 |

OTHER PUBLICATIONS

Allaker, R.P., "The use of Nanoparticles to Control Oral Biofilm formation," J. Dent. Res., 89(11):1175-1186, (2010).

Alnaief et al., "Preparation of biodegradable nanoporous microspherical aerogel based on alginate," Carbohydrate Polymers, 84(3):1011-1018, (2011).

Arulsamy, N et al. "Multiplicity Control in the Polygeminal Diazeniumdiolation of Active Hydrogen Bearing Carbons: Chemistry of a New Type of Trianionic Molecular Propeller," S. J. Am. Chem. Soc., 123:10860-10869, (2001).

Backlund et al., "Antibacterial Efficacy of Exogenous Nitric Oxide on Periodontal Pathogens," J. Dent. Res., 93(11): 1089-1094, (2014).

Backlund et al., "Anti-biofilm action of nitric oxide-releasing alkyl-modified poly(amidoamine) dendrimers against Streptococcus mutans," Acta Biomaterialia, 29:198-205, (2016).

Backlund et al., "Kinetic-dependent Killing of Oral Pathogens with Nitric Oxide," J. Dent. Res., 94(8): 1092-1098, (2015).

Barraud et al., "Nitric Oxide: A Key Mediator of Biofilm Dispersal with Applications in Infectious Diseases," Curr. Pharm. Des., 21(1):31-42, (2015).

Barraud et al., "Involvement of Nitric Oxide in Biofilm Dispersal of Pseudomonas aeruginosa," Journal of Bacteriology, 188(21): 7344-7353, (2006).

Beck et al., "Systemic Effects of Periodontitis: Epidemiology of Periodontal Disease and Cardiovascular Disease," J. Periodontol., 76(11)(Suppl.):2089-2100, (2005).

Belley, A et al., "Assessment by time-kill methodology of the synergistic effects of oritavancin in combination with other antimicrobial agents against Staphylococcus aureus," Antimicrob. Agents Chemother., 52:3820-3822, (2008).

Benkovics et al., "A multifunctional B-cyclodextrin-conjugate photodelivering nitric oxide with fluorescence reporting," International Journal of Pharmaceutics, 531: 614-620 (2017).

Bernkop-Schnurch et al., "Improvement in the mucoadhesive properties of alginate by the covalent attachment of cysteine," Journal of Controlled Release, 71(3):277-285, (2001).

Besinis et al., "Review of Nanomaterials in Dentistry: Interactions with the Oral Microenvironment, Clinical Applications, Hazards, and Benefits," ACS Nano, 9(3):2255-2289, (2015).

Beveridge, Terry J., "Structures of Gram-Negative Cell Walls and Their Derived Membrane Vesicles," Journal of Bacteriology, 181(16):4725-4733, (1999).

Bhardwaj, Atul, et al., "A diazen-1-ium-1, 2-diolate analog of 7-azabenzobicyclo [2.2. 1] heptane: Synthesis, nitric oxide and nitroxyl release, in vitro hemodynamic, and anti- hypertensive studies," Biioorganic & Medicinal Chemistry Letters, 23(9):2769-2774, (2013).

Bjarnsholt et al., "Why chronic wounds will not heal: a novel hypothesis," Wound Rep. Reg., 16:2-10, (2008).

BOAS and HEEGAARD, "Dendrimers in drug research," Chem. Soc. Rev., 33(1):43-63, (2004).

Bogdan, Christian, "Nitric oxide and the immune response," Nat. Immunol., 2(10): 907- 916, (2001).

Bollenbach, T., "Antimicrobial interactions: mechanisms and implications for drug discovery and resistance evolution," Curr. Opin. Microbiol., 27:1-9, (2015).

Breed and Dotterrer, "The number of colonies allowable on satisfactory agar plates," J. Bacteriol. 1(3):321-331, (1916).

(56) References Cited

OTHER PUBLICATIONS

Calabretta et al., "Antibacterial activities of poly (amidoamine) dendrimers terminated with amino and poly (ethylene glycol) groups," Biomacromolecules, 8(6):1807-1811, (2007).
Caleffi-Ferracioli et al., "Fast detection of drug interaction in *Mycobacterium tuberculosis* by a checkerboard resazurin method," Tuberculosis, 93:660-663, (2013).
Caminade et al., "Dendrimers and hyperbranched polymers," Chem. Soc. Rev, 44(12):3870-3873, (2015).
Cao et al., "Synthesis and striking fluorescence properties of hyperbranched poly (amido amine)," J. Macromol. Sci. Pure Appl. Chem., 44(4):417-424, (2007).
Caraher, E. M. et al., "The effect of recombinant human lactoferrin on growth and the antibiotic susceptibility of the cystic fibrosis pathogen Burkholderia cepacia complex when cultured planktonically or as biofilms," J. Antimicrob. Chemother., 60:546-554, (2007).
Carlmark et al., "New methodologies in the construction of dendritic materials," Chem. Soc. Rev., 38(2):352-362, (2009).
Carlmark, A. et al., "Dendritic Architechtures Based on bis-MPA: Functional Polymeric Scaffolds for Application-Driven Research," Chem. Soc. Rev., 42:5858-79, (2013).
Carpenter et al., "Dual action antimicrobials: nitric oxide release from quaternary ammonium-functionalized silica nanoparticles," Biomacromolecules, 13(10):3334-3342, (2012).
Carpenter et al., "Nitric oxide release: Part II. Therapeutic applications," Chem. Soc. Rev., 41(10):3742-3752, (2012).
Centers for Disease Control, Antibiotic Resistance Threats in the United States, (2013).
Chakrapani, Harinath, et al., "Nitric oxide prodrugs: diazeniumdiolate anions of hindered secondary amines," Organic Letters, 9(22): 4551-4554, (2007).
Charbonneau et al., "Reduced chlorhexidine tooth stain coverage by sequential administration of monoperoxyphthalic acid in the beagle dog," J. Dent. Res., 76(9):1596-1601, (1997).
Chen et al., "Cytotoxicity, hemolysis, and acute in vivo toxicity of dendrimers based on melamine, candidate vehicles for drug delivery," J. Am. Chem. Soc., 126(32):10044-10048, (2004).
Chen et al., "Cariogenic Actinomyces Identified with a β-Glucosidase-Dependent Green Color Reaction to Gardenia jasminoides Extract," Journal of Clinical Microbology, 39(8):3009-3012, (2001).
Chen et al., "Hyperbranched glycoconjugated polymer from natural small molecule kanamycin as a safe and efficient gene vector," Polym. Chem., 2:2674-2682, (2011).
Chen et al., "Hyperbranched polymers from A2 +B 3 strategy: recent advances in description and control of fine topology," Polym. Chem., 7(22):3643-3663, (2016).
Chen et al., "Multifunctional Hyperbranched Glycoconjugated Polymers Based on Natural Aminoglycosides," Bioconjugate Chemistry, 23(6): 1189-1199, (2012).
Chen et al., "Selective deprotection of the Cbz amine protecting group for the facile synthesis of kanamycin A dimers linked at N-3" position," Tetrahedron, 65(31)5922-5927, (2009).
Cheng et al., "Michael Addition Polymerization of Trifunctional Amine and Acrylic Monomer: A Versatile Platform for Development of Biomaterials," Biomacromolecules, 17(10):3115-3126, (2016).
Ciacci, N., et al., "In vitro Synergism of Colistin and N-acetylcysteine against Stenotrophomonas maltophilia," Antibiotics, 8:101, (2019).
Ciofu, O. & Tolker-Nielsen, T., "Tolerance and Resistance of Pseudomonas aeruginosa Biofilms to Antimicrobial Agents—How P. aeruginosa Can Escape Antibiotics, " Front. Microbiol., 10:913, (2019).
Cleland, W.W., "Diothiothreitol, A New Protective Reagent for SH Groups," Biochemical., 3(4):480-482, (1964).
Compound Summary, "PubChem Compound Summary for CID 65430: Gallium citrate ga-67," National Library of Medicine: National Center for Biotechnology Information, (Last accessed Aug. 7, 2020), https://pubchem.ncbi.nlm.nih.gov/compound/Gallium-citrate-ga-67.
Compound Summary, "Gallium citrate Ga-67," Drugbank, (Last accessed Aug. 6, 2020), https://www.drugbank.ca/drugs/DB06784.

Compound Summary, "PubChem Compound Summary for CID 61635, Gallium nitrate," National Library of Medicine: National Center for Biotechnology Information, (Last accessed Aug. 7, 2020) https://pubchem.ncbi.nlm.nih.gov/compound/61635.
Coneski and Schoenfisch, "Nitric oxide release: part III. Measurement and reporting," Chem. Soc. Rev., 41(10):3753-3758, (2012).
Coneski, "Design and Synthesis of Nitric Oxide Releasing Polymers for Biomedical Applications", pp. 122-127, (2010). [Retrieved from the Internet: URL:https://cdr.lib.unc.edu/indexablecontent/uuid:d84bce49-d4dd-4026-96a5-3ea9e82dee9c [retrieved on Oct. 9, 2015]].
Coneski, P.N. and Schoenfisch, M.H., "Synthesis of Nitric Oxide-Releasing Polyurethanes with S-Nitrosothiol-Containing Hard and Soft Segments," Polym. Chem., 2(4):906-913, (2011).
Coneski, P.N. et al., "Degradable Nitric Oxide-Releasing Biomaterials via Post-Polymerization Functionalization of Cross-Linked Polyesters," Biomacromolecules, 11(11):3208-3215, (2010).
Cooke et al., "Nitric Oxide and Angiogenesis," Circulation, 105:2133-2135, (2002).
Cooke, John P., "NO and Angiogenesis," Atherosclerosis Suppl., 4(4):53-60, (2003).
Cullen, L. & McClean, S., "Bacterial adaptation during chronic respiratory infections," Pathogens, 4:66-89, (2015).
Cutrone et al., "Mannoside and 1,2-mannobioside β-cyclodextrin-scaffolded NO-photodonors for targeting antibiotic resistant bacteria", Carbohydr. Polym, 199: 649-660, (2018).
Da Silva et al., "Antimicrobial peptide control of pathogenic microorganisms of the oral cavity: A review of the literature," Peptides, 36(2):315-321, (2012).
Damodaran, V.B. and Reynolds, M.M., "Biodegradable S-Nitrosothiol Tethered Multiblock Polymer for Nitric Oxide Delivery," J. Mater. Chem., 21:5870-5872, (2011).
Davies et al., "Evolutionary diversification of Pseudomonas aeruginosa in an artificial sputum model," BMC Microbiol., 17:3, (2017).
Davies et al., "Chemistry of the diazeniumdiolates. 2. Kinetics and Mechanism of Dissociation to Nitric Oxide in Aqueous Solution," JACS, 123(23):5473-5481, (2001).
Deng et al., "pH and cation-responsive supramolecular gels formed by cyclodextrin amines in DMSO," Soft Matter, 6:1884-1887, (2010).
Deupree, S. M. & Schoenfisch, M. H., "Morphological analysis of the antimicrobial action of nitric oxide on Gram-negative pathogens using atomic force microscopy," Acta Biomater., 5:1405-1415, (2009).
Draget et al., "Chemical, physical and biological properties of alginates and their biomedical implications," Food Hydrocolloids, 25(2):251-256, (2011).
Drug Development Pipeline Status, "Inhaled Gallium: Phase One", Cystic Fibrosis Foundation, (Last accessed Aug. 13, 2020), https://www.cff.org/Trials/Pipeline/details/10146/Inhaled-Gallium.
Duncan and Izzo, "Dendrimer biocompatibility and toxicity," Adv. Drug Deliv. Rev., 57(14):2215-2237, (2005).
Duong et al., "Functional gold nanoparticles for the storage and controlled release of nitric oxide: applications in biofilm dispersal and intracellular delivery," J. Mater. Chem. B-2, 2(31):5003-5011, (2014).
Duong et al., "Nanoparticle (Star Polymer) Delivery of Nitric Oxide Effectively Negates Pseudomonas aeruginosa Biofilm Formation," Biomacromolecules, 15(7):2583-2589, (2014).
Elion et al., "Antagonists of Nucleic Acid Derivatives: VIII. Synergism in combinations of biochemically related antimetabolites," J. Biol. Chem., 208:477-488, (1954).
Falcone et al., "Rheological and cohesive properties of hyaluronic acid," J. Biomed. Mater. Res., Part A, 76A(4):721-728, (2005).
Fang, Ferric C., "Antimicrobial reactive oxygen and nitrogen species: concepts and controversies," Nat. Rev. Micro., 2(10):820-832, (2004).
Feliu, N. et al., "Stability and Biocompatibility of a Library of Polyester Dendrimers in Comparison to Polyamidoamine Dendrimers," Biomaterials, 33(7):1970-1981, (2012).
Fernandez-Barat, L. et al., "Phenotypic shift in Pseudomonas aeruginosa populations from cystic fibrosis lungs after 2-week antipseudomonal treatment," J. Cyst. Fibros., 16:222-229, (2017).

(56) References Cited

OTHER PUBLICATIONS

Friedman et al., "The negative impact of antibiotic resistance," Clin. Microbiol. Infect., 22:416-422, (2016).
Frost, M.C. and Meyerhoff, M.E., "Synthesis, Characterization, and Controlled Nitric Oxide Release from S-Nitrosothiol-Derivatized Fumed Silica Polyme Filler Particles," J. Biomed. Mater. Res. Part A., 72A(4):409-419, (2005).
Fu, et al., "Preparation and reversible photo-crosslinking/photocleavage behavior o 4-methylcoumarin functionalized hyperbranched polyester," Polymer, 49(23): 4981-4988, (2008).
Gabor, G. and Vincze, A., "Determination of Thiols in Non-Aqueous Solutions," Anal. Chim. Acta., 92(2):429-431, (1977).
Gao and Koo, "Do catalytic nanoparticles offer an improved therapeutic strategy to combat dental biofilms?," Nanomed. Nanotech. Biol. Med., 12(4):275-279, (2017).
Gao and Yan, "Hyperbranched polymers: from synthesis to applications," Prog. Polym. Sci., 29(3):183-275, (2004).
Gao, Q, et al., "Synthesis and Characterization of Chitosan-Based Diazeniumdiolates [Abstract]," Polymer Materials Science and Engineering, 24(12):415-421, (2008).
Ghosh, S. & Lapara, T. M., "The effects of subtherapeutic antibiotic use in farm animals on the proliferation and persistence of antibiotic resistance among soil bacteria," ISME J., 1:191-203, (2007).
Gibney et al., "Poly(ethylene imine)s as antimicrobial agents with selective activity," Macromol. Biosci., 12(9):1279-1289, (2012).
Gombotz et al., "Protein release from alginate matrices," Advanced Drug Delivery Reviews, 31(3):267-285, (1998).
Grabowski et al., "Toxicity of surface-modified PLGA nanoparticles toward lung alveolar epithelial cells," International Journal of Pharmaceutics, 454:686-694, (2013).
Haggie, P., and Lueck, J. (Eds), "Agenda for Cystic Fibrosis Foundation Research Conference," Cystic Fibrosis Foundation, (2019), https://www.cff.org/Research/Researcher-Resources/Cystic-Fibrosis-Foundation-Research-Conference/.
Hall, J. R. et al., "Mode of nitric oxide delivery affects antibacterial action," ACS Biomater. Sci. Eng., acsbiomaterials.9b01384 (2019).
Hall-Stoodley et al., "Bacterial Biofilms: from the Natural Environment to Infectious Diseases," Nat. Rev. Micro., 2:95-108, (2004).
Harrison et al., "Development of an ex vivo porcine lung model for studying growth Virulence, And signaling of pseudomonas aeruginosa," Infect. Immun., 82:3312-3323, (2014).
Helander, I. M. & Mattila-Sandholm, T., "Fluorometric assessment of Gram-negative bacterial permeabilization," J. Appl. Microbiol., 88:213-219, (2000).
Hetrick and Schoenfisch, "Analytical chemistry of nitric oxide," Annu. Rev. Anal. Chem., 2:409-433, (2009).
Hetrick et al., "Anti-biofilm efficacy of nitric oxide-releasing silica nanoparticles," Biomaterials, 30:2782-2789, (2009).
Hetrick et al., "Bactericidal Efficacy of Nitric-Oxide Releasing Silica Nanoparticles," ACS Nano, 2(2):235-246, (2008).
Hopkins, Sean, "Development of High Capacity Hyperbranched Nitric Oxide Donors for Controlling Subcutaneous Inflammation," Access Dissertation, Michigan Technological University, (2015).
Hopkins, Sean, "Development of high capacity hyperbranched nitric oxide donors for controlling subcutaneous inflammation," Open Access Dissertation, Michigan Technological University, 154 pages, (2015).
Hossain et al., "Discovery of Two Bacterial Nitric Oxide-Responsive Proteins and Their Roles in Bacterial Biofilm Regulation," Acc. Chem. Res., 50(7):1633-1639, (2017).
Howlin, R. P., et al., "Low-Dose Nitric Oxide as Targeted Anti-biofilm Adjunctive Therapy to Treat Chronic Pseudomonas aeruginosa Infection in Cystic Fibrosis," Mol. Ther., 25:2104-2116, (2017).
Hrabie, Joseph A., et al., "New nitric oxide-releasing zwitterions derived from polyamines," The Journal of Organic Chemistry, 58(6):1472-1476, (1993).
Hu et al., "A smart aminoglycoside hydrogel with tunable gel degradation, on-demand drug release, and high antibacterial activity," Journal of Controlled Release, 247:145-152, (2017).
Huang et al., "Nitric oxide-loaded echogenic liposomes for nitric oxide delivery and inhibition of intimal hyperplasia," J. Am. Coll. Cardiol., 54(7):652-659, (2009).
Huang et al., "Reduction-responsive multifunctional hyperbranched polyaminoglycosides with excellent antibacterial activity, biocompatibility and gene transfection capability," Biomaterials, 106:134-143, (2016).
Hussain et al., "Glucocorticoids can affect Pseudomonas aeruginosa (ATCC 27853) internalization and intracellular calcium concentration in cystic fibrosis bronchial epithelial cells," Experimental Lung Research, 41(7):383-392, (2015).
Imfeld, T. "Chewing gum—facts and fiction: a review of gum-chewing and oral health," Crit. Rev. Oral. Biol. Med., 10(3):405-419, (1999).
Jin et al., "Nitric Oxide-Releasing Cyclodextrins," Journal of the American Chemical Society, 140: 14178-14184 (2018).
Jin et al., "Biocompatible or biodegradable hyperbranched polymers: from self-assembly to cytomimetic applications," Chem. Soc. Rev., 41(18):5986-5997, (2012).
Jones et al., "Antimicrobial properties of nitric oxide and its application in antimicrobial formulations and medical devices," Appl. Microbiol. Biotechnol., 88(2):401-407, (2010).
Jones, C.G., "Chlorhexidine: is it still the gold standard?" Periodontology 2000, 15:55-62, (1997).
Kailasan et al., "Synthesis and characterization of thermoresponsive polyamidoamine-polyethylene glycol-poly (d, l-lactide) core-shell nanoparticles," Acta Biomater. 6(3):1131-1139, (2010).
Kaneko et al., "The transition metal gallium disrupts Pseudomonas aeruginosa iron metabolism and has antimicrobial and antibiofilm activity," The Journal of Clinical Investigations, 117(4):877-888, (2007).
Karatasos, K., "Self-Association and Complexation of the Anti-Cancer Drug Doxorubicin with PEGylated Hyperbranched Polyesters in an Aqueous Environment," J. Phys. Chem. B., 117(8):2564-2575, (2013).
Kassebaum et al., "Global Burden of Untreated Caries: A Systematic Review and Metaregression," Journal of Dental Research, 94(5):650-658, (2015).
Keefer et al., "Chemistry of the Diazeniumdiolates I. Structural and Spectral Characteristics of the [N(O)NO]—Functional Group," Nitric Oxide, 5(4):377-394, (2001).
Keefer et al., "'NONOates' (1-Substituted Diazen-1-ium-1,2-diolates) as Nitric Oxide Donors: Convenient Nitric Oxide Dosage Forms," Methods in Enzymology, 268:281-293, (1996).
Keefer, Larry K., "Fifty Years of Diazeniumdiolate Research. From Laboratory Curiosity to Broad-Spectrum Biomedical Advances," ACS Chemical Biology, 6(11):1147-1155, (2011).
Keefer, Larry K., "Nitric Oxide (NO)- and Nitroxyl (HNO)-Generating Diazeniumdiolates (NONOates): Emerging Commercial Opportunities," Current Topics in Medicinal Chemistry, 5(7):625-636, (2005).
Khalil et al., "Synergy between Polyethylenimine and Different Families of Antibiotics against a Resistant Clinical Isolate of Pseudomonas aeruginosa," Antimicrob. Agents Chemother., 52:1635-1641, (2008).
Khan et al., "Overcoming Drug Resistance with Alginate Oligosaccharides Able To Potentiate the Action of Selected Antibiotics," Antimicrobial Agents and Chemotherapy, 56(10):5134-5141, (2012).
Kim et al., "NONOates—polyethylenimine hydrogel for controlled nitric oxide release and cell proliferation modulation," Bioconjugate Chem., 22(6):1031-1038, (2011).
Knop et al., "Poly(ethylene glycol) in drug delivery: pros and cons as well as potential alternatives," Angew. Chem. Int. Ed., 49(36):6288-6308, (2010).
Konter, Joerg, et al., "Synthesis of Diazen-1-ium-1, 2-diolates Monitored by the "NOtizer" Apparatus: Relationship between Formation Rates, Molecular Structure and the Release of Nitric Oxide," European Journal of Organic Chemistry, 2007(4): 616-624, (2007).
Kovach, K. et al., "Evolutionary adaptations of biofilms infecting cystic fibrosis lungs promote mechanical toughness by adjusting polysaccharide production," npj Biofilms Microbiomes, 3, (2017).
Kurniasih et al., "Dendritic nanocarriers based on hyperbranched polymers," Chem. Soc. Rev., 44(12):4145-4164, (2015).

(56) References Cited

OTHER PUBLICATIONS

Labena et al., "One-pot synthesize of dendritic hyperbranched PAMAM and assessment as a broad spectrum antimicrobial agent and anti-biofilm," Mater. Sci. Eng. C Mater. Biol. Appl., 58:1150-1159, (2016).
Lee et al., "Alginate: properties and biomedical applications," Prog. Polym. Sci., 37(1):106-126, (2012).
Lenoir et al., "Polyolefin matrixes with permanent antibacterial activity: preparation, antibacterial activity, and action mode of the active species," Biomacromolecules, 7(8):2291-2296, (2006).
Liakos et al., "All-natural composite wound dressing films of essential oils encapsulated in sodium alginate with antimicrobial properties," International Journal of Pharmaceutics, 463(2):137-145, (2014).
Liu et al., "Hollow double-layered polymer microspheres with pH and thermo-responsive properties as nitric oxide-releasing reservoirs," Polym. Chem., 6(17):3305-3314, (2015).
Liu et al., "Synergistic supramolecular encapsulation of amphiphilic hyperbranched polymer to dyes," Macromolecules, 39(23):8102-8111, (2006).
Liu, T. et al., "Hollow Polymer Nanoparticles with S-Nitrosothiols as Scaffolds for Nitric Oxide Release," J. Colloid Interface Sci., 459:115-122, (2015).
Loesche et al., "Role of *Streptococcus mutans* in Human Dental Decay," Microbiological Reviews, 50(4):353-380, (1986).
Lowe et al., "Storage and delivery of nitric oxide via diazeniumdiolated metal organic framework," Micropor. Mesopor. Mat., 181:17-22, (2013).
Lu et al., "Nitric oxide-releasing amphiphilic poly(amidoamine) (PAMAM) dendrimers as antibacterial agents," Biomacromolecules, 14(10):3589-3598, (2013).
Lu et al., "Nitric oxide-releasing chitosan oligosaccharides as antibacterial agents," Biomaterials, 35(5):1716-1724, (2014).
Lu et al., "Structurally Diverse Nitric Oxide-Releasing Poly(propylene imine) Dendrimers," Chem. Mater., 23(18):4227-4233, (2011).
Lu, Y. et al., "Shape- and Nitric Oxide Flux-Dependent Bactericidal Activity of Nitric Oxide-Releasing Silica Nanorods," Small., 9(12):2189-2198, (2013).
Lu, Y. et al., "S-Nitrosothiol-Modified Nitric Oxide-Releasing Chitosan Oligosacccarides as Antibacterial Agents," Acta Biomater., 12:62-69, (2015).
Luo et al., "Nitric oxide: a newly discovered function on wound healing," Acta Pharmacol. Sin., 26(3):259-264, (2005).
Luo et al., "Poly (ethylene glycol)-conjugated PAMAM dendrimer for biocompatible, high-efficiency DNA delivery," Macromolecules, 35(9):356-3462, (2002).
Lutzke, A. et al., "Nitric Oxide-Releasing S-Nitrosated Derivatives of chitin and Chitosan for Biomedical Applications," J. Mater. Chem. B., 2:7449-7458, (2014).
Lutzke, et al., "Nitric oxide release from a biodegradable cysteine-based polyphosphazene," Journal of Materials Chemistry B, 4(11): 1987-1988, (2016).
Machelart et al., "Intrinsic Antibacterial Activity of Nanoparticles Made of β-Cyclodextrins Potentiates Their Effect as Drug Nanocarriers against Tuberculosis", ACS Nano, 13: 3992-4007, (2019).
Macmicking et al., "Nitric oxide and macrophage function," Annu. Rev. Immunol, 15:323-350, (1997).
Madison, C.J., et al., "Gallium and Nitrite Have Synergistic Antimicrobial Activity," Cystic Fibrosis Conference: Scientific Session VIII: Novel Approaches for Treating Difficult Infections, Abstract, Jun. 26, 2019.
Malmström, E. et al., "Hyperbranched Aliphatic Polyesters," Macromolecules, 28(5):1698-1703, (1995).
Maragos, Chris M., et al., "Complexes of. NO with nucleophiles as agents for the controlled biological release of nitric oxide. Vasorelaxant effects," Journal of Medicinal Chemistry, 34(11):3242-3247, (1991).
Martinez, J. L. & Baquero, F., "Mutation Frequencies and Antibiotic Resistance," Antimicrob. Agents Chemother., 44:1771-1777, (2000).

Matai et al., "Chemically Cross-Linked Hybrid Nanogels of Alginate and PAMAM Dendrimers as Efficient Anticancer Drug Delivery Vehicles," ACS Biomater. Sci. Eng., 2(2):213-223, (2016).
Mather et al., "Michael addition reactions in macromolecular design for emerging technologies," Prog. Polym. Sci., 31(5):487-531, (2006).
Mendelman, P. M. et al., "Aminoglycoside penetration, inactivation, and efficacy in cystic fibrosis sputum," Am. Rev. Respir. Dis., 132:761-765, (1985).
Miller et al., "Gaseous nitric oxide bactericidal activity retained during intermittent high-dose short duration exposure," Nitric Oxide, 20:16-23, (2009).
Miller et al., "Role of Oxidants in Microbial Pathophysiology," Clinical Microbiology Reviews, 10(1):1-18, (1997).
Miller, MR, and Megson, IL, "Recent developments in nitric oxide donor drugs," Br. J. Pharmacol., 151(3):305-321, (2007).
Minandri, F., "Promises and failures of gallium as an antibacterial agent," Future Microbiology, 9(3):379-397, (2014).
Moreno-Sastre et al., "Pulmonary delivery of tobramycin-loaded nanostructured lipid carriers for Pseudomonas aeruginosa infections associated with cystic fibrosis," International Journal of Pharmaceutics, 498:263-273, (2016).
Mourtzis et al., "Synthesis, characterization, and remarkable biological properties of cyclodextrins bearing guanidinoalkylamino and aminoalkylamino groups on their primary side," Chem. Eur. J., 14: 4188-4200 (2008).
Mulani et al., "Emerging Strategies to Combat ESKAPE Pathogens in the Era of Antimicrobial Resistance: A Review," Front. Microbiol., 10, (2019).
Müller, L. et al., "Human airway mucus alters susceptibility of Pseudomonas aeruginosa biofilms to tobramycin, but not colistin," J. Antimicrob. Chemother., 73:2762-2769, (2018).
Nair et al., "Biodegradable polymers as biomaterials," Prog. Polym. Sci., 32(8-9):762-798, (2007).
Nakamoto, H. and Bardwell, J.C.A., "Catalysis of Disulfide Bond Formation and Isomerization in the *Escherichia coli* Periplasm," Biochim. Biophys. Acta., 1694(1-3):111-119, (2004).
Newton, David E., Chemistry of New Materials, Shanghai Science and Technology Literature Press, p. 184, (Jul. 31, 2008).
Nguyen et al., "Co-delivery of nitric oxide and antibiotic using polymeric nanoparticles," Chem Sci., 7(2):1016-1027, (2016).
Nichols et al., "Local delivery of nitric oxide: Targeted delivery of therapeutics to bone and connective tissues," Adv. Drug Delivery Rev., 64(12):1177-1188, (2012).
Nordgard et al., "Alterations in Mucus Barrier Function and Matrix Structure Induced by Guluronate Oligomers," Biomacromolecules, 15:2294-2300, (2014).
Nordgard et al., "Oligosaccharides As Modulators of Rheology in Complex Mucous Systems," Biomacromolecules, 12(8):3084-3090, (2011).
O'Halloran, T.V. and Culotta, V.C., "Metallochaperones, an Intercellular Shuttle Service for Metal Ions," J. Biol. Chem., 275(33):25057-25060, (2000).
Johwada, Tomohiko, et al., "7-Azabicyclo [2.2. 1] heptane as a structural motif to block mutagenicity of nitrosamines," Bioorganic & Medicinal Chemistry, 19(8): 2726-2741, (2011).
Park et al., "Nitric oxide integrated polyethylenimine-based triblock copolymer for efficient antibacterial activity," Biomaterials, 34(34):8766-8775, (2013).
Park et al., "Polydopamine Hollow Nanoparticle Functionalized with N-diazeniumdiolates as a Nitric Oxide Delivery Carrier for Antibacterial Therapy," Adv. Healthcare Mater., 5(16):2019-2024, (2016).
Parzuchowski et al., "Synthesis and characterization of polymethacrylate-based nitric oxide donors," J. Am. Chem. Soc., 124(41):12182-12191, (2002).
Paster et al., "The breadth of bacterial diversity in the human periodontal pocket and other oral sites," Periodontology 2000, 42:80-87, (2006).
Paul et al., "Chitosan and Alginate Wound Dressings: A Short Review," Trends Biomater. Artif. Organs, 18(1):18-23, (2004).
Paula and Koo, "Nanosized building blocks for customizing novel antibiofilm approaches," J. Dent. Res., 96(2):128-136, (2017).

(56) References Cited

OTHER PUBLICATIONS

Petersen et al., "The global burden of oral diseases and risks to oral health," Bull. World Health Organ., 83(9):661-669, (2005).
Piras et al., "S-Nitroso-Beta-Cyclodextrins as New Bimodal Carriers: Preparation, Detailed Characterization, Nitric-Oxide Release, and Molecular Encapsulation," Chemistry—An Asian Journal, 8:2768-2778 (2013).
Polizzi et al., "Water-Soluble Nitric Oxide-Releasing Gold Nanoparticles," Langmuir, 23:4938-4943, (2007).
Prabaharan, M. et al., "Amphiphilic Multi-Arm-Block Copolymer Conjugated with Doxorubicin via pH-Sensitive Hydrazone Bond for Tumor-Targeted Drug Delivery," Biomaterials., 30(29):5757-5766, (2009).
Pritchard et al., "A New Class of Safe Oligosaccharide Polymer Therapy To Modify the Mucus Barrier of Chronic Respiratory Disease," Molecular Pharmaceutics, 13(3):863-872, (2016).
Privett et al., "Examination of Bacterial Resistance to Exogenous Nitric Oxide," Nitric Oxide, 26:169-173, (2012).
Privett, B. J., et al., "Synergy of nitric oxide and silver sulfadiazine against gram-negative, gram-positive, and antibiotic-resistant pathogens," Mol. Pharm., 7:2289- 2296, (2010).
Product Overview, "AR-501 (Gallium Citrate): Novel anti-infective for the growing problem of antibiotic resistance," Aridis Pharmaceuticals, (Last accessed Aug. 13, 2020), https://www.aridispharma.com/ar-501/.
Product Overview, "Ardis Pipeline: Blood Stream Infections : Product Candidates," Aridis Pharmaceuticals, (Last accessed Aug. 13, 2020), https://www.aridispharma.com/product-overview/.
PubChem CID 6032, "Kanamycin A," PubChem, NCBI, pp. 1-9, (2005).
Radvar et al., "Comparison of 3 periodontal local antibiotic therapies in persistent periodontal pockets," J. Periodontol., 67(9):860-865, (1996).
Ragheb, M. N. et al. "Inhibiting the Evolution of Antibiotic Resistance," Mol. Cell, 73:157-165.e5, (2019).
Rees et al., "Role of endothelium-derived nitric oxide in the regulation of blood pressure," Proc. Natl. Acad. Sci., 86(9):3375-3378, (1989).
Reighard et al., "Disruption and eradication of P. aeruginosa biofilms using nitric oxide-releasing chitosan oligosaccharides," Biofouling, 31:775-787, (2015).
Reighard, K. P. & Schoenfisch, M. H., "Antibacterial action of nitric oxide-releasing chitosan oligosaccharides against Pseudomonas aeruginosa under aerobic and anaerobic conditions," Antimicrob. Agents Chemother., 59:6506-6513, (2015).
Riccio and Sschoenfisch, "Nitric oxide release: part I. Macromolecular scaffolds," Chem. Soc. Rev., 41(10):3731-3741, (2012).
Riccio, D.A. et al., "Photoinitiated Nitric Oxide-Releasing Tertiary S-Nitrosothiol-Modified Xerogels," ACS Appl. Mater. Interfaces., 4(2):796-804, (2012).
Riccio, D.A. et al., "Stöber Synthesis of Nitric Oxide-Releasing S-Nitrosothiol-Modified Silica Particles," Chem. Mater., 23(7):1727-1735, (2011).
Robson, Martin C., "Wound Infection: A Failure of Wound Healing Caused by an Imbalance of Bacteria," Surgical Clinics of North America, 77(3):637-650, (1997).
Rouillard, K. R., et al., "Exogenous Nitric Oxide Improves Antibiotic Susceptibility in Resistant Bacteria," Research Presentation: Univ. of North of Carolina Chapel Hill, (2019).
Roy, B. et al., "New Thionitrates: Synthesis, Stability, and Nitric Oxide Generation," J. Org. Chem., 59(23):7019-7026, (1994).
Safdar et al., "Targeted diazeniumdiolates: Localized nitric oxide release from glioma-specific peptides and proteins," Int. J. Pharm., 422(1-2):264-270, (2012).
Santajit, S. & Indrawattana, N., "Mechanisms of Antimicrobial Resistance in ESKAPE Pathogens," Biomed Res. Int., 2016:1-8, (2016).
Schaffer et al., "Nitric oxide regulates wound healing," J. Surg. Res., 63(1):237-240, (1996).

Schairer et al., "The potential of nitric oxide releasing therapies as antimicrobial agents," Virulence, 3:271-279, (2012).
Schomburg et al., "Preparation, Purification, and Analysis of Alkylated Cyclodextrins," J. High Res. Chromatog., 15:579-584, (1992).
Seabra, A.B. et al., "Antibacterial Nitric Oxide-Releasing Polyester for the Coating of Blood-Contacting Artificial Materials," Artif. Organs, 34(7):E204-14, (2010).
Sen et al., "Periodontal Disease and Recurrent Vascular Events in Stroke/TIA Patients," J. Stroke Cerebrovasc. Dis., 22(8):1420-1427, (2013).
Shah et al., "Synthesis of S-nitrosoglutathione-alginate for prolonged delivery of nitric oxide in intestines," Drug Deliv., 23(8):2927-2935, (2016).
Shin et al., "Inorganic/Organic Hybrid Silica Nanoparticles as a Nitric Oxide Delivery Scaffold," Chem. Mater., 20:239-249, (2008).
Shishido, S.M. and Oliveira, M.G., "Polyethylene Glycol Matrix Reduces the Rates of Photochemical and Thermal Release of Nitric Oxide from S-Nitroso-N-Acetylcysteine," Photochem. Photobiol., 71(3):273-80, (2000).
Singh et al., "Biotechnological applications of cyclodextrins," Biotechnol. Adv., 20:341-359, (2002).
Singh, Simrat Pal, et al., "Rice Nicotianamine Synthase 2 expression improves dietary iron and zinc levels in wheat," Theoretical and Applied Genetics, 130(2): 283-292, (2017).
Slomberg, D.L. et al., "Role of Size and Shape on Biofilm Eradication for Nitric Oxide-releasing Silica," ACS Appl. Mater. Interfaces, 5(19):9322-9329, (2013).
Slots et al., "Antibiotics in periodontal therapy: advantages and disadvantages," J. Clin. Periodontol., 17(7 (Pt 2)):479-493, (1990).
Smith et al., "Nitric Oxide-Releasing Polymers Containing the AN(O)NoU-Group," Journal of Medicinal Chemistry, 39:1148-1157, (Jan. 1996).
Solleti et al., "Antimicrobial properties of liposomal azithromycin for Pseudomonas infections in cystic fibrosis patients," J. Antibicrob. Chemother., 70:784-796, (2015).
Soto et al., "Design Considerations for Silica-Particle-Doped Nitric-Oxide-Releasing Polyurethane Glucose Biosensor Membranes," ACS Sensors, 2(1): 140-150, (2017).
Soto et al., "Functionalized Mesoporous Silica via an Aminosilane Surfactant Ion Exchange Reaction: Controlled Scaffold Design and Nitric Oxide Release," ACS Appl. Mater. Interfaces, 8(3):2220-2231, (2016).
Southerland et al., "Periodontitis and diabetes associations with measures of atherosclerosis and CHD," Atherosclerosis, 222(1): 196-201, (2012).
Spellberg, B., et al., "The Epidemic of Antibiotic-Resistant Infections: A Call to Action for the Medical Community from the Infectious Diseases Society of America," Clin. Infect. Dis., 46:155-164, (2008).
Stasko and Schoenfisch, "Dendrimers as a Scaffold for Nitric Oxide Release," J. Am. Chem. Soc., 128(25):8265-8271, (2006).
Stasko et al., "Cytotoxicity of polypropylenimine dendrimer conjugates on cultured endothelial cells," Biomacromolecules, 8(12):3853-3859, (2007).
Stasko, N.A et al., "S-Nitrosothiol-Modified Dendrimers as Nitric Oxide Delivery Vehicles," Biomacromolecules, 9(3):834-841, (2008).
Suchyta and Schoenfisch, "Controlled release of nitric oxide from liposomes," ACS Biomater. Sci. Eng., 3(9):2136-2143, (2017).
Sun et al., "Nitric Oxide-Releasing Dendrimers as Antibacterial Agents," Biomacromolecules, 13(10):3343-3354, (2012).
Tomalia et al., "A New Class of Polymers: Starburst-Dendritic," Polym. J., 17:117-132, (1985).
Valko, M et al., "Metals, Toxicity and Oxidative Stress," Curr. Med. Chem., 12(10):1161- 1208, (2005).
Van Strydonck et al., "Plaque inhibition of two commercially available chlorhexidine mouthrinses," J. Clin. Periodontol., 32(3):305-309, (2005).
Vizitiu et al., "Binding of phosphates to aminocyclodextrin biomimetics," J. Org. Chem., 64(17):6235-6238, (1999).
Voit and Lederer, "Hyperbranched and highly branched polymer architectures—synthetic strategies and major characterization aspects," Chem. Rev., 109(11):5924-5973, (2009).

(56) References Cited

OTHER PUBLICATIONS

Wan, A., et al., "Characterization of folate-graft-chitosan as a scaffold for nitric oxide release," International Journal of Biological Macromolecules, Elsevier B.V. 43:415-421, (2008).
Wan, A., et al., "Effects of Molecular Weight and Degree of Acetylation on the Release of Nitric Oxide from Chitosan-Nitric Oxide Adducts," Journal of Applied Polymer Science, Wiley Periodicals, Inc., 117:2183-2188, (2010).
Wang et al., "Synthesis and applications of stimuli-responsive hyperbranched polymers," Prog. Polym. Sci., 64:114-153, (2017).
Wang et al., "Synthesis and gene delivery of poly(amido amine)s with different branched architecture," Biomacromolecules, 11(2):489-495, (2010).
Wang et al., "Bioapplications of hyperbranched polymers," Chemical Society Reviews, 44(12):4023-4071, (2015).
Wang et al., "Synthesis and evaluation of phenylalanine-modified hyperbranched poly (amido amine) s as promising gene carriers," Biomacromolecules, 11(1):241-251, (2009).
Wang et al., "The effect of a branched architecture on the antimicrobial activity of poly(sulfone amines) and poly(sulfone amine)/silver nanocomposites" J. Mater. Chem., 22:15227-15234, (2012).
Wang, J. and Xu, Tongwen, "Facile Construction of Multivalent Targeted Drug Delivery System from Boltorn® Series Hyperbranched Aliphatic Polyester an Folic Acid," Poly Adv Technol., 22:763-767, (2009).
Williams, D.L.H., "S-Nitrosation and the Reactions of S-Nitroso Compounds," Chem. Soc. Rev., 14(2):171-196, (1985).
Williams, D.L.H., "The Chemistry of S-Nitrosothiols," Acc. Chem. Res., 32(10): 869-876, (1999).
Wink et al., "DNA deaminating ability and genotoxicity of nitric oxide and its progenitors," Science, 254(5034):1001-1003, (1991).
Wo et al., "Recent advances in thromboresistant and antimicrobial polymers for biomedical applications: just say yes to nitric oxide (NO)," Biomater. Sci., 4(8):1161-1183, (2016).
Wold et al., "Fabrication of Biodegradable Polymeric Nanofibers with Covalently Attached NO Donors," ACS Appl. Mater. Interfaces, 4(6):3022-3030, (2012).
Worley et al., "Anti-Biofilm Efficacy of Dual-Action Nitric Oxide-Releasing Alkyl Chain Modified Poly(amidoamine) Dendrimers," Mol. Pharmaceutics, 12:1573-1583, (2015).
Worley et al., "Nitric Oxide-Releasing Quaternary Ammonium-Modified Poly(amidoamine) Dendrimers as Dual Action Antibacterial Agents," Bioconjugate Chem., 25(5):918-927, (2014).
Wu et al., "'Living' controlled in situ gelling systems: thiol-disulfide exchange method toward tailor-made biodegradable hydrogels," J. Am. Chem. Soc., 132(43):15140-15143, (2010).
Xiao, Y.L. et al., "Multifunctional Unimolecular Micelles for cancer-Targeted Drug Delivery and Positron Emission Tomography Imaging," Biomaterials, 33(11):3071-3082, (2012).
Xu et al., "Well-defined poly (2-hydroxyl-3-(2-hydroxyethylamino) propyl methacrylate) vectors with low toxicity and high gene transfection efficiency," Biomacromolecules, 11(6):1437-1442, (2010).
Yang et al., "S-Nitrosothiol-modified hyperbranched polyesters," Polym. Chem., 7(46):7161-7169, (2016).
Yang, Lei et al., "Antibacterial Activity of Nitric Oxide-Releasing Hyperbranched Polyamidoamines," Bioconjugate Chem., 29:35-43, (2018).
Yapor, J.P. et al., "Biodegradable Citrate-Based Polyesters with S-Nitrosothiol Functional Groups for Nitric Oxide Release," J. Mater. Chem. B., 3(48):9233-9241, (2015).
Žagar, E. and Žigon, M., "Aliphatic Hyperbranched Polyesters Based on 2,2-bis(methylol)propionic Acid—Determination of Structure, Solution and Bulk Properties," Prog. Polymer Sci., 36(1):53-88, (2011).
Zambon, Joseph J., "Actinobacillus actinomycetemcomitans in human periodontal disease," Journal of Clinical Periodontology, 12(1):1-20, (1985).
Zamboulis et al: "Polyglycerol Hyperbranched Polyesters: Synthesis, Properties and Pharmaceutical and Biomedical Applications," International Journal of Molecular Sciences, 20(24):6210, (2019).

Zeng, X.H. et al., "Endocytic Uptake and Intracellular Trafficking of Bis-MPA-Based Hyperbranched Copolymer Micelles in Breast Cancer Cells," Biomacromolecules, 13(11):3814-3822, (2012).
Zhai, X. et al., "Amphiphilic Dendritic Molecules: Hyperbranched Polyesters with Alkyl-Terminated Branches," Macromolecules, 36(9):3101-3110, (2003).
Zhang et al., "Nitric oxide-releasing fumed silica particles: synthesis, characterization, and biomedical application," J. Am. Chem. Soc., 125(17):5015-5024, (2003).
Zhang et al., "A physical gel made from hyperbranched polymer gelator," Chem. Commun., 25:2587-2589, (2007).
Zhang et al., "Antibacterial cotton fabric grafted with silver nanoparticles and its excellent laundering durability," Carbohydr. Polym., 92(2):2088-2094, (2013).
Zhang et al., "Synthesis of an amino-terminated hyperbranched polymer and its application in reactive dyeing on cotton as a salt-free dyeing auxiliary," Color. Technol., 123(6):351-357, (2007).
Zhang et al., "The antimicrobial activity of the cotton fabric grafted with an amino-terminated hyperbranched polymer," Cellulose, 16:281-288, (2009).
Zhang, H. et al., "Hyperbranched Polyester Hydrogels with Controlled Drug Release and Cell Adhesion Properties," Biomacromolecules, 14(5):1299-1310, (2013).
Zhang, X.F. et al., "Nitric Oxide Delivery by Core/Shell Superparamagnetic Nanoparticle Vehicles with Enhanced Biocompatibility," Langmuir., 28(35):12879-12885, (2012).
Zheng et al., "Hyperbranched polymers: Advances from synthesis to applications," Chemical Society Reviews, 44(12):4091-4130, (2015).
Zhong, Yong-Li, et al., "Scalable Synthesis of Diazeniumdiolates: Application to the Preparation of MK-8150," Organic letters, 21(11):4210-4214, (2019).
Zhou et al., "Polymethacrylate-Based Nitric Oxide Donors with Pendant N-Diazeniumdiolated Alkyldiamine Moieties: Synthesis, Characterization, and Preparation of Nitric Oxide Releasing Polymeric Coatings," Biomacromolecules, 6:780-789, (2005).
Zhou et al., "Water-soluble poly (ethylenimine)-based nitric oxide donors: preparation, characterization, and potential application in hemodialysis," Biomacromolecules, 7(9):2565-2574, (2006).
Zhu et al., "Influence of Branching Architecture on Polymer Properties," Journal of Polymer Science Part B: Polymer Physics, 49(18):1277-1286, (2011).
Australian Application 2018205823, Examination Report No. 1 for standard patent application mailed Sep. 15, 2021.
Chinese Application No. 201880080277.6, First Office Action, dated Sep. 3, 2021.
EP Application No. 18812540.5, Communication Pursuant to Article 94(3) mailed Oct. 14, 2021.
EP Application No. 19763961.0, Extended European Search Report mailed Nov. 19, 2021.
European Application No. 18775628.3, Extended European Search Report mailed Sep. 28, 2020.
European Application No. 18812540.5, Communication pursuant to Rules 161(1) and 162 EPC, dated Jul. 8, 2020.
European Search Report and Search Opinon mailed on Aug. 3, 2020 by the European Search Authority for EP Application No. 18736471.6 (8 pages).
European Search Report mailed on May 4, 2020 by the European Search Authority for EP Application No. 17859196.2 (32 pages).
JP Application No. 2019-556425, Notice of Reasons for Refusal mailed Oct. 26, 2021.
Supplementary European Search Report mailed Feb. 5, 2016 in EP Application No. 13829755.1.
U.S. Appl. No. 16/459,015, Requirement for Restriction/Election mailed Oct. 9, 2019.
U.S. Appl. No. 16/725,566, Non-Final Office Action mailed Jun. 10, 2021.
WIPO Application No. PCT/IB2018/050051, PCT International Search Report and Written Opinion of the International Searching Authority mailed Jun. 8, 2018.
WIPO Application No. PCT/IB2018/052144, PCT International Search Report and Written Opinion of the International Searching Authority mailed Aug. 8, 2018.

(56) References Cited

OTHER PUBLICATIONS

WIPO Application No. PCT/US2013/055360, PCT International Search Report and Written Opinion of the International Searching Authority mailed Dec. 23, 2013.
WIPO Application No. PCT/US2017/055371, PCT International Preliminary Report on Patentability mailed Apr. 9, 2019.
WIPO Application No. PCT/US2017/055371, PCT International Search Report and Written Opinion of the International Searching Authority mailed Dec. 28, 2017.
WIPO Application No. PCT/US2018/061061, PCT International Search Report and Written Opinion of the International Searching Authority mailed Apr. 5, 2019.
WIPO Application No. PCT/US2019/021051, PCT International Search Report and Written Opinion of the International Searching Authority mailed Jun. 21, 2019.
WIPO Application No. PCT/US2019/068412, PCT International Preliminary Report on Patentability mailed Jul. 8, 2021.
WIPO Application No. PCT/US2019/068412, PCT International Search Report and Written Opinion of the International Searching Authority mailed May 21, 2020.
U.S. Appl. No. 16/725,566, filed Dec. 23, 2019, U.S. Pat. No. 11,421,044, Allowed.

\* cited by examiner

NITRIC OXIDE-RELEASING ANTIBACTERIAL POLYMERS AND SCAFFOLDS FABRICATED THEREFROM AND METHODS PERTAINING THERETO

CROSS-REFERENCE TO RELATED APPLICATIONS

This application is a division of U.S. application Ser. No. 16/725,566, filed Dec. 23, 2019, which claims priority to U.S. Provisional Application No. 62/786,098, filed on Dec. 28, 2018, the contents of which are incorporated herein by reference in their entirety.

GOVERNMENT INTEREST

This invention was made with government support under Grant Nos. DK108318 and DE025207 and awarded by The National Institutes of Health. The Government has certain rights in the invention.

FIELD

The presently disclosed subject matter relates generally to nitric oxide-releasing polymers and scaffolds made therefrom that store and/or release nitric oxide in a controlled manner. Additionally disclosed are methods of synthesis of the same and methods of use of the same as antibacterial agents in methods of treatment.

BACKGROUND

Bacterial infections pose a great challenge to human health in community and hospital settings. Biofilms are cooperative communities of bacteria encapsulated by an exopolysaccharide (EPS) matrix protecting the bacteria from host immune response and antibiotics.

SUMMARY

Nitric oxide (NO) plays a variety of physiological roles as a signaling molecule and, as disclosed herein, can also play significant roles in treating or ameliorating pathophysiology, for example as a therapeutic agent. NO as a therapeutic has heretofore been underused, based at least in part on limited NO payloads of therapeutic compositions, NO release rates that are more rapid than desired, and the lack of targeted NO delivery. Provided herein are NO-releasing polymers and scaffolds, methods of producing such polymers and scaffolds, and methods of treating various pathophysiologies using such polymers and scaffolds that leverage enhanced NO-release characteristics and beneficial physical properties, harnessing the abundant potential of NO-releasing pharmacological compounds and compositions. In several embodiments, provided herein are compounds and compositions that are highly efficacious as antimicrobials. In several embodiments, provided herein are compounds and compositions with beneficial antimicrobial properties as well as physical properties, such as viscosity and gelation. In several embodiments, the polymers and/or scaffolds disclosed herein have advantageous activity as viscosity enhancing agents.

For example, in several embodiments there is provided one or more macromolecular structures that release NO and exhibit potent antimicrobial characteristics. In several embodiments, the macromolecular structures are polymers. While, in several embodiments, the polymers can be used as dilute solutions (e.g., for vaporization and inhalation, etc.), in other embodiments, the polymers can be self-assembled in solution and/or can be crosslinked to provide scaffolds with advantageous physical properties (including three-dimensional shape, firmness, adhesiveness, and viscosity). In several embodiments, the polymers retain beneficial antimicrobial activity even as gels and viscous liquids.

In several embodiments, a polymer having structural units along a chain of the polymer is provided. In several embodiments, one or more of the structural units is functionalized with one or more instances of each of $R_1$, $R_2$, $R_3$, $R_4$, $R_5$, and $R_6$. In several embodiments, $R_1$, $R_2$, $R_3$, $R_4$, $R_5$, and $R_6$ can comprise functional units that imbue the polymer with desired properties. In several embodiments, $R_1$, $R_2$, $R_3$, $R_4$, $R_5$, and $R_6$ can comprise NO binding moieties. In several embodiments, each instance of $R_1$, $R_2$, $R_3$, $R_4$, $R_5$, and $R_6$ along the polymer chain (e.g., on one or more structural units) is independently selected from one or more of —OH, —NH$_2$, —OCH$_3$, —C(O)OH, —CH$_2$OH, —CH$_2$OCH$_3$, —CH$_2$OCH$_2$CH$_2$OH, —OCH$_2$C(O)O H, —CH$_2$OCH$_2$C(O)OH, —CH$_2$C(O)OH, —NHC(O)—CH$_3$, —C(O)O((CH$_2$)$_a$O)$_b$—H, —C(O)O((CH$_2$)$_a$O)$_b$—(CH$_2$)$_c$H, —C(O)O(C$_{1-5}$alkyl), —C(O)—NH—((CH$_2$)$_d$NH)$_e$—H, —C(O)—NH—((CH$_2$)$_d$NH)$_e$—(CH$_2$)$_f$H, —C(O)—X$^1$—((CH$_2$)$_g$X$^2$)$_h$—(CH$_2$)$_i$H, —C(O)—X$^1$—((CH$_2$)$_g$X$^2$)$_h$((CH$_2$)$_j$X$^3$)$_k$—(CH$_2$)$_i$H, —O—((CH$_2$)$_a$O)$_b$—H, —O—((CH$_2$(_a$O)$_b$—(CH$_2$)$_c$H, —O—(C$_{1-5}$alkyl), —NH—((CH$_2$)$_d$N H)$_e$—(CH$_2$)$_f$H, and —X$^1$—((CH$_2$)$_g$X$^2$)$_h$—(CH$_2$)$_i$H, —X$^1$—((CH$_2$)$_g$X$^2$)$_h$((CH$_2$)$_j$X$^3$)$_k$—(CH$_2$)$_i$H. In some embodiments, each instance of a, b, c, d, e, f, g, h, i, j, k, and l is independently selected from an integer of 0, 1, 2, 3, 4, 5, 6, 7, 8, 9, or 10. In several embodiments, each of a, b, c, d, e, f, g, h, i, j, k, and l can be independently greater than 10. In several embodiments, each instance of $X^1$, $X^2$, and $X^3$ is independently selected from —O—, —S—, —NH—, and C(O)NH—. In several embodiments, at least one instance of $X^1$, $X^2$, and $X^3$ is a NO donating moiety. In several embodiments, at least one instance of $X^1$, $X^2$, and $X^3$ is represented by one of the following:

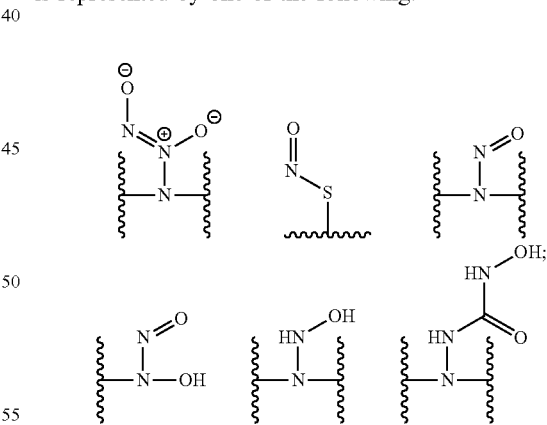

and

In several embodiments, each instance of $R_1$, $R_2$, $R_3$, $R_4$, $R_5$, or $R_6$ is independently selected from the group consisting of:

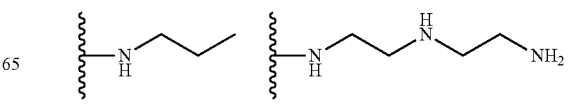

-continued

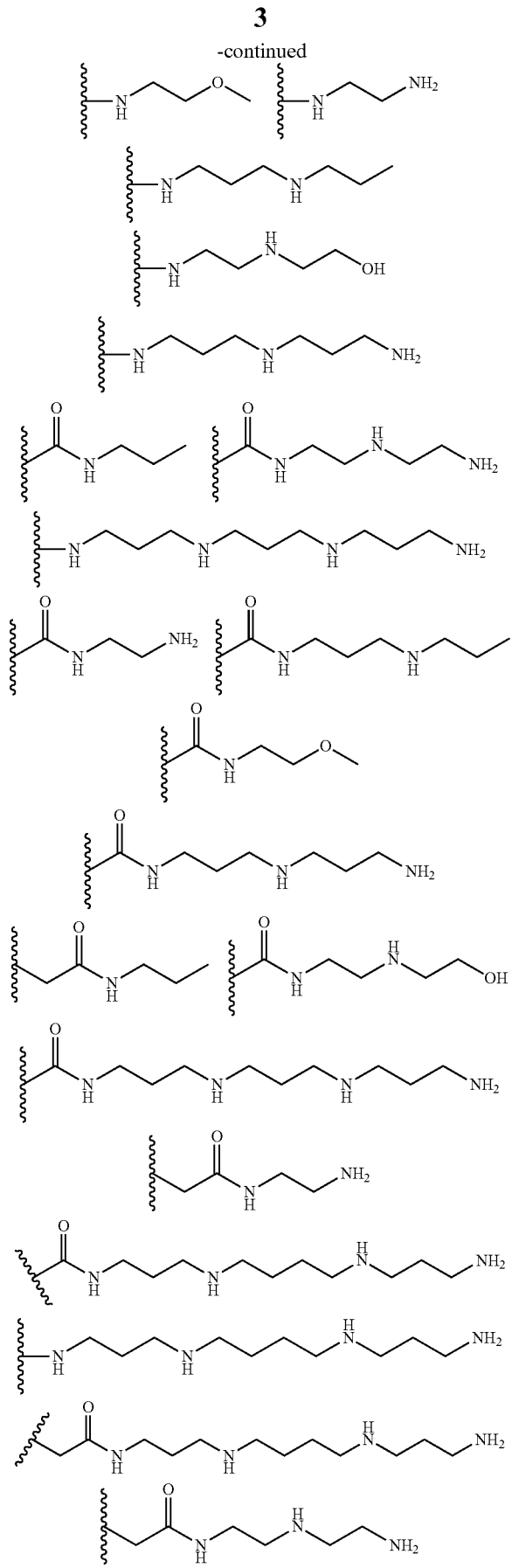

-continued

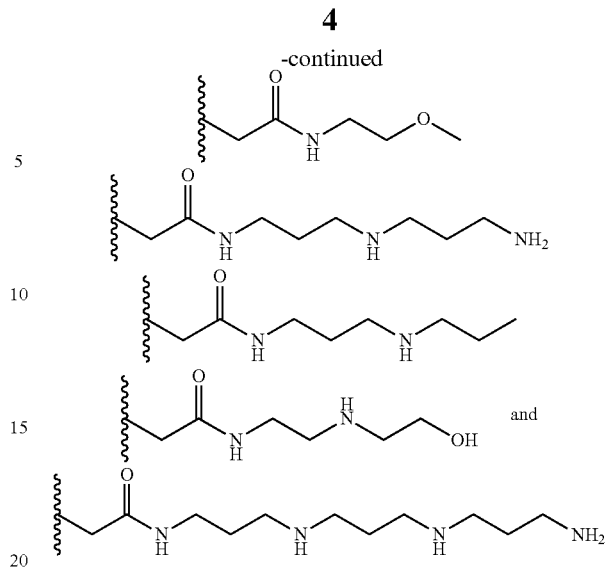

In several embodiments, each secondary amine of the above structures may be functionalized with a NO donating group as disclosed herein.

In several embodiments, the polymer (or scaffold made therefrom) has a viscosity of equal to or at least about 10 mPa·s at 20° C. at a concentration of 5% w/w. In several embodiments, the polymer (or scaffold made therefrom) has a gel firmness of equal to or at least about 1.0 Nm at a concentration of 5% w/w. In several embodiments, the viscosity can be greater, such as for example, about 10 mPa·s, about 20 mPa·s, about 30 mPa·s, about 50 mPa·s, about 60 mPa·s, about 70 mPa·s, about 80 mPa·s, about 90 mPa·s, about 100 mPa·s, or any viscosity therebetween. In several embodiments, the gel firmness can be greater, for example about 5 Nm, about 10 Nm, about 20 Nm, about 30 Nm, about 40 Nm, about 50 Nm, about 75 Nm, about 100 Nm, or any gel firmness therebetween.

In several embodiments, the polymer is a biopolymer. In several embodiments, the polymer is a polysaccharide. In several embodiments, the one or more structural units are represented by saccharide unit of Formula I:

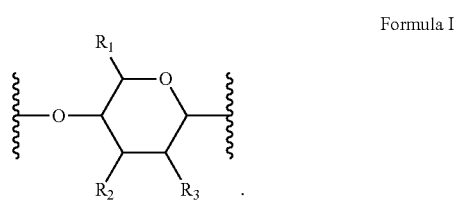

Formula I

In several embodiments, the saccharide unit is representative of a carboxymethylcellulose structural unit. In several embodiments, the structure of Formula I represents a saccharide unit of a hyaluronic acid polymer. In several embodiments, the structure of Formula I represents a saccharide unit of a hydroxyethyl cellulose polymer. In several embodiments, the structure of Formula I represents a saccharide unit of a methyl cellulose polymer. In several embodiments, the structure of Formula I represents a saccharide unit of an alginate polymer. In several embodiments, the structure of Formula I represents a saccharide unit of a cyclodextrin ring structure.

In several embodiments, provided herein is a NO releasing carboxymethylcellulose-derived polymer compound, comprising a unit structure of Formula I:

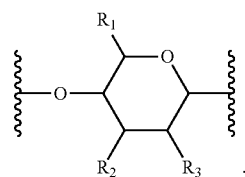

Formula I

In several embodiments, $R_1$, $R_2$, and $R_3$ are independently selected from —OH, —CH$_2$OH, —OCH$_2$C(O)OH, —CH$_2$OCH$_2$C(O)OH, —C(O)—O—((CH$_2$)$_a$O)$_b$—H, —C(O)—O—((CH$_2$)$_a$O)$_b$—(CH$_2$)$_c$H, —C(O)—O—(C$_{1-5}$alkyl), —C(O)—NH—((CH$_2$)$_d$NH)$_e$—H, —C(O)—NH—((CH$_2$)$_l$)$_d$NH)$_e$—(CH$_2$)$_f$H, —C(O)—X$^1$((CH$_2$)$_g$X$^2$)$_h$—(CH$_2$)$_i$H, —C(O)—X$^1$—((CH$_2$)$_g$X$^2$)$_h$((CH$_2$)$_j$X$^3$)$_k$—(CH$_2$)$_l$H, —O—((CH$_2$)$_a$O)$_b$—H, —O—((CH$_2$)$_a$O)$_b$—(CH$_2$)$_c$H, —O—(C$_{1-5}$alkyl), —NH—((CH$_2$)$_d$NH)$_e$—H, —NH—((CH$_2$)$_d$NH)$_e$—(CH$_2$)$_f$H, —X$^1$—((CH$_2$)$_g$X$^2$)$_h$—(CH$_2$)$_i$H, —X$^1$—((CH$_2$)$_g$X$^2$)$_h$((CH$_2$)$_j$X$^3$)$_k$—(CH$_2$)$_l$H. In several embodiments, each instance of a, b, c, d, e, f, g, h, i, j, k, and l is independently selected from an integer of 0, 1, 2, 3, 4, 5, 6, 7, 8, 9, or 10. In several embodiments, each instance of $X^1$, $X^2$, and $X^3$ is independently selected from —O—, —S—, —NH—, C(O)NH—. In several embodiments, at least one of $X^1$, $X^2$, and $X^3$ is represented by one of the following:

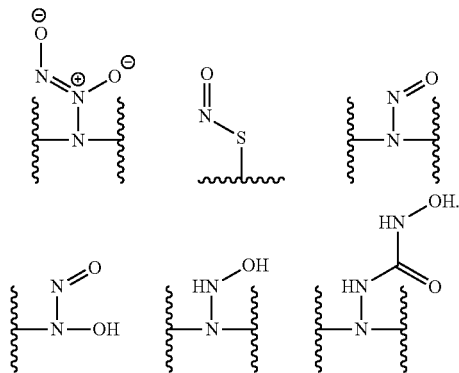

In several embodiments, the carboxymethylcellulose-derived polymer compound has a viscosity of equal to or at least about 10 mPa·s at 20° C. at a concentration of 5% w/w in water.

In several embodiments, Formula I has the stereochemical configuration shown in Formula I':

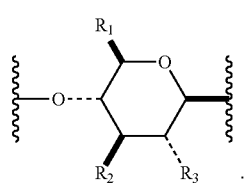

Formula I'

In several embodiments, the at least one of $X^1$, $X^2$, and $X^3$ is represented by the following:

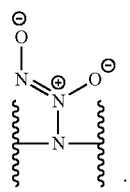 [SMILES: *N(*)/[N+]([O-])=N/[O-]]

In several embodiments, the $R^1$ is —CH$_2$C(O)—X$^1$—((CH$_2$)$_g$X$^2$)$_h$((CH$_2$)$_j$X$^3$)$_k$—(CH$_2$)$_l$H. In several embodiments, $R_2$ and $R_3$ are —OH. In several embodiments, each instance of $R_1$, $R_2$, and $R_3$ is independently selected from the group consisting of:

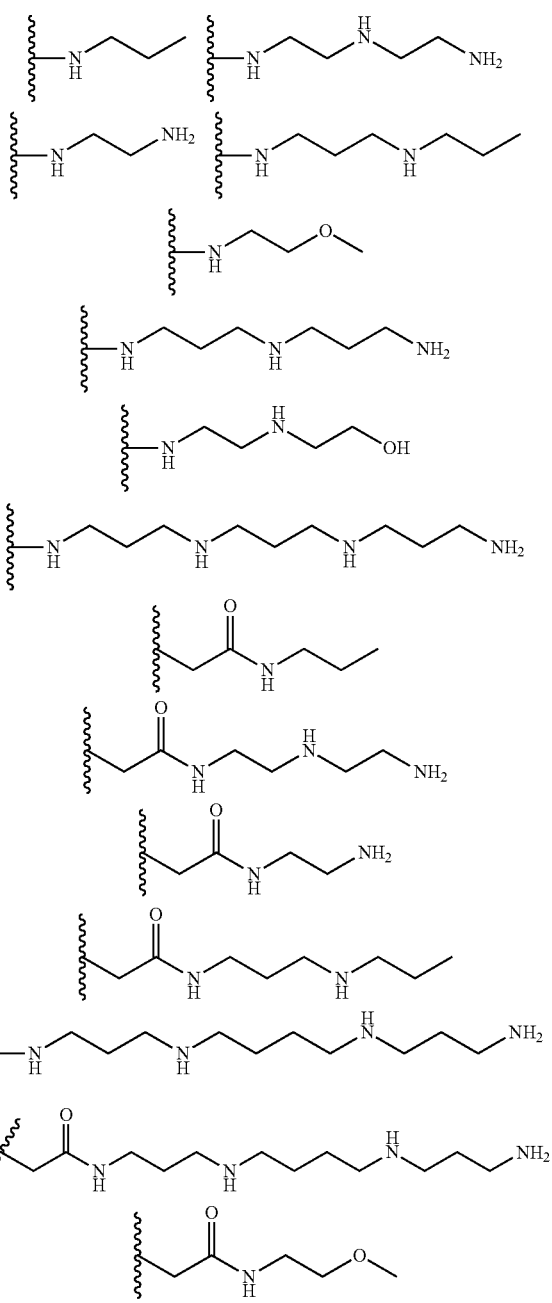

-continued

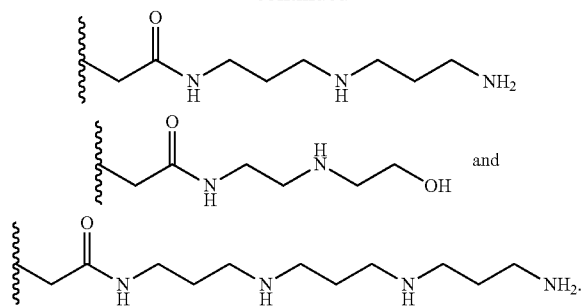

In several embodiments, the compound has a viscosity of equal to or at least about 20 mPa·s at 20° C. at a concentration of 20% w/w in water. In several embodiments, the compound is soluble in water at a concentration of 50 mg/ml. In several embodiments, the compound has a total releasable NO storage in a range of 0.1-1.0 mol of NO per mg of compound. In several embodiments, the compound has a NO half-life in the range of 0.1-24 hours. In several embodiments, the compound has a total duration of NO release in the range of 1-60 hours. In several embodiments, the total NO release after 4 hours is in the range between 0.1-1.0 mol of NO per mg of compound. In several embodiments, more than 15% of the repeat units in the compound are monomers of Formula I. In several embodiments, the compound has a molecular weight in the range of about 90 kDa and about 700 kDa. In several embodiments, the compound comprises two or more different covalently modified monomers of Formula I.

In several embodiments, provided herein is an NO releasing hyaluronic acid-derived polymer compound, comprising a unit structure of Formula II:

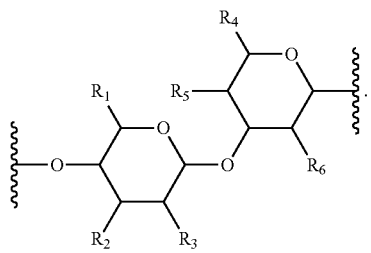

Formula II

In several embodiments, each instance of $R_1$, $R_2$, $R_3$, $R_4$, $R_5$, and $R_6$ is independently —OH, —NH$_2$, —CH$_2$OH, —C(O)OH, —NHC(O)—CH$_3$, —O—((CH$_2$)$_a$O)$_b$—H, —O—((CH$_2$)$_a$O)$_b$—(CH$_2$)$_c$H, —O—(C$_{1-5}$alkyl), —NH—((CH$_2$)$_d$NH)$_e$—H, —NH—((CH$_2$)$_d$NH)$_e$—(CH$_2$)$_f$H, —X$^1$—((CH$_2$)$_g$X$^2$)$_h$—H, —X$^1$—((CH$_2$)$_g$X$^2$)$_h$—(CH$_2$)$_i$H, or —X$^1$—((CH$_2$)$_g$X$^2$)$_h$((CH$_2$)$_j$X$^3$)$_k$—(CH$_2$)$_l$H. In several embodiments, each instance of a, b, c, d, e, f, g, h, i, j, k, and l is independently selected from an integer of 0, 1, 2, 3, 4, 5, 6, 7, 8, 9, or 10. In several embodiments, each instance of $X^1$, $X^2$, and $X^3$ is independently selected from —O—, —S—, —NH—, C(O)NH—. In several embodiments, at least one of $X^1$, $X^2$, and $X^3$ is represented by one of the following:

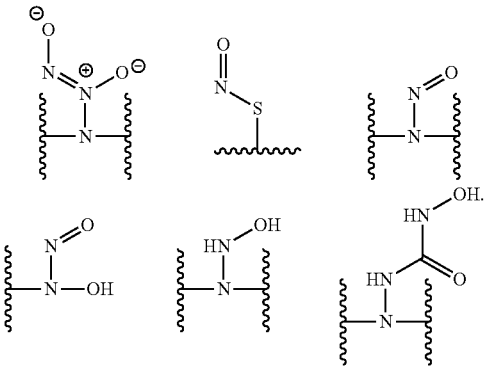

In several embodiments, the compound has a viscosity of equal to or at least about 10 mPa·s at 20° C. at a concentration of 5% w/w in water.

In several embodiments, Formula II has the stereochemical configuration shown in Formula II':

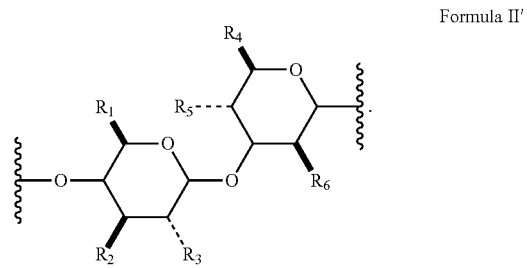

Formula II'

In several embodiments, at least one of $X^1$, $X^2$, and $X^3$ is represented by the following:

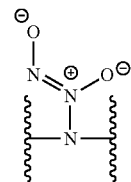

In several embodiments, $R^1$ is —CH$_2$C(O)—X$^1$—((CH$_2$)$_g$X$^2$)$_h$((CH$_2$)$_j$X$^3$)$_k$—(CH$_2$)$_l$H. In several embodiments, $R_2$ and $R_3$ are —OH. In several embodiments, one or more of $R_1$, $R_2$, $R_3$, $R_4$, $R_5$, and $R_6$ are independently selected from the group consisting of:

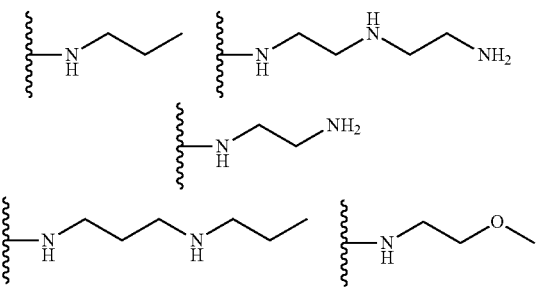

-continued

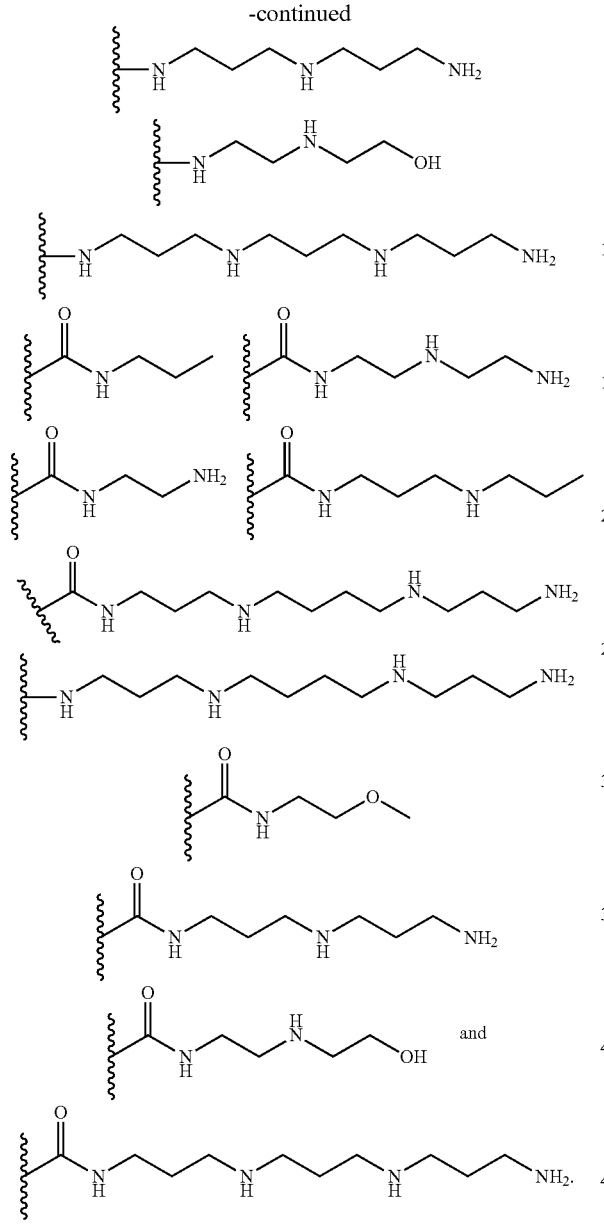

In several embodiments, the compound has a viscosity of equal to or at least about 20 mPa·s at 20° C. at a concentration of 20% w/w in water. In several embodiments, the compound is soluble in water at a concentration of 50 mg/ml. In several embodiments, the compound has a total releasable NO storage in a range of 0.1-1.0 mol of NO per mg of compound. In several embodiments, the compound has a NO half-life in the range of 0.1-24 hours. In several embodiments, the compound has a total duration of NO release in the range of 1-60 hours. In several embodiments, the total NO release after 4 hours is in the range between 0.1-1.0 mol of NO per mg of compound. In several embodiments, the compound has a molecular weight in the range of about 6 kDa and about 90 kDa.

In several embodiments, the polymer comprises a polyaminoglycoside. In several embodiments, the polyaminoglycoside is a hyperbranched polyaminoglycoside, comprising a first aminoglycoside of Formula III:

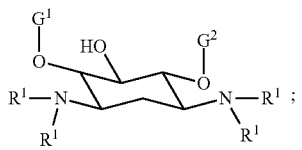

Formula III wherein $G^1$ is selected from the group consisting of:

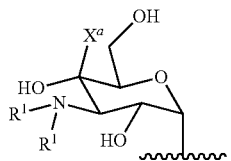 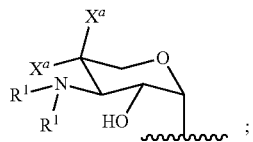

wherein $G^2$ is selected from the group consisting of:

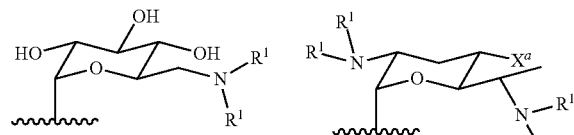

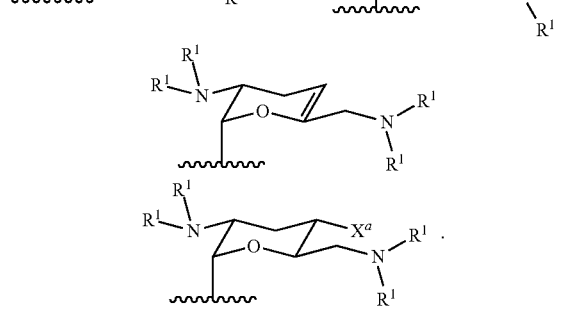

In several embodiments, the each instance of $R^1$ is independently selected from the group consisting of —H, optionally substituted $C_1$-$C_6$ alkyl, optionally substituted polyamino having 1 to 6 repeat units with intervening $C_1$-$C_6$ alkyl groups, optionally substituted polyether having 1 to 6 repeat units with intervening $C_1$-$C_6$ alkyl groups, or indicates a covalent bond to a linking unit. In several embodiments, each instance of $X^a$ is independently selected from —H, —OH, and $C_1$-$C_6$ alkyl. In several embodiments, at least one instance of $R^1$ indicates a covalent bond to one or more linking unit selected from the following:

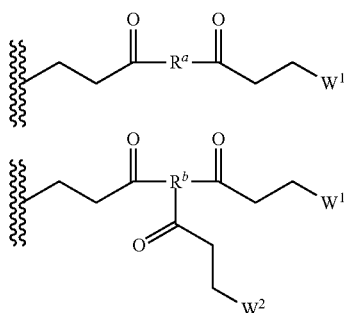

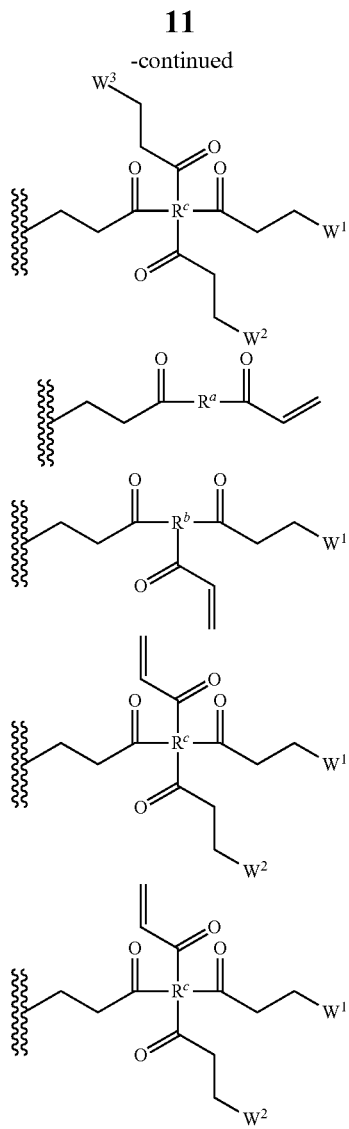

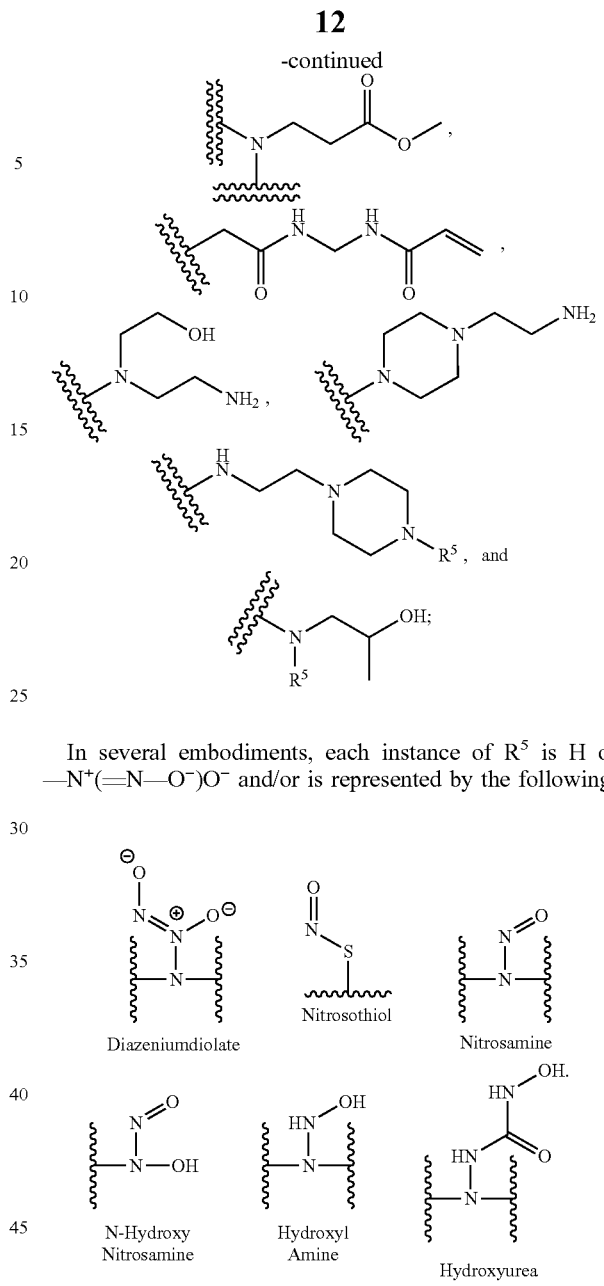

wherein "⌇⌇" indicates an attachment to the first aminoglycoside. In several embodiments, each instance of $W^1$, where present, is independently selected from one or more additional aminoglycosides or one or more end-capping substituents and at least one linking unit provides a covalent bridge from the first aminoglycoside to a second aminoglycoside. In several embodiments, each instance of $R^a$ is independently selected from the group consisting of optionally substituted $C_1$-$C_6$alkyl, optionally substituted polyamino having 1 to 6 repeat units (with $C_1$-$C_6$ alkyl(s)), or optionally substituted polyether having 1 to 6 repeat units (with $C_1$-$C_6$ alkyl(s)). In several embodiments, the one or more end-capping substituents, where present, independently has a formula of —$X^1$—(($CH_2$)$_h$$X^2$)$_i$($CH_2$)$_j$H.

In several embodiments, the polymer further comprises an end group selected from the group consisting of:

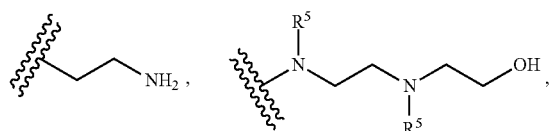

In several embodiments, each instance of $R^5$ is H or —$N^+$(=N—$O^-$)$O^-$ and/or is represented by the following:

Diazeniumdiolate    Nitrosothiol    Nitrosamine

N-Hydroxy Nitrosamine    Hydroxyl Amine    Hydroxyurea

In several embodiments, the polymer comprises an end group selected from the group consisting of:

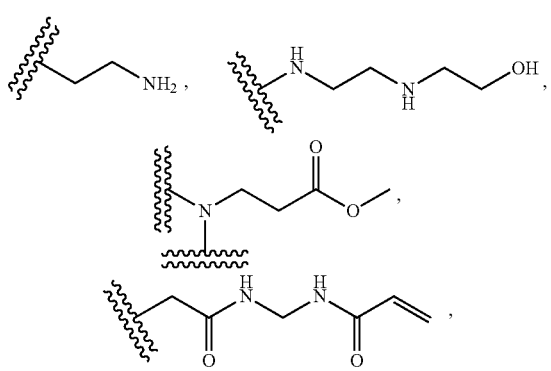

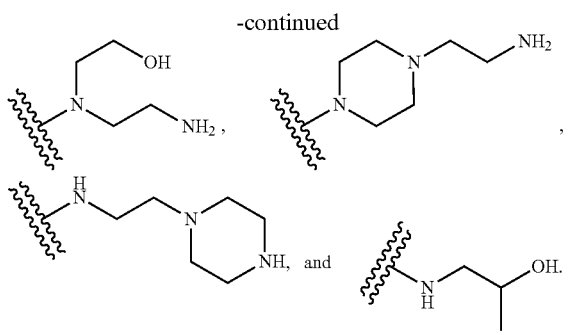

Several embodiments pertain to a method of delivering nitric oxide to a subject in need of treatment. In several embodiments, an effective amount of the compounds or viscosity inducing agents is administered to the subject. In several embodiments, the effective amount of the compounds or viscosity inducing agents is administered as a hydrogel or the hydrogel is formed at the site of administration (e.g., in vivo). In several embodiments, the subject is a patient who has suffered a wound and the compounds or viscosity inducing agents are administered to aid in wound healing. In several embodiments, the subject is in need of tissue replacement and the compounds or viscosity inducing agents are administered as a tissue scaffold or filler and/or tissue re-growth promoting agents.

Several embodiments pertain to a method of treating a disease state. In several embodiments, an effective amount of the compounds or viscosity inducing agents is administered to a subject in need thereof, wherein said disease state is selected from the group consisting of a cancer, a cardiovascular disease, a microbial infection, platelet aggregation and platelet adhesion caused by the exposure of blood to a medical device, pathological conditions resulting from abnormal cell proliferation, transplantation rejections, autoimmune diseases, inflammation, vascular diseases, scar tissue, wound contraction, restenosis, pain, fever, gastrointestinal disorders, respiratory disorders, sexual dysfunctions, and sexually transmitted diseases.

Some embodiments pertain to a pharmaceutical formulation comprising the compounds (e.g., polymers) or viscosity inducing agents and a pharmaceutically acceptable excipient.

Some embodiments pertain to a method of reducing or preventing microbial load on a surface. In several embodiments, the compounds or viscosity inducing agents are applied to a surface contaminated with a plurality of microbes. In several embodiments, the compounds or viscosity generate nitric oxide and induce oxidative and/or nitrosative damage to microbial DNA and membrane structures, thereby preventing or reducing microbial load. In several embodiments, the plurality of microbes comprises one, two, or more of the following: gram-positive bacteria, gram-negative bacteria, fungi, yeast, and viruses. In several embodiments, the surface is an organic surface. In several embodiments, the surface is human skin. In several embodiments, the surface is an epithelial tissue. In several embodiments, the surface is a wound surface. In several embodiments, the surface is animal skin. In several embodiments, the application does not induce skin irritation.

In several embodiments, the surface is an inorganic surface. In several embodiments, the inorganic surface is an external or internal surface of a medical device. In several embodiments, the application of the compound generates an anti-microbial coating on the external or internal surface of the medical device. In several embodiments, the medical device comprises an endoscope.

In several embodiments, the microbial load comprises drug-resistant bacteria. In several embodiments, the microbial load comprises microbes associated with the presence of one or more of human immunodeficiency virus, herpes simplex virus, papilloma virus, parainfluenza virus, influenza, hepatitis, Coxsackie Virus, herpes zoster, measles, mumps, rubella, rabies, pneumonia, hemorrhagic viral fevers, H1N1, prions, parasites, fungi, mold, *Candida albicans, Aspergillus niger, Escherichia coli, Pseudomonas aeruginosa*, and *Staphylococcus aureus*, Group A streptococci, *S. pneumoniae, Mycobacterium tuberculosis, Campylobacter jejuni, Salmonella, Shigella*, carbapenem-resistant Enterobacteriaceae Methicillin-resistant *Staphylococcus aureus*, and Burkholderia cepacia. In several embodiments, the microbial load comprises Methicillin-resistant *Staphylococcus aureus*. In several embodiments, the microbial load comprises carbapenem-resistant Enterobacteriaceae. In several embodiments, the microbial load comprises *Staphylococcus aureus*. In several embodiments, the microbial load comprises *Pseudomonas aeruginosa*. In several embodiments, the microbial load comprises Burkholderia cepacia. In several embodiments, the NO donor generates nitric oxide and induces damage to the membrane and/or DNA of the microbes, thereby reducing the number of viable microbes. In several embodiments, the plurality of microbes comprises one or more of viruses, gram positive bacteria, gram negative bacteria, drug resistant bacteria, molds, yeasts, fungi, and combinations thereof.

Some embodiments pertain to a method of preventing and/or decreasing microbial contamination. In some embodiments, the method comprises contacting a surface contaminated with a plurality of microbes (or that a surface that could be exposed to microbes) with a NO-releasing scaffold. In some embodiments, a NO-donor of the scaffold generates NO and induces damage to the membrane and/or DNA of the microbes, thereby reducing the number of viable microbes and/or preventing the colonization or infection of an area with microbes. In several embodiments, the surface comprises an organic surface. In some embodiments of the method, the surface is human skin or animal skin. In some embodiments of the method, the surface is in the mouth, or surrounding tissues (e.g., lips, nasal nares, teeth, gums, etc.). In several embodiments, the surface comprises the oral mucosa. In some embodiments, the surface is in the lungs. In some embodiments, the surface is an inorganic surface (of a device, etc.). In several embodiments, the surface is an inorganic surface. In several embodiments, the inorganic surface is an external or internal surface of a medical device. In several embodiments, the device is a dental device. Advantageously, in some embodiments of the method, the application step does not induce skin or tissue irritation. In some embodiments, the plurality of microbes comprises one or more of viruses, gram positive bacteria, gram negative bacteria, drug resistant bacteria, molds, yeasts, fungi, and combinations thereof.

Several embodiments pertain to a method of manufacturing any one of the compounds or viscosity inducing agents disclosed herein, comprising selecting a polymer and functionalizing the polymer with a NO binding moiety. In several embodiments, the polymer is a biopolymer. In several embodiments, the method includes exposing the compounds or viscosity inducing agents to NO to provide a NO donating compound or viscosity inducing agent.

The compositions and related methods set forth in further detail below describe certain actions taken by a practitioner;

however, it should be understood that they can also include the instructions of those actions by another party. Thus, actions such as "administering a NO-donating scaffold" include "instructing the administration of a NO-donating scaffold."

BRIEF DESCRIPTION OF THE DRAWINGS

In FIG. 12 A2, HA6 is the left bar of each pair of bars. (B) shows dose of NO released from hyaluronic acid derivatives required to reduce enzymatic activity by 50%.

DETAILED DESCRIPTION

Figure 1:
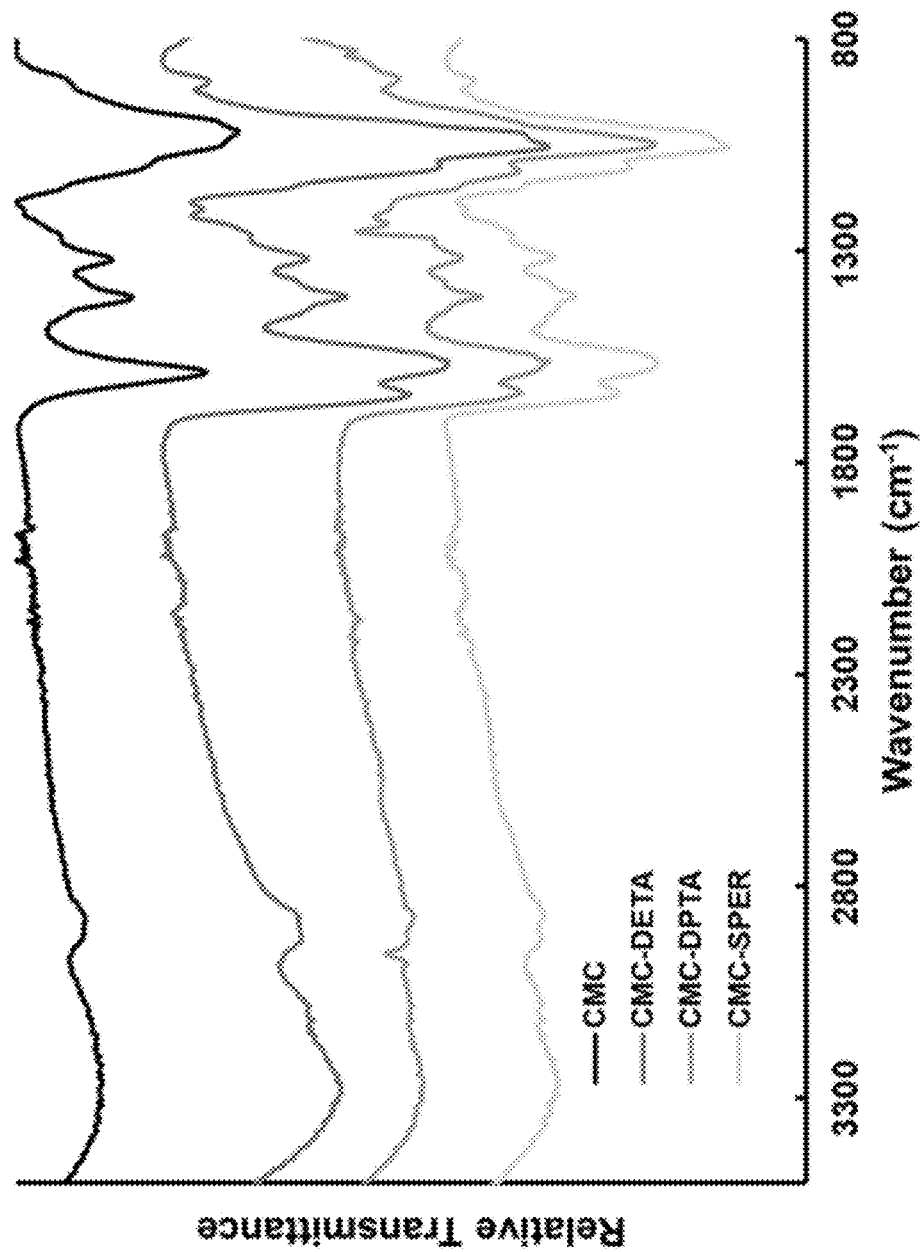
FIG. 1 shows FTIR analysis of amine-modified CMC.

Several embodiments disclosed herein provide the synthesis and characterization of N-diazeniumdiolate NO donor-modified scaffolds and their use in antimicrobial applications. In several embodiments, the scaffolds comprise polymers. In several embodiments, the scaffolds comprise biopolymers. In several embodiments, the scaffolds comprise biocompatible polymers. In several embodiments, the scaffolds comprise one or more saccharide units and/or are polysaccharides. In several embodiments, the scaffolds comprise one or more chitosan, hyaluronic acid (HA), carboxymethylcellulose (CMC), hydroxyethyl cellulose, methyl cellulose, cellulose, alginate (including 1,4-linked α-1-guluronic acid (G) and β-d-mannuronic acid (M) units), collagen, gelatin, cyclodextrin (e.g., having 5 (α), 6 (β), 7 (γ), or more α-D-glucopyranosides), aminoglycosides (e.g., kanamycin, streptomycin, tobramycin, gentamicin, neomycin, etc.), elastin, repeat units thereof, structural units thereof, or combinations thereof. In several embodiments, one or more polymers are crosslinked to form the scaffold. In several embodiments, the polymers are not crosslinked to form the scaffold. In several embodiments, the scaffolds allow the efficient reduction in viability and/or eradication of microbes (e.g., prokaryotic cells, bacteria, protozoa, fungi, algae, amoebas, slime molds, etc. and in particular such microbes that have developed at least some degree of drug resistance) with low toxicity native tissue and patient cells (e.g., eukaryotic cells, mammalian cells, human cells, etc.).

Unless otherwise defined, all technical and scientific terms used herein have the same meaning as commonly understood by one of ordinary skill in the art to which this subject matter belongs. The terminology used in the description of the subject matter herein is for the purpose of describing particular embodiments only and is not intended to be limiting of the subject matter.

The term "effective amount," as used herein, refers to that amount of a recited compound that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In some embodiments, an improvement in a condition can be a reduction in infection. In some embodiments, an improvement can be reduction of bacterial load (e.g., bioburden) on a surface or in a subject. Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including, but not limited to, the activity of the composition, formulation, route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are contemplated herein.

The term "biopolymer" refers to a polymeric substance occurring in living organisms, including polynucleotides (e.g., DNA, RNA), polysaccharides (e.g., cellulose), proteins (e.g., polypeptides), glycopeptides, peptidoglycans, and the like.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, curing the illness, etc.

The terms "disrupting" and "eradicating" refer to the ability of the presently disclosed structures to combat biofilms. The biofilms may be partially eradicated or disrupted, meaning that the cells no longer attach to one another or to a surface. The biofilm may be completely eradicated, meaning that the biofilm is no longer an interconnected, cohesive, or continuous network of cells to a substantial degree.

The terms "nitric oxide donor" or "NO donor" refer to species and/or molecules that donate, release and/or directly or indirectly transfer a nitric oxide species, and/or stimulate the endogenous production of nitric oxide in vivo and/or elevate endogenous levels of nitric oxide in vivo such that the biological activity of the nitric oxide species is expressed at the intended site of action.

The terms "nitric oxide releasing" or "nitric oxide donating" refer to species that donate, release and/or directly or indirectly transfer any one (or two or more) of the three redox forms of nitrogen monoxide (NO+, NO−, NO (e.g., xNO)) and/or methods of donating, releasing and/or directly or indirectly transferring any one (or two or more) of the three redox forms of nitrogen monoxide (NO+, NO−, NO). In some embodiments, the nitric oxide releasing is accomplished such that the biological activity of the nitrogen monoxide species is expressed at the intended site of action.

The term "microbial infection" as used herein refers to bacterial, fungal, viral, yeast infections, as well other microorganisms, and combinations thereof.

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), monkeys, etc. Human subjects include neonates, infants, juveniles, adults and geriatric subjects. The subject "in need of" the methods disclosed herein can be a subject that is experiencing a disease state and/or is anticipated to experience a disease state, and the methods and compositions of the invention are used for therapeutic and/or prophylactic treatment.

For the general chemical formulas provided herein, if no substituent is indicated, a person of ordinary skill in the art will appreciate that the substituent is hydrogen. A bond that is not connected to an atom, but is shown, indicates that the position of such substituent is variable. A jagged line, wavy line, two wavy lines drawn through a bond or at the end of a bond indicates that some additional structure is bonded to that position. For a great number of the additional monomers disclosed herein, but not explicitly shown in structures, it is understood by those in the art of polymers, that these monomers can be added to change the physical properties of the resultant polymeric materials even where the elemental analysis would not indicate such a distinction could be expected. Such physical properties include solubility, charge, stability, cross-linking, secondary and tertiary structure, and the like. Moreover, if no stereochemistry is indicated for compounds having one or more chiral centers, all enantiomers and diastereomers are included. Similarly, for a recitation of aliphatic or alkyl groups, all structural isomers thereof also are included. Unless otherwise stated, groups shown as $A_1$ through $A_n$ and referred to herein as an alkyl group, in the general formulas provided herein are independently selected from alkyl or aliphatic groups, particularly alkyl having 20 or fewer carbon atoms, and even more typically lower alkyl having 10 or fewer atoms, such as methyl, ethyl, propyl, isopropyl, and butyl. The alkyl may be optionally substituted (e.g., substituted or not substituted, as disclosed elsewhere herein). The alkyl may be a substituted alkyl group, such as alkyl halide (e.g. —$CX_3$ where X is a halide, and combinations thereof, either in the chain or bonded thereto), alcohols (i.e. aliphatic or alkyl hydroxyl, particularly lower alkyl hydroxyl) or other similarly substituted moieties such as amino-, amino acid-, aryl-, alkyl aryl-, alkyl ester-, ether-, keto-, nitro-, sulfhydryl-, sulfonyl-, sulfoxide modified-alkyl groups.

The term "amino" and "amine" refer to nitrogen-containing groups such as $NR_3$, $NH_3$, $NHR_2$, and $NH_2R$, wherein R can be as described elsewhere herein. Thus, "amino" as used herein can refer to a primary amine, a secondary amine, or a tertiary amine. In some embodiments, one R of an amino group can be a diazeniumdiolate (i.e., NONO).

Whenever a group is described as being "optionally substituted" that group may be unsubstituted or substituted with one or more of the indicated substituents. Likewise, when a group is described as being "unsubstituted or substituted" (or "substituted or unsubstituted") if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, haloalkoxy, an amino, a mono-substituted amine group, a di-substituted amine group, a mono-substituted amine(alkyl), a di-substituted amine(alkyl), a diamino-group, a polyamino, a diether-group, and a polyether-group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" or "$C_1$-$C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

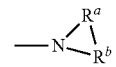

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by , followed by the number of carbon atoms, followed by a "*". For example

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. An alkylene group may be substituted or unsubstituted. For example, a lower alkylene group can be substituted by replacing one or more hydrogens of the lower alkylene group and/or by substituting both hydrogens on the same carbon with a $C_{3-6}$ monocyclic cycloalkyl group (e.g., 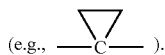 ).

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic (such as bicyclic) hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic (such as bicyclic) hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged, or spiro fashion. A cycloalkenyl group may be unsubstituted or substituted.

As used herein, "aryl" refers to a carbocyclic (all carbon) monocyclic or multicyclic (such as bicyclic) aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted. As used herein, "heteroaryl" refers to a monocyclic or multicyclic (such as bicyclic) aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "cycloalkyl(alkyl)" refer to an cycloalkyl group connected, as a substituent, via a lower alkylene group. The lower alkylene and cycloalkyl group of a cycloalkyl(alkyl) may be substituted or unsubstituted.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

As used herein, a "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N($R_A$)–" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N($R_A R_b$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "—$SO_2N(R_AR_b)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "nitro" group refers to an "—$NO_2$" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The terms "amino" and "unsubstituted amino" as used herein refer to a —$NH_2$ group.

A "mono-substituted amine" group refers to a "—$NHR_A$" group in which $R_A$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. The $R_A$ may be substituted or unsubstituted. A mono-substituted amine group can include, for example, a mono-alkylamine group, a mono-$C_1$-$C_6$ alkylamine group, a mono-arylamine group, a mono-$C_6$-$C_{10}$ arylamine group and the like. Examples of mono-substituted amine groups include, but are not limited to, —NH(methyl), —NH(phenyl) and the like.

A "di-substituted amine" group refers to a "—$NR_AR_B$" group in which $R_A$ and $R_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. $R_A$ and $R_B$ can independently be substituted or unsubstituted. A di-substituted amine group can include, for example, a di-alkylamine group, a di-$C_1$-$C_6$ alkylamine group, a di-arylamine group, a di-$C_6$-$C_{10}$ arylamine group and the like. Examples of di-substituted amine groups include, but are not limited to, N(methyl)$_2$, —N(phenyl)(methyl), —N(ethyl)(methyl) and the like.

As used herein, "mono-substituted amine(alkyl)" group refers to a mono-substituted amine as provided herein connected, as a substituent, via a lower alkylene group. A mono-substituted amine(alkyl) may be substituted or unsubstituted. A mono-substituted amine(alkyl) group can include, for example, a mono-alkylamine(alkyl) group, a mono-$C_1$-$C_6$ alkylamine($C_1$-$C_6$ alkyl) group, a mono-arylamine(alkyl group), a mono-$C_6$-$C_{10}$ arylamine($C_1$-$C_6$ alkyl) group and the like. Examples of mono-substituted amine(alkyl) groups include, but are not limited to, —$CH_2$NH(methyl), —$CH_2$NH(phenyl), —$CH_2CH_2$NH(methyl), —$CH_2CH_2$NH(phenyl) and the like.

As used herein, "di-substituted amine(alkyl)" group refers to a di-substituted amine as provided herein connected, as a substituent, via a lower alkylene group. A di-substituted amine(alkyl) may be substituted or unsubstituted. A di-substituted amine(alkyl) group can include, for example, a dialkylamine(alkyl) group, a di-$C_1$-$C_6$ alkylamine($C_1$-$C_6$ alkyl) group, a di-arylamine(alkyl) group, a di-$C_6$-$C_{10}$ arylamine($C_1$-$C_6$ alkyl) group and the like. Examples of di-substituted amine(alkyl)groups include, but are not limited to, —$CH_2$N(methyl)$_2$, —$CH_2$N(phenyl)(methyl), —$CH_2$N(ethyl)(methyl), —$CH_2CH_2$N(methyl)$_2$, —$CH_2CH_2$N(phenyl)(methyl), —$NCH_2CH_2$(ethyl)(methyl) and the like.

As used herein, the term "diamino-" denotes a "—N($R_A$)$R_B$—N($R_C$)($R_D$)" group in which $R_A$, $R_C$, and $R_D$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_B$ connects the two "N" groups and can be (independently of $R_A$, $R_C$, and $R_D$) a substituted or unsubstituted alkylene group. $R_A$, $R_B$, $R_C$, and $R_D$ can independently further be substituted or unsubstituted.

As used herein, the term "polyamino" denotes a "—(N($R_A$)$R_B$—)$_n$—N($R_C$)($R_D$)". For illustration, the term polyamino can comprise —N($R_A$)alkyl—N($R_A$)alkyl-N($R_A$)alkyl-N($R_A$)alkyl-H. In some embodiments, the alkyl of the polyamino is as disclosed elsewhere herein. While this example has only 4 repeat units, the term "polyamino" may consist of 1, 2, 3, 4, 5, 6, 7, 8, 9, or 10 repeat units. $R_A$, $R_C$, and $R_D$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_B$ connects the two "N" groups and can be (independently of $R_A$, $R_C$, and $R_D$) a substituted or unsubstituted alkylene group. $R_A$, $R_C$, and $R_D$ can independently further be substituted or unsubstituted. As noted here, the polyamino comprises amine groups with intervening alkyl groups (where alkyl is as defined elsewhere herein).

As used herein, the term "diether-" denotes an "—OR$z_B$O—R$_A$" group in which R$_A$ can be a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein R$_B$ connects the two "O" groups and can be a substituted or unsubstituted alkylene group. R$_A$ can independently further be substituted or unsubstituted.

As used herein, the term "polyether" denotes a repeating —(OR$_B$—)$_n$OR$_A$ group. For illustration, the term polyether can comprise —Oalkyl-Oalkyl-Oalkyl-Oalkyl-OR$_A$. In some embodiments, the alkyl of the polyether is as disclosed elsewhere herein. While this example has only 4 repeat units, the term "polyether" may consist of 1, 2, 3, 4, 5, 6, 7, 8, 9, or 10 repeat units. R$_A$ can be a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. R$_B$ can be a substituted or unsubstituted alkylene group. R$_A$ can independently further be substituted or unsubstituted. As noted here, the polyether comprises ether groups with intervening alkyl groups (where alkyl is as defined elsewhere herein and can be optionally substituted).

Where the number of substituents is not specified (e.g. haloalkyl), there may be one or more substituents present. For example, "haloalkyl" may include one or more of the same or different halogens. As another example, "C$_1$-C$_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

When a range of integers is given, the range includes any number falling within the range and the numbers defining ends of the range. For example, when the terms "integer from 1 to 20" is used, the integers included in the range are 1, 2, 3, 4, 5, 6, 7, 8, 9, 10, etc., up to and including 20.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount. The term "consists essentially of" (and grammatical variants), shall be given its ordinary meaning and shall also mean that the composition or method referred to can contain additional components as long as the additional components do not materially alter the composition or method. The term "consists of" (and grammatical variants), shall be given its ordinary meaning and shall also mean that the composition or method referred to is closed to additional components. The term "comprising" (and grammatical variants), shall be given its ordinary meaning and shall also mean that the composition or method referred to is open to contain additional components.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

Nitric Oxide Scaffolds

Nitric oxide, an endogenously produced diatomic free radical, is associated with numerous biological processes, including platelet aggregation and adhesion, vasodilation, wound repair, the immune response, the mediation of angiogenesis, and carcinogenesis. Deficiency of NO can lead to some degree of malfunction of NO-relevant physiological systems. Exogenous NO delivery may be an effective strategy for the resolution of biomedical therapies ranging from cardiovascular diseases, to antibacterial and anticancer therapies. NO delivery can also be used to achieve antimicrobial activity. However, the difficulty in delivering NO as a therapeutic warrants, in several embodiments, the use of assorted synthetic NO donors (e.g., N-diazeniumdiolates, S-nitrosothiols, metal nitrosyls, organic nitrates), in order to control NO delivery. N-diazeniumdiolates (NONOates) may be useful as NO donors because of their good stability and their capacity for proton-triggered NO delivery under physiological conditions. It has a relatively short biological half-life (seconds) and is reactive in nature. In several embodiments disclosed herein, the NO donor comprises any one of the following nitric oxide releasing moieties:

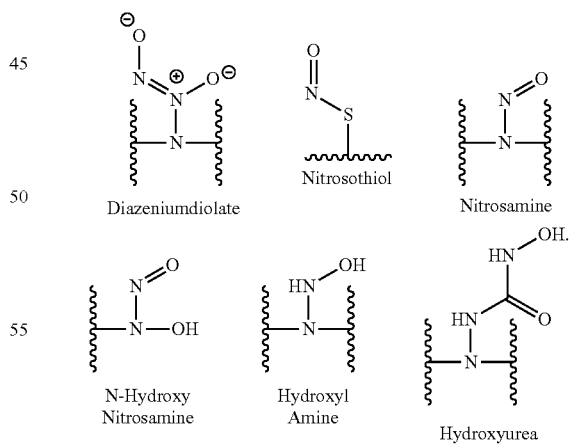

where "⌇" indicates attachment to other atoms within the structure (e.g., any instance of —H, —CH$_2$—, —CH—, etc.). In some embodiments, the NO donor is a N-diazeniumdiolate NO donor. In some embodiments, the NO donor is attached along a linear unit at a secondary amine as disclosed elsewhere herein.

The synthesis of scaffolds capable of controlled NO storage and release is important for taking advantage of NO's role in physiology and for developing NO-based therapeutics. In addition to the effects of NO disclosed above, NO is also a potent antibacterial agent that acts on bacteria via nitrosative and/or oxidative stress. NO is a broad-spectrum antibacterial agent and in some embodiments, scaffolds that deliver NO are capable of eradicating both bacteria and biofilms, primarily through the formation of reactive NO byproducts (e.g., peroxynitrite and dinitrogen trioxide) that cause oxidative and nitrosative damage to microbial DNA and/or membrane structures. Advantageously, the wide range of mechanisms by which NO exerts its antibacterial effects reduces the risk that bacteria will develop resistance. Thus, NO-releasing materials may be good targets to battle bacterial infection. The antibacterial efficacy of NO-releasing materials may be dependent on both NO payloads and associated release kinetics. In some instances, high NO total is an important parameter to effectively evaluate storage capability of good scaffolds. Additionally, in several embodiments disclosed herein, a high density of secondary amine groups imbues certain donors with a high NO storage capacity. However, NO release that is too fast and high NO storage may result in undesired toxicity to mammalian cells. Therefore, challenges exist in preparing biocompatible NO-releasing materials with high NO storage and low cytotoxicity, and such challenges, among others, are addressed according to several embodiments disclosed herein.

Several embodiments disclosed herein have one or more of the following advantages: efficient and unique synthesis routes and resultant chemical composition of polymer constructs. Controllable amounts of secondary-amines and diverse exterior terminal groups (e.g., hydroxyl, methyl, hydroxymethyl, and primary amine) can be provided. The NO storage and NO-release kinetics of the generated nitric-oxide releasing scaffolds can be tuned for a particular application. This tuning is achieved, in several embodiments, by altering the type and/or number of functionalized monomers of the formulae disclosed herein. In several embodiments, additional functionalization of the amines in the generated nitric-oxide releasing scaffolds, for example, by compounds with different compositions, further enables the control over NO-release kinetics. In some embodiments, the secondary amine group directly influences the stability of the N-diazeniumdiolate (or other NO carrier group), allowing for control over both NO storage and release kinetics.

As disclosed elsewhere herein, nitric oxide not only plays fundamental roles in several important biological processes, but also exhibits function as an antibacterial or anticancer agent. As disclosed elsewhere herein, various NO donors (e.g., N-diazeniumdiolates, S-nitrosothiols, metal nitrosyls, organic nitrates) can be used for controlled exogenous NO delivery. N-bound diazeniumdiolates are attractive because of their good stability and facile storage, which spontaneously undergo proton-triggered dissociation under physiological condition to regenerate the NO radicals. In several embodiments, progress has been made in preparing and testing biocompatible N-diazeniumdiolate-modified scaffolds, including those derived from biopolymers and saccharide derived polymers (e.g., chitosan, hyaluronic acid, CMC, etc.).

Unlike current treatments, NO, an endogenously produced free radical, eradicates bacteria using a variety of mechanisms, including, but not limited to, lipid peroxidation, nitrosation of membrane proteins, and DNA damage via reactive oxygen/nitrogen species (e.g., peroxynitrite, dinitrogen trioxide). Multiple biocidal mechanisms allow NO to significantly diminish the risk of fostering bacterial resistance. Furthermore, NO has the improved ability to actively degrade both the biofilm matrix and mucus structure, thus allowing for more efficient biocidal action and mucociliary clearance.

As disclosed elsewhere herein, some embodiments disclosed herein pertain to the use of polymer scaffolds to deliver NO to achieve microbicidal activity. In some embodiments, the polymer scaffold is derived from a biopolymer. In some embodiments, the scaffold and/or biopolymer is water soluble. In some embodiments, the scaffold and/or biopolymer is and/or is biodegradable. In several embodiments, the polymer scaffold is a hyperbranched structure, such as disclosed in U.S. Patent Application No. 62/737,603, which is incorporated by reference in its entirety for all purposes. In several embodiments, the scaffold is a viscosity enhancing agent.

In several embodiments, the scaffolds, polymers, mixtures of polymers, etc., have structural units (e.g., repeat units, etc.) along a chain of a polymer. In several embodiments, the one or more structural units is functionalized with one or more instances of each of $R_1$, $R_2$, $R_3$, $R_4$, $R_5$, and $R_6$. In several embodiments, each instance of $R_1$, $R_2$, $R_3$, $R_4$, $R_5$, and $R_6$ are independently selected from the group consisting of —OH, —NH$_2$, —OCH$_3$, —C(O)OH, —CH$_2$OH, —CH$_2$OCH$_3$, —CH$_2$OCH$_2$CH$_2$OH, —OCH$_2$C(O)O H, —CH$_2$OCH$_2$C(O)OH, —CH$_2$C(O)OH, —NHC(O)—CH$_3$, —C(O)O((CH$_2$)$_a$O)$_b$—H, —C(O)O((CH 2)$_a$O$_b$—(CH$_2$)$_i$H, —C(O)O(C$_{1-5}$alkyl), —C(O)—NH—((CH$_2$)$_d$NH)$_e$—H, —C(O)—NH—((CH$_2$)$_d$NH)$_e$—(CH$_2$)$_f$H, —C(O)—X$^1$—((CH$_2$)$_g$X$^2$)$_h$—(CH$_2$)$_i$H, —C(O)—X$^1$—((CH$_2$)$_g$X$^2$)$_h$((CH$_2$)$_j$X$^3$)$_k$—(CH$_2$)$_i$H, —O—((CH$_2$)$_a$O)$_b$—H, —O—((CH$_2$)$_a$O)$_b$—(CH$_2$)$_c$H, —O—(C$_{1-5}$alkyl), —NH—((CH$_2$)$_d$NH)$_e$—H, —NH—((CH$_2$)$_d$N H)$_e$—(CH$_2$)$_f$H, —X$^1$—((CH$_2$)$_g$X$^2$)$_h$—(CH$_2$)$_i$H, —X$^1$—((CH$_2$)$_g$X$^2$)$_h$((CH$_2$)$_j$X$^3$)$_k$—(CH$_2$)$_i$H, wherein each instance of a, b, c, d, e, f, g, h, i, j, k, and 1 is independently selected from an integer of 0, 1, 2, 3, 4, 5, 6, 7, 8, 9, or 10, wherein, each instance of X$^1$, X$^2$, and X$^3$ is independently selected from —O—, —S—, —NH—, C(O)NH—; and wherein at least one instance of X$^1$, X$^2$, and X$^3$ is represented by one of the following NO donating groups

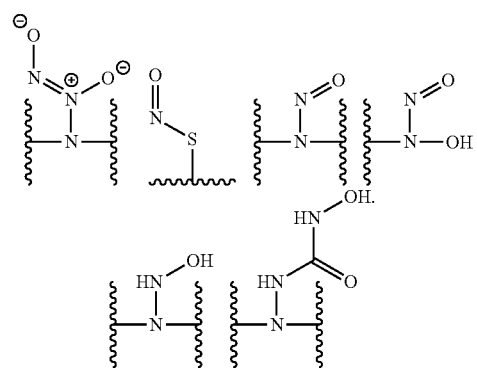

For instance, a non-derivatized polymer chain having one or more hydroxyl, amino, or carboxyl functional groups, can be functionalized and/or derivatized via those functional groups to add, for example, one or more of $R_1$, $R_2$, $R_3$, $R_4$, $R_5$, and $R_6$. Thus, the disclosed methods are applicable to any biocompatible polymer having one or more of these functional groups pendant from the polymer chain. In several embodiments, the polymer is a biopolymer. In several embodiments, the polymer is a biodegradable polymer. In several embodiments, the polymer is a polysaccharide. In several embodiments the polysaccharide comprises a polymer derived from chitosan, hyaluronic acid, carboxymethylcellulose, hydroxyethyl cellulose, methyl cellulose, cellulose, alginate, cyclodextrin, aminoglycosides, or other polysaccharide. In several embodiments the polysaccharide comprises one or more of the following structures:

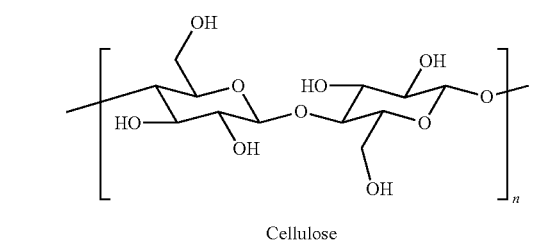

Cellulose

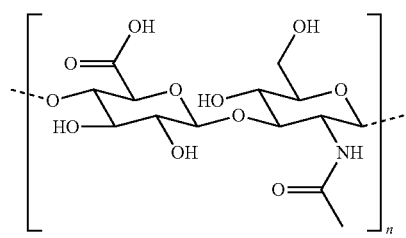

Hyaluronic Acid

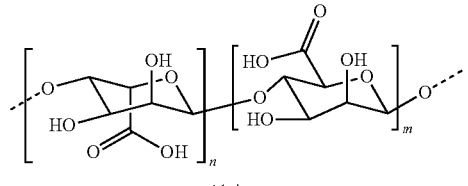

Alginate

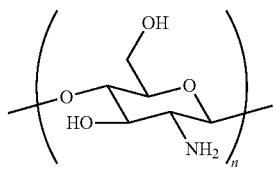

Chitosan

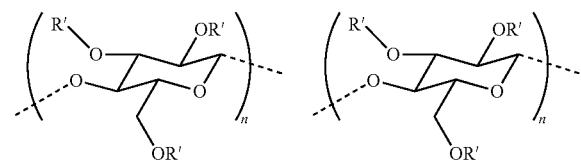

R' = H or CH$_2$COOH
Carboxymethylcellulose

R' = H or CH$_2$CO$_2$H
Hydroxyethylecellulose

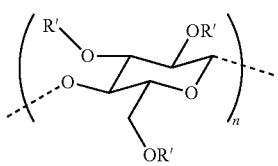

R' = H or CH$_3$
Methylcellulose

-continued

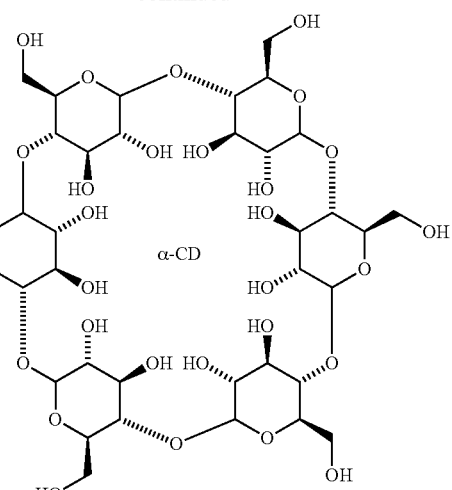

α-CD

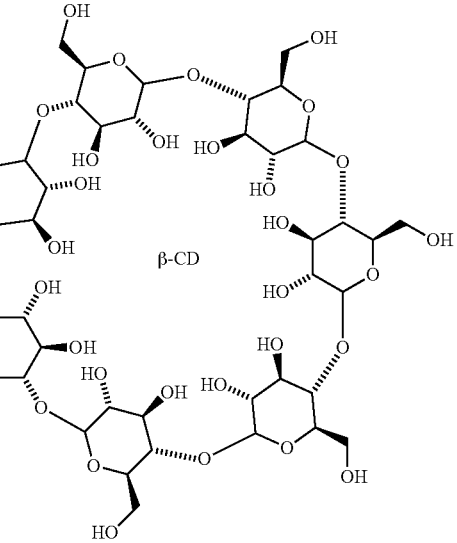

β-CD

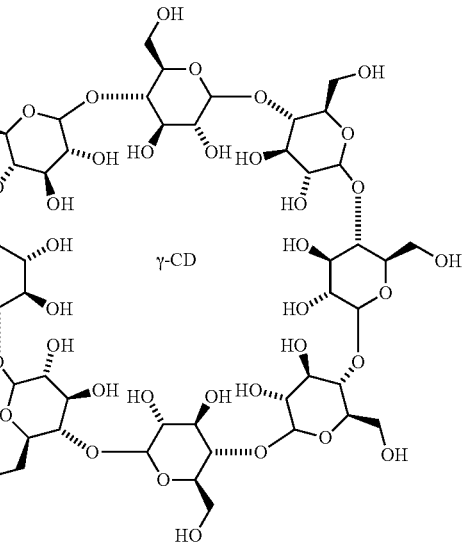

γ-CD

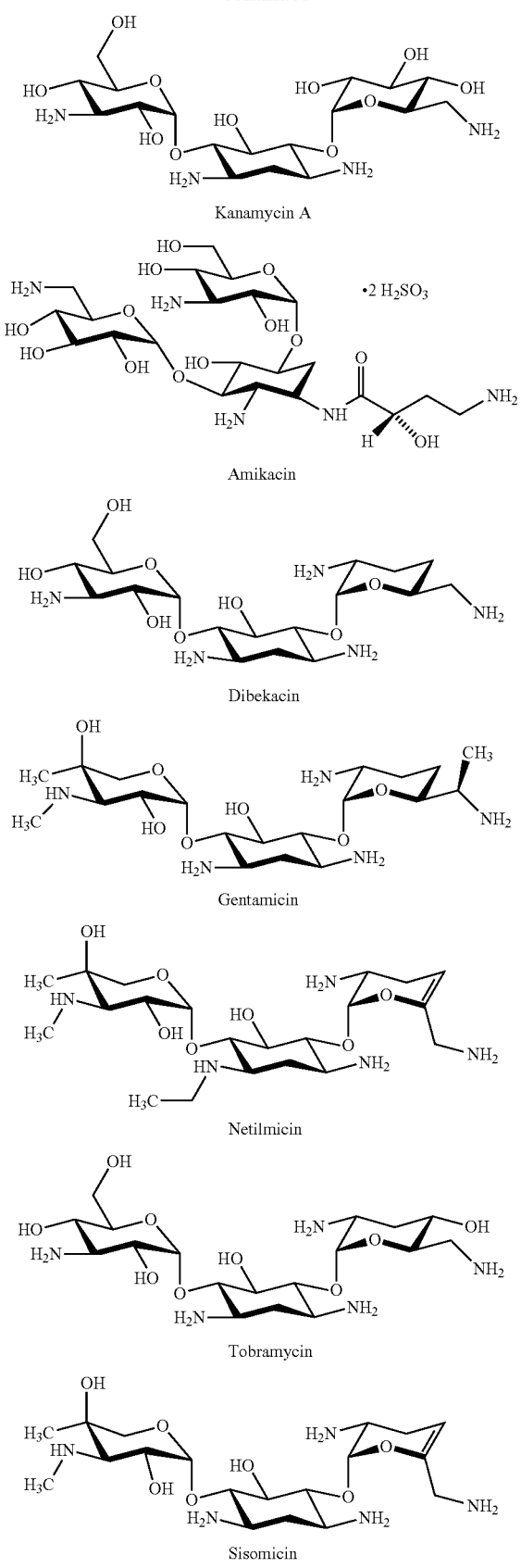

where any one or more of the hydroxyl, amino, or carboxyl functional groups shown above, can be functionalized or derivatized via those functional groups to add, for example, one or more of $R_1$, $R_2$, $R_3$, $R_4$, $R_5$, and $R_6$. In some embodiments, any one of the amino groups of an aminoglycoside could be functionalized with a linking unit (as disclosed in PCT/IB2018/052144, published as WO/2018/178902, which is hereby incorporated by reference in its entirety) to prepare a macromolecular structure.

In several embodiments, the scaffold and/or NO releasing polymer system comprises one or more structural units represented by Formula I:

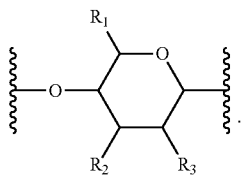

Formula I

In several embodiments, the structural unit represented by Formula I represents one or more of a saccharide unit of a cellulose polymer, a saccharide unit of a hyaluronic acid polymer, a saccharide unit of an alginate polymer, a saccharide unit of a chitosan polymer, a saccharide unit of a carboxymethylcellulose polymer, a saccharide unit of a hydroxyethylcellulose polymer, a saccharide unit of a methyl cellulose polymer, and/or a saccharide unit of a cyclodextrin ring structure. In several embodiments, Formula I has the stereochemical configuration shown in Formula I':

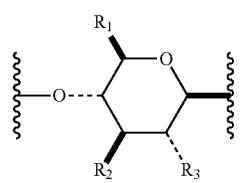

Formula I' and the polymer of the scaffold comprises carboxymethylcellulose.

In several embodiments, the scaffold and/or NO releasing polymer system comprises one or more structural units represented by Formula II:

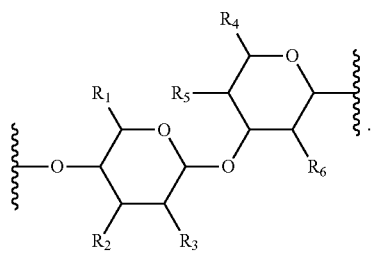

Formula II

In several embodiments, the structural unit represented by Formula I represents one or more of a saccharide unit of a cellulose polymer, a saccharide unit of a hyaluronic acid polymer, and/or a saccharide unit of an alginate polymer. In several embodiments, Formula II has the stereochemical configuration shown in Formula II':

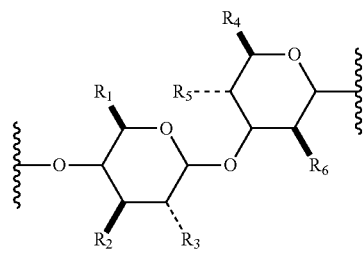

Formula II' and the polymer of the scaffold comprises hyaluronic acid.

In several embodiments, each instance of $R_1$, $R_2$, $R_3$, $R_4$, $R_5$, and $R_6$ is independently selected from the group consisting of:

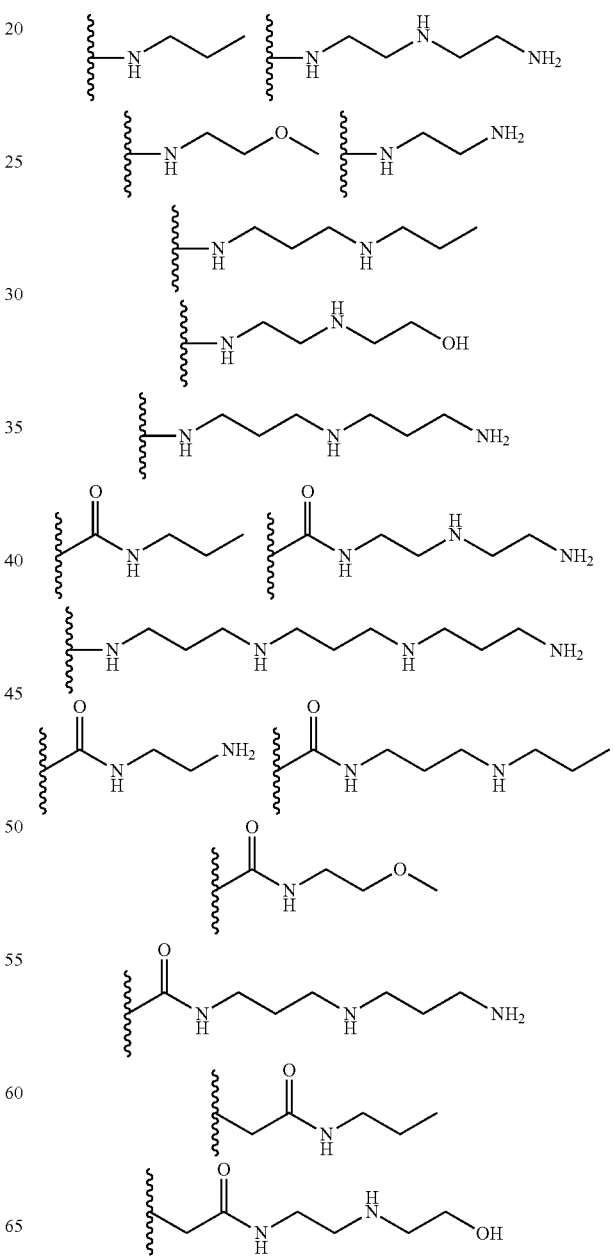

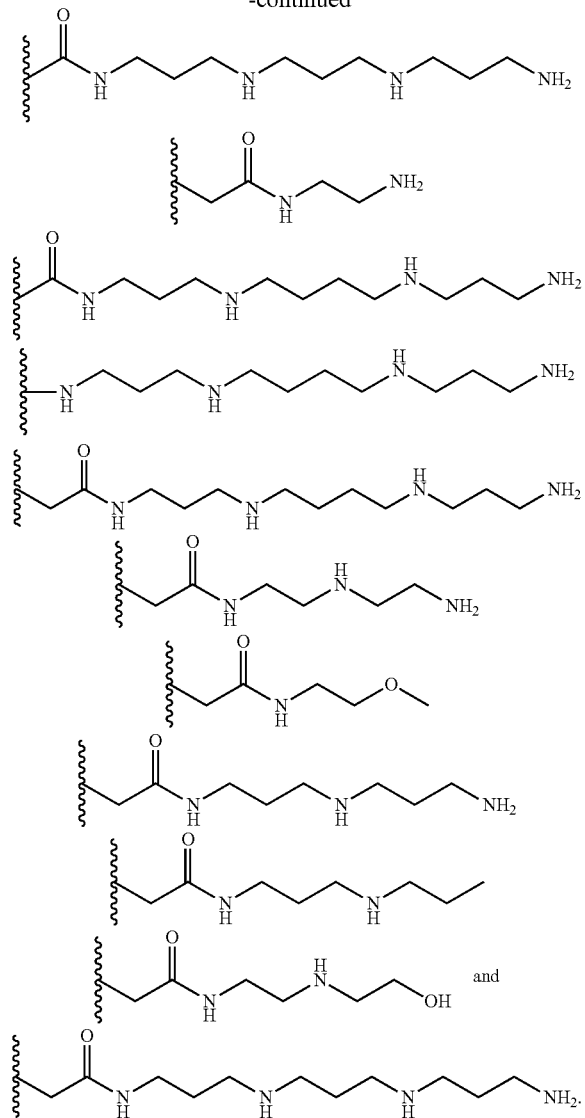

In some embodiments, any one of the secondary amines can be functionalized as an NO donating moiety, including, for example:

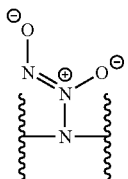

Properties

In several embodiments, various structural units (e.g., repeat units), functionalization of structural units (with various moieties), levels of crosslinking (if crosslinked), molecular weight, concentrations, or other chemical features of the disclosed scaffolds contribute to the tunability of the properties of the scaffolds disclosed herein. In several embodiments, by changing one or more of these features, one or more properties of the scaffolds can be tuned. In several embodiments, the NO release rate, antimicrobial effect, water solubility, degradation rate, viscosity, gel firmness (where the scaffold forms a gel), viscoelasticity, modulus, etc. are tunable.

In several embodiments, properties of the polymer and or composition prepared therefrom can be tuned by adjusting the molecular weight of the polymer used. In several embodiments, the weight-average molecular weight ($M_w$) in kDa of polymers disclosed herein are greater than or equal to about: 2.5, 5.0, 7.0, 10, 15, 30, 50, 100, 200, 500, 750, 1,000, 2,000, 10,000, or ranges including and/or spanning the aforementioned values. In several embodiments, the number-average molecular weight ($M_n$) in kDa of polymers disclosed herein are greater than or equal to about: 2.5, 5.0, 7.0, 10, 15, 30, 50, 90, 100, 200, 500, 700, 1,000, 2,000, 10,000, or ranges including and/or spanning the aforementioned values. In several embodiments, the polymers disclosed herein may have n repeat units. In several embodiments, n equal to or at least about: 10, 25, 50, 100, 250, 500, 1000, 2500, 5000, 10000, or ranges including and/or spanning the aforementioned values. In several embodiments, size exclusion chromatography (SEC) can be used to measure the molecular weight of the scaffold structures disclosed herein. In several embodiments, multi-angle light scattering (SEC-MALS) detectors can be used. In several embodiments, the scaffold structures can be characterized using their polydispersity index. The polydispersity index (PDI) is a measure of the distribution of molecular mass in a given polymer sample. PDI can be calculated by dividing the weight average molecular weight and the number average molecular weight. In several embodiments, the scaffold structures have a PDI of greater than or equal to about: 1.05, 1.1, 1.2, 1.3, 1.5, 1.7, 1.8, 1.9, 2.0, or ranges including and/or spanning the aforementioned values.

In several embodiments, the polymers (or mixtures of polymers) may be water soluble and/or mutually miscible. In several embodiments, the scaffolds are soluble in water (at about 20° C.) at a concentration of greater than or equal to about: 1 mg/ml, 10 mg/ml, 20 mg/ml, 50 mg/ml, 100 mg/ml, 200 mg/ml, 300 mg/ml, 400 mg/ml, 500 mg/ml, or ranges including and/or spanning the aforementioned values.

According to several embodiments, different NO carrying polymers can be combined to prepare aqueous solutions comprising concentrations equal to or at least about: 100 μg/mL, and can be higher, e.g. about 1 mg/ml, about 5 mg/ml, about 10 mg/ml, about 20/ml, or about 40 mg/ml or higher. The amount of the second polymer in the aqueous composition can be at least about 10% by weight, based on the weight of the first polymer, and may be higher, e.g., at least about 20% by weight, at least about 30% by weight, or at least about 50% by weight, same basis. The polymers in an aqueous composition are selected such the polymers are mutually miscible. As noted above, the first polymer with antimicrobial activity and the second polymer with antimicrobial activity are considered mutually miscible if at least about 90% of the polymeric components remain mutually soluble 24 hours after mixing and maintaining at room temperature in water at a concentration of each polymer of 1 mg/ml, upon visible examination. Surprisingly, such mutual miscibility of the water polymers can be achieved, despite an expectation of phase separation due to the typical mutual incompatibility of polymers in aqueous solution at the 1 mg/ml concentrations and molecular weights described herein. The aqueous compositions described herein can be prepared by intermixing the individual polymeric components with water, e.g., at room temperature with stirring.

In several embodiments, the polymers (or mixtures of polymers, etc.) disclosed herein have properties characteristic of a viscous fluid and/or of a gel. In several embodiments, the polymers (or mixtures of polymers, etc.) have a gelling point at room temperature (in water or PBS) at a concentration (in w/w %) of less than or equal to about: 0.5%, 1%, 2.5%, 5%, 10%, or ranges including and/or spanning the aforementioned values. In several embodiments, the polymers (or mixtures of polymers, etc.) may have a gelling point in water. In several embodiments, the polymers gel in water (at about 20° C.) at a concentration of greater than or equal to about: 0.5 mg/ml, 1 mg/ml, 10 mg/ml, 20 mg/ml, 50 mg/ml, 100 mg/ml, 250 mg/ml, or ranges including and/or spanning the aforementioned values. In several embodiments, at a concentration of 5% w/w solution, the polymers have a viscosity (in cPa·s at 20° C.) of equal to or at least about: 10, 50, 100, 1,000, 2,000, 5,000, 10,000, or ranges including and/or spanning the aforementioned values. In several embodiments, the polymers have an intrinsic viscosity of equal to or greater than about: 0.5 $m^3/kg$, 1.0 $m^3/kg$, 2.0 $m^3/kg$, 4.0 $m^3/kg$, 8.0 $m^3/kg$, or ranges including and/or spanning the aforementioned values.

In several embodiments, at a concentration of 5% w/w solution, the polymers have a firmness of equal to or at least about: 1.0 mN, 2.5 mN, 5 mN, 10 mN, 15 mN, 20 mN, 30 mN, 50 mN, or ranges including and/or spanning the aforementioned values. In several embodiments, at a concentration of 5% w/w solution, the polymers have a work of adhesion (in mN*mm) of equal to or at least about: 1.0, 2.5, 5, 10, 15, 20, 30, 50, 100, or ranges including and/or spanning the aforementioned values. In several embodiments, at a concentration of 5% w/w solution, the polymers have a storage modulus (G') in Pa of equal to or at least about: 250, 500, 1,000, 2,000, 4,000, 5,000, 10,000, or ranges including and/or spanning the aforementioned values. In several embodiments, at a concentration of 5% w/w solution, the polymers have an elastic modulus (G") in Pa of equal to or at least about: 25, 50, 100, 200, 400, 500, 1,000, 2,000, 5,000, 10,000, or ranges including and/or spanning the aforementioned values. In several embodiments, the aqueous composition is characterized by a barrier activity, as measured by a decrease in the diffusion rate of an anionic dye of more than 2 logs at a total scaffold concentration of 40 mg/ml or less.

In several embodiments, the gels are stable at a variety of temperatures 20° C. (e.g., 40° C., 45° C., 55° C., 60° C., 80° C., etc.) and are stable for prolonged storage periods (e.g., 10 hours, 20 hours, 22 hours, 25 hours, 30 hours, etc., days such as 1 day, 3 days, 5 days, 6 days, 7 days, 15 days, 30 days, 45 days, etc., weeks such as 1 week, 2 weeks, 3 weeks, 4 weeks, 6 weeks, 8 weeks, etc., months such as 1 month, 2 months, 3 months, 4 months, 5 months, 6 months, etc., or even years (1 year or greater)).

In several embodiments, the viscosity of the composition increases with increasing temperature, as described above. In several embodiments, the viscosity of the composition decreases with decreasing temperature. For example, if the composition is above the gelling temperature, then the composition has a relatively high viscosity, such as in the form of a gel. In several embodiments, if the composition is cooled to below the gelling temperature, then the composition decreases in viscosity, such as in the form of a liquid. In several embodiments, as such, the polymers as disclosed herein may be reversible polymers (e.g., thermoreversible polymers), where the transition from liquid to gel may be reversed upon exposure to appropriate conditions. For instance, as described above, compositions of the present disclosure include thermoreversible polymers, where the viscosity of the composition may be changed depending on the temperature of the composition. In several embodiments, the tunability of the viscosity enables a tailored composition profile upon delivery (e.g., more liquid at a delivery temperature and more viscous at, for example, body temperature).

In several embodiments, the polymers are characterized by a degree of swelling when exposed to water. In some embodiments, the swelling degree % of the polymers disclosed herein is equal to or at least about: 100, 250, 500, 1,000, 2,000, 5,000, or ranges including and/or spanning the aforementioned values. In other words, the polymers may swell or otherwise expand by 2×, 4×, 5×, 10×, 20×, 50×, 100×, or more.

In certain embodiments, the polymers disclosed herein have a gelling temperature similar to the normal body temperature of a subject, such as similar to human body temperature, or 37° C. By gelling temperature is meant the point on intersection between the plot for the elastic modulus and the plot for the viscous modulus. In some cases, if the composition is below the gelling temperature, then the composition has a relatively low viscosity, such as in the form of a liquid. In some instances, if the composition is above the gelling temperature, then the composition increases in viscosity (e.g., polymerizes), such that the composition is in the form of a gel. Compositions that transition from a liquid to a gel may facilitate administration of the composition to the subject, for example by facilitating injection of a low viscosity (e.g., liquid) composition at a temperature below the gelling temperature. After injection of the composition to the target treatment site, the temperature of the composition may increase due to absorption of heat from the surrounding body tissue, such that the composition increases in viscosity (e.g., transitions from a liquid to a gel, or polymerizes), thus providing structural and/or geometric support to the body tissue at the target treatment site. In some instances, gelling of the composition at the target treatment site may also facilitate retention of the composition at the treatment site by reducing the diffusion and/or migration of the composition away from the treatment site. In certain embodiments, the composition has a gelling temperature of 30° C. to 40° C., such as from 32° C. to 40° C., including from 35° C. to 40° C. In certain instances, the composition has a gelling temperature of 37° C.

In some embodiments, the methods disclosed herein provide NO-releasing polymers having NO storage capacities (in μmol NO/mg polymers) of greater than or equal to about: 0.25, 0.4, 0.5, 1.0, 1.5, 2.0, 3.0, or ranges including and/or spanning the aforementioned values. In some embodiments, within 2 h of being added to a PBS buffer solution as described in the Examples, the NO-releasing polymers, release greater than or equal to about: 25%, 50%, 75%, 85%, 90%, 95%, 100%, or ranges including and/or spanning the aforementioned values, their total wt % of bound NO. In several embodiments, NO release in use for reducing or eliminating a biofilm occurs in similar amounts, e.g., about 20-25%, about 30-50%, about 60-75%, at least 80%, at least 85%, at least 90%, at least 95%, ranges including and/or spanning the aforementioned values, of the total wt % of bound NO.

In some embodiments, the NO release may occur over a period of about 0.01 hours, 0.1 hours, 0.25 hours, 0.5 hours, 1 hour, 2 hours, 3 hours, 4 hours, 5 hours, 10 hours, 15 hours, 20 hours, 24 hours, 36 hours, 48 hours, 60 hours, or ranges including and/or spanning the aforementioned values. In several embodiments, the NO release half-life is equal to or at least about: 0.01 hours, 0.1 hours, 0.25 hours, 0.5 hours, 1 hour, 2 hours, 3 hours, 4 hours, 5 hours, 10 hours, 15 hours, 20 hours, 24 hours, 36 hours, 48 hours, 60 hours, or ranges including and/or spanning the aforementioned values. In some embodiments, the NO release occurs in less than or equal to about: 0.01 hours, 0.1 hours, 0.25 hours, 0.5 hours, 1 hour, 2 hours, 3 hours, 4 hours, 5 hours, 10 hours, 15 hours, 20 hours, 24 hours, 36 hours, 48 hours, 60 hours, or ranges including and/or spanning the aforementioned values. In some embodiments, nitrosamine is not present during NO release. As used herein the phrase "nitrosamine is not present" refers to levels of nitrosamine which are not detectable as determined by a UV-vis spectrum (or by other accepted methods in the art).

In some embodiments, the disclosed scaffolds and/or polymers of the disclosed compositions have a degradation rate per hour in an amylase enzyme exposure assay of less than or equal to about: 0.2%, 0.5%, 1.0%, 1.5%, 2.5%, 5.0%, 10%, or ranges including and/or spanning the aforementioned values.

In some embodiments, the disclosed functionalized NO-releasing polymers have antimicrobial activity. In some embodiments, the disclosed functionalized NO-releasing polymers provide greater than or equal to 90% bacterial reduction in a bacterial viability assay performed under static conditions over 2 hours against one or more of *P. aeruginos, S. aureus P. gingivalis, A. actinomycetemcomitans, A. viscosus*, and/or *S. mutans* at a polymer concentration of equal to or less than about: 8 mg/ml, 6 mg/ml, 4 mg/ml, 2 mg/ml, 1 mg/ml, 0.5 mg/ml, or ranges including and/or spanning the aforementioned values. In some embodiments, the disclosed functionalized NO-releasing polymers provide greater than or equal to 99% bacterial reduction and/or a 2 to 3 log reduction in a bacterial viability assay performed under static conditions over 2 hours against a gram positive bacteria at a polymer concentration of equal to or less than about: 8 mg/ml, 6 mg/ml, 4 mg/ml, 2 mg/ml, 1 mg/ml, 0.5 mg/ml, or ranges including and/or spanning the aforementioned values. In some embodiments, the disclosed functionalized NO-releasing polymers provide greater than or equal to 99% bacterial reduction and/or a 2 to 3 log reduction in a bacterial viability assay performed under static conditions over 2 hours against a gram negative bacteria at a polymer concentration of equal to or less than about: 8 mg/ml, 6 mg/ml, 4 mg/ml, 2 mg/ml, 1 mg/ml, 0.5 mg/ml, or ranges including and/or spanning the aforementioned values. In several embodiments, bacterial reduction is greater than 95%, greater than 98%, or greater than 99%.

Crosslinking

Cross-links are bonds that link one polymer chain to another (e.g., by covalent bonds or ionic bonds). In some embodiments, polymers capable of crosslinking generally exhibit branches off a main chain. In the presence of a crosslinking agent, such as a calcium cation, the negatively charged branches from the same or different chains are attracted to the positive cation. The branch joining chains together is referred to as a "crosslink." When polymer chains are linked together by crosslinks, they may lose some of their ability to move as individual polymer chains. For example, a liquid polymer (where the chains are freely flowing) can be turned into a "solid" or "gel" by crosslinking the chains together. This description applies when an anionic polymer such as sodium alginate is crosslinked with calcium chloride. The sodium alginate is able to be sustained in a solution, but the addition of calcium chloride causes the alginate chains to congregate or crosslink with the calcium cations, thereby forming an immobilized product. Other crosslinkers may also be used, depending on the embodiment. The generally immobilized product may also generally immobilize other materials that may be present such as active agents.

In some embodiments, crosslinks can be formed by chemical reactions that are initiated by heat, pressure, change in pH, or radiation. For example, mixing of an unpolymerized or partially polymerized resin with specific chemicals called crosslinking reagents can result in a chemical reaction that forms crosslinks. Crosslinking can also be induced in materials that are normally thermoplastic through exposure to a radiation source, such as electron beam exposure, gamma-radiation, or UV light. In some embodiments, the polymers disclosed herein can be crosslinked using salts with multiple charges or multifunctional compounds to covalently crosslink the structures (e.g., diamines, triamines, dicarboxylic acids, diepoxides, etc.).

Calcium chloride, a reagent used in some of the embodiments disclosed herein, provides an example of a simple ionic bond. When calcium (Ca) and chlorine (CO are combined, the calcium atoms each lose two electrons, forming cations ($Ca^{2+}$), and the chlorine atoms each gain an electron to form anions ($Cl^-$). These ions are then attracted to each other in a 1:2 ratio to form calcium chloride ($CaCl_2$). Other cation to anion ratios are also possible depending on the materials used. In some embodiments, calcium salts other than calcium chloride could be used as well as other suitable metals such as other multivalent cations. Similarly, alginates other than sodium alginate may be used such as potassium and ammonium alginates. Moreover, crosslinking could be used with materials (e.g., polysaccharides) other than alginate. In some embodiments, a material that electrostatically cross-links to form a suitable binding material for hemostatic applications can be used. In some embodiments, it may desirable to utilize converted alginate, i.e., a substance that is primarily calcium alginate with a partial sodium content, so that at least a portion of the alginate is water-soluble.

Hydrogels can be synthesized by cross-linking each polymer using an appropriate cross-linking agent chosen according to the chemical moieties present along the polysaccharide chains. In some embodiments, amine containing polymers can be crosslinked with carboxylic acid containing polymers by simple coupling reactions (e.g., with EDC, etc.). For instance, hyaluronic acid and carboxymethylcellulose hydrogels can be synthesized following the same chemical route, e.g., by exploiting the EDC chemistry: basically, an amide bond between the carboxylic groups of the polysaccharides and the primary amine of 1,3-diaminopropane (DAP)—the cross-linking agent—can be formed thanks to the presence of EDC. The cross-linking agent, DAP can be added to the mixture at a molar ratio of 0.5 with respect to the moles of carboxylic acid of the polymers and to EDC and NHS moles.

Compositions

In several embodiments, the polymers are administered as aqueous gels, e.g., topically. In several embodiments, the gels comprise one or more salts and are isotonic. In several embodiments, compositions can take the form of, for example, tablets or capsules prepared by a conventional technique with pharmaceutically acceptable excipients, such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a therapeutic agent can be formulated in combination with hydrochlorothiazide, and as a pH stabilized core having an enteric or delayed release coating which protects the therapeutic agent until it reaches the target organ.

In several embodiments, the composition includes two or more polymers with a certain ratio (w/w). In some cases, the ratio (w/w) is 1:10, or 1:9, or 1:8, or 1:7, or 1:6, or 1:5, or 1:4, or 1:3, or 1:2, or 1:1, or 2:1, or 3:1, or 4:1, or 5:1, or 6:1, or 7:1, or 8:1, or 9:1, or 10:1. For example, the ratio (w/w) may range from 1:1 to 10:1, such as 2:1 to 10:1, including 3:1 to 10:1, or 4:1 to 10:1, or 4:1 to 9:1, or 4:1 to 8:1, or 4:1 to 7:1, or 4:1 to 6:1. In certain embodiments, the ratio (w/w) is 5:1. These polymers can then be dissolved mutually in aqueous solution to provide a gel or solution. In several embodiments, each polymer of the mixture is provided at a concentration of less than or equal to about: 1 mg/ml, 10 mg/ml, 20 mg/ml, 50 mg/ml, 100 mg/ml, 250 mg/ml, or ranges including and/or spanning the aforementioned values.

Methods of Use

An unmet need in the area of wound healing, general surgery, and orthopedic surgery is for a antimicrobial material that can form a gel, that can release NO at a requisite rate, and that can degrade during a desired timeframe. This tailored degradation rate can be made to comport with the healing cycle of each specific condition and/or can comport to a time where the wound is at high risk of infection. Examples of these conditions include procedures such as hernia repair, diabetic foot ulcer healing, and orthopedic tendon repairs to name only a few. In several embodiments, the compounds and materials disclosed herein are targeted towards compositions that have tailorable degradation times.

Some embodiments provide a method for treating a tissue defect comprising positioning any of the polymers described herein at, over, or into the tissue defect. In several embodiments, the tissue defect is a wound. Several embodiments provide a method for treating a wound, for performing tissue repair, and/or for providing tissue and organ supplementation. In several embodiments, the first step of treating a tissue defect, wound, and/or supplementing and replacing tissue involves identifying a patient in need of an antimicrobial scaffold to aid in the remedying and healing of a tissue defect, healing of a wound, or in need of a tissue supplement.

A non-limiting list of patients in need of an antimicrobial scaffold includes patients suffering tissue defects. In several embodiments, the patients in need of an antimicrobial scaffold suffer from wounds including those from burns, skin ulcers, lacerations, bullet holes, animal bites, and other wounds prone to infection. Antimicrobial polymers can also be used in the treatment of diabetic foot ulcers, venous leg ulcers, pressure ulcers, amputation sites, in other skin trauma, or in the treatment of other wounds or ailments. Patients in need of an antimicrobial scaffold also include patients in need of repair and supplementation of tendons, ligaments, fascia, and dura mater. Degradable antimicrobial polymers can be used in supplement tissue in procedures including, but not limited to, rotator cuff repair, Achilles tendon repair, leg or arm tendon or ligament repair (e.g., torn ACL), vaginal prolapse repair, bladder slings for urinary incontinence, breast reconstruction following surgery, hernia repair, staple or suture line reinforcement, bariatric surgery repair, pelvic floor reconstruction, dural repair, gum repair, bone grafting, and reconstruction. Further, a patient in need of an antimicrobial scaffold also includes one in need of tissue or organ replacement. In several embodiments, the antimicrobial polymers described herein can be used as fillers and/or to supplement and/or replace tissue by acting as an artificial extracellular matrix. In such an application, an antimicrobial scaffold can be used to support cell and tissue growth. Briefly, cells can be taken from a patient or a viable host and seeded on an antimicrobial scaffold either in vivo or ex vivo. Then as the patient's natural tissues invade the material, it is tailored to degrade and leave only naturally occurring tissues and cells free of bacterial infection.

In several embodiments, applications also include delivery of therapeutic molecules to a localized site, use as adhesives or sealants, and as viscosupplements, and in wound healing, among others. The stabilized compositions may also be used as tissue fillers, dermal fillers, bone fillers, bulking agents, e.g., as a urethral or an esophageal bulking agent, and embolic agents as well as agents to repair cartilage defects/injuries and agents to enhance bone repair and/or growth. In several embodiments, an antimicrobial scaffold can be placed in or on a patient in, for example, a void space to fill the space.

In several embodiments, provided are polymers for repairing an injured tissue. In several embodiments, the composition is formulated for administration to a target treatment site in a subject. For example, the composition may be formulated to facilitate administration to a damaged or infected tissue in a subject.

In several embodiments, after administration of the composition (e.g., the antimicrobial scaffold), the composition may increase in temperature due to absorption of heat from surrounding body tissue of the subject. In several embodiments, the body temperature of the subject is sufficient to cause the composition to increase in viscosity (e.g., transition from a liquid to a gel. In several embodiments, the increase in viscosity (e.g., gelling) may give rise to a 3-dimensional network sufficient to provide structural and/or geometric support to a body tissue, such as a cardiac tissue (e.g., a cardiac tissue of an infarct region). In several embodiments, a syringe or catheter may be used to inject the composition in vivo. In several embodiments, the composition may be injected directly to the treatment site, or may be allowed to partially pre-heat in the syringe in order to increase the viscosity of the composition prior to injection. In several embodiments, a pre-heated formulation may reduce the possibility that a less viscous composition may diffuse and/or migrate away from the tissue area of interest after injection.

Dental caries (e.g., tooth decay) is another important disease state that affects 60%-70% school age children and the majority of adults in most industrialized countries. Worldwide, 11% of the total population suffers from severe periodontitis, which contributes to tooth loss and systematic diseases such as coronary, cardiovascular, stroke, and adverse pregnancy outcomes. Of >700 microorganisms in the oral cavity, cariogenic bacteria (e.g., *Streptococcus mutans, Actinomyces viscosus*) and periodontal pathogens (e.g., *Porphyromonas gingivalis, Aggregatibacter actinomycetemcomitans*) play a major role in the initiation and progression of oral diseases. Oral disease is among the most prevalent health problems faced by humans. Gram-positive cariogenic (e.g., *Streptococcus mutans, Actinomyces viscosus*) and Gram-negative periodontal (e.g., *Porphyromonas gingivalis, Aggregatibacter actinomycetemcomitans*) bacteria represent the main aggravators associated with the evolution and progression of dental caries and periodontal disease, respectively. Unfortunately, current treatments to combat these pathogens come with undesirable side effects.

For example, the systemic use of antibiotics may result in gastrointestinal disturbance and foster bacterial resistance. Chlorhexidine, a common oral antiseptic, can alter taste, stain teeth and tongue, and irritate buccal mucosa. Macromolecule NO-delivering vehicles (e.g., silica nanoparticles, gold, etc.) kill Gram-negative periodontal pathogens. However, these materials have not been demonstrated to kill Gram-positive cariogenic bacteria at a safe concentration (e.g., a concentration that is bacteriocidal but non-toxic towards mammalian cells). Similar with those nanomaterials, the lack of biodegradability and potential cytotoxicity of the silica nanoparticles also hinders their future for biomedical application. Current research also focuses on utilizing nanomaterials including silver, gold, zinc, and copper, as replacement for traditional antibiotics that suffered from fostering bacterial resistance. However, these nanomaterials may accumulate inside the body and may cause accumulative toxicity, limiting their future for certain applications. Developing oral therapeutics that are capable of killing those disease-causing bacteria is important to maintain a healthy oral cavity. In several embodiments, the structures disclosed herein (e.g., NO scaffolds and/or polymers), resolve one or more of these issues or others.

In several embodiments, the compositions disclosed herein may be used as eye drop formulations (e.g., artificial tears). In several embodiments, the composition comprises from about 0.1% to about 1.0% of the scaffold (or at a concentration as disclosed elsewhere herein). In several embodiments, the mixture comprises more than one type of polymer scaffold (e.g., HA-derived scaffolds and CMC-derived scaffolds) with the second polymer scaffold being present in an amount of 0.05% to about 0.15% (or at a concentration as disclosed elsewhere herein).

Cystic fibrosis (CF) is a genetic disorder characterized by poor mucociliary clearance and chronic bacterial infections. As shown herein, in several embodiments, nitric oxide (NO) has broad spectrum antibacterial activity against CF-relevant bacteria, making it an attractive alternative to traditional antibiotics. Treatment with NO limits bacterial resistance due to its multiple biocidal mechanisms (e.g., induction of nitrosative and oxidative stress). It has surprisingly been found that by storing NO on a scaffold using one of the disclosed designs, bactericidal efficacy is improved and systemic cytotoxicity is reduced. Treatments are effective against planktonic and biofilm-based pathogens, and cytotoxicity assays against mammalian lung cells demonstrate little harm to a treated subject's cells.

CF is a debilitating disease characterized by chronic bacterial infection of the lungs, resulting in life expectancies as low as two decades. A genetic defect in the CF transmembrane conductance regulator (CFTR) impedes the normal transport of ions (e.g., $Cl^-$) to the airway surface liquid, inhibiting water transport. As such, the airway epithelium dehydrates, creating thickened mucus that can no longer be efficiently cleared via mucociliary clearance mechanisms. As goblet cells continually excrete mucins into the dehydrated airway, mucus accumulation is accelerated to the point where the cilia become damaged, or nonfunctional, and are unable to clear mucus from the airway. Planktonic bacteria thrive in this static environment, promoting the formation of complex communities of pathogenic bacteria known as biofilms. The exopolysaccharide matrix produced by these biofilms inhibits oxygen diffusion, creating pockets of anaerobic environments and altering bacterial metabolism. This combination of a concentrated mucus layer and robust biofilms severely decreases the antibacterial efficacy of common CF therapies.

In several embodiments, the microbial load to be reduced and/or eliminated comprises drug-resistant bacteria. In several embodiments, the drug-resistant bacteria comprise carbapenem-resistant Enterobacteriaceae. In several embodiments, the drug-resistant bacteria comprise Methicillin-resistant *Staphylococcus aureus*. In several embodiments, the microbe comprises human immunodeficiency virus, herpes simplex virus, papilloma virus, parainfluenza virus, influenza, hepatitis, Coxsackie Virus, herpes zoster, measles, mumps, rubella, rabies, pneumonia, (hemorrhagic viral fevers, H1N1, and the like), prions, parasites, fungi, mold, yeast and bacteria (both gram-positive and gram-negative) including, among others, *Candida albicans, Aspergillus niger, Escherichia coli (E. coli), Pseudomonas aeruginosa (P. aeruginosa,* and *Staphylococcus aureus (S. aureus),* Group A streptococci, *S. pneumoniae, Mycobacterium tuberculosis, Campylobacter jejuni, Salmonella, Shigella, P. gingivalis, A. actinomycetemcomitans, A. viscosus,* and/or *S. mutans* and a variety of drug resistant bacteria. The terms microorganism and microbe shall be used interchangeably. Microbes can include wild-type, genetically-engineered or modified organisms. In several embodiments, the formulations and methods disclosed herein are for topical use or treatment of a surface, such as the oral mucosa.

In some embodiments, the scaffolds and/or compositions thereof may be administered by direct injection or application to, for example, an injured tissue. Suitable routes also include injection or application to a site adjacent to the injured tissue. Administration may include parenteral administration (e.g., intravenous, intramuscular, or intraperitoneal injection), subcutaneous administration, administration into vascular spaces, and/or administration into joints (e.g., intra-articular injection). Additional routes of administration include intranasal, topical, vaginal, rectal, intrathecal, intraarterial, and intraocular routes. In several embodiments, the scaffolds and compositions disclosed herein can be applied as a gel to a site of treatment. In several embodiments, the scaffolds and compositions can be applied as a liquid.

In several embodiments, liquid preparations for oral or topical administration can take the form of, for example, solutions, syrups or suspensions, or they can be presented as a dry product for constitution with water or another suitable vehicle before use. Such liquid preparations can be prepared by conventional techniques with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations also can contain buffer salts, flavoring, coloring and sweetening agents as appropriate. Preparations for oral administration can be suitably formulated to give controlled release of the active compound. For buccal administration the compositions can take the form of tablets or lozenges formulated in a conventional manner.

In several embodiments, the disclosed compounds also can be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds also can be formulated in rectal compositions (e.g., suppositories or retention enemas containing conventional suppository bases, such as cocoa butter or other glycerides), creams or lotions, or transdermal patches.

Pharmaceutical formulations also are provided which are suitable for administration as an aerosol by inhalation. In several embodiments, the polymer structures described herein are formulated in solution and/or aerosol form. In several embodiments, these formulations comprise a solution or suspension of a polymers described herein. In several embodiments, the desired formulation can be placed in a small chamber and nebulized. Nebulization can be accomplished by compressed air or by ultrasonic energy to form a plurality of liquid droplets or solid particles comprising the NO-releasing hyperbranched polyamidomines. For example, the presently disclosed NO-releasing hyperbranched polyamidomines can be administered via inhalation to treat bacterial infections related to cystic fibrosis. Cystic fibrosis-related bacterial infections include, but are not limited to stenotrophomonis, Mybacterium avium intracellulaire and *M. abcessus, Burkhoderia cepacia* and *Pseudomonas aeruginosa* (*P. aeruginosa* infections.

The subject matter described herein is directed to the following embodiments:

1. An NO releasing carboxymethylcellulose-derived polymer compound, comprising a unit structure of Formula I:

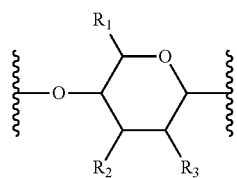

Formula I wherein $R_1$, $R_2$, and $R_3$ are independently selected from the group consisting of —OH, —CH$_2$OH, —OCH$_2$C(O)OH, —CH$_2$OCH$_2$C(O)OH, —C(O)—O—((CH$_2$)$_a$O)$_b$—H, —C(O)—O—((CH$_2$)$_a$O)$_b$—(CH$_2$)$_c$H, —C(O)—O—(C$_{1-5}$alkyl), —C(O)—NH—((CH$_2$)$_d$NH)$_e$—H, —C(O)—NH—((CH$_2$)$_d$NH)$_e$—(CH$_2$)$_f$H, —CH$_2$C(O)—NH—((CH$_2$)$_d$NH)$_e$—H, —CH$_2$C(O)—NH—((CH$_2$)$_d$NH)$_e$—(CH$_2$)$_f$H, —C(O)—X$^1$—((CH$_2$)$_g$X$^2$)$_h$—(CH$_2$)$_i$H, —CH$_2$C(O)—X$^1$—((CH$_2$)$_g$X$^2$)$_h$—(CH$_2$)$_i$H, —C(O)—X$^1$—((CH$_2$)$_g$X$^2$)$_h$((CH$_2$)$_j$X$^3$)$_k$—(CH$_2$)$_l$H, —O—((CH$_2$)$_a$O)$_b$—H, —O—((CH$_2$)$_a$O)$_b$—(CH$_2$)$_c$H, —O—(C$_{1-5}$alkyl), —NH—((CH$_2$)$_d$NH)$_e$—H, —NH—((CH$_2$)$_d$NH)$_e$—H, —NH—((CH$_2$)$_d$NH)$_e$—(CH$_2$)$_f$H, —X$^1$—((CH$_2$)$_g$X$^2$)$_h$—(CH$_2$)$_i$H, —X$^1$—((CH$_2$)$_g$X$^2$)$_h$((CH$_2$)$_j$X$^3$)$_k$—(CH$_2$)$_l$H, —CH$_2$C(O)—X$^1$—((CH$_2$)$_g$X$^2$)$_h$((CH$_2$)$_j$X$^3$)$_k$—(CH$_2$)$_l$H;

each instance of a, b, c, d, e, f, g, h, i, j, k, and l is independently selected from an integer of 0, 1, 2, 3, 4, 5, 6, 7, 8, 9, or 10;

each instance of X$^1$, X$^2$, and X$^3$ is independently selected from —O—, —S—, —NH—, C(O)NH—;

at least one of X$^1$, X$^2$, and X$^3$ is represented by one of the following:

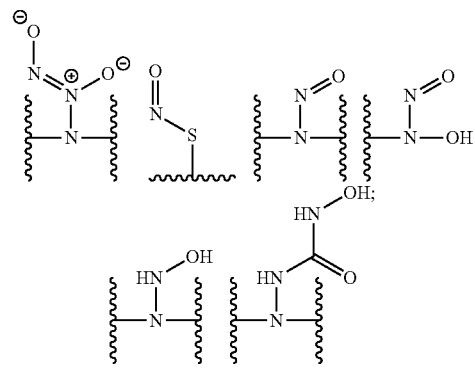

and wherein the compound has a viscosity of equal to or at least about 10 mPa·s at 20° C. at a concentration of 5% w/w in water.

2. The compound of embodiment 1, wherein Formula I has the stereochemical configuration shown in Formula I':

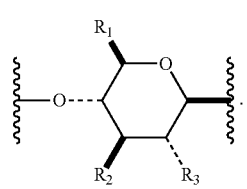

Formula I'

3. The compound of embodiments 1 or 2, wherein at least one of X$^1$, X$^2$, and X$^3$ is represented by the following:

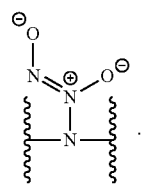 [SMILES: *N(*)/[N+]([O-])=N/[O-]]

4. The compound of any one of embodiments 1 to 3, wherein R$^1$ is —CH$_2$C(O)—X$^1$—((CH$_2$)$_g$X$^2$)$_h$((CH$_2$)$_j$X$^3$)$_k$—(CH$_2$)$_l$H.

5. The compound of any one of embodiments 1 to 4, wherein R$_2$ and R$_3$ are —OH.

6. The compound of any one of embodiments 1 to 5, wherein one or more of R$_1$, R$_2$, and R$_3$ are independently selected from the group consisting of:

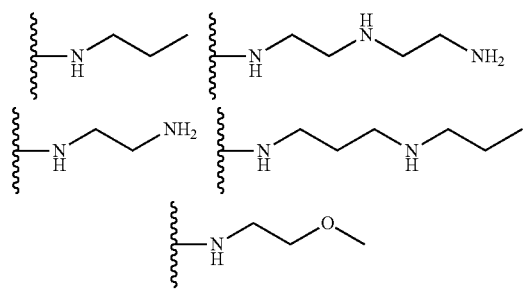

-continued

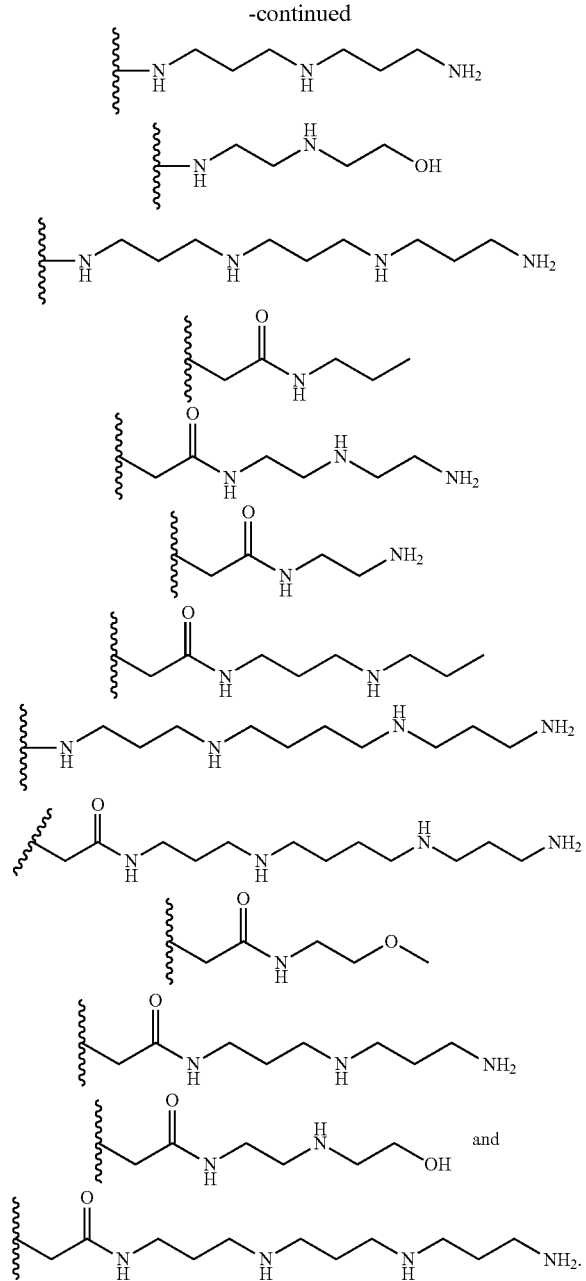

7. The compound of any one of embodiments 1 to 6, wherein the compound has a viscosity of equal to or at least about 20 mPa·s at 20° C. at a concentration of 20% w/w in water.

8. The compound of any one of embodiments 1 to 7, wherein the compound is soluble in water at a concentration of 50 mg/ml.

9. The compound of any one of embodiments 1 to 8, wherein the compound has a total releasable NO storage in a range of 0.1-1.0 µmol of NO per mg of compound.

10. The compound of any one of embodiments 1 to 9, wherein the compound has a NO half-life in the range of 0.1-24 hours.

11. The compound of any one of embodiments 1 to 8, wherein the compound has a total duration of NO release in the range of 1-60 hours.

12. The compound of any one of embodiments 1 to 8, wherein the total NO release after 4 hours is in the range between 0.1-1.0 µmol of NO per mg of compound.

13. The compound of any one of embodiments 1 to 12, wherein more than 15% of the repeat units in the compound are monomers of Formula I.

14. The compound of any one of embodiments 1 to 13, wherein the compound has a molecular weight in the range of about 90 kDa and about 700 kDa.

15. The compound of any one of embodiments 1 to 14, wherein the compound comprises two or more different covalently modified monomers of Formula I.

16. An NO releasing hyaluronic acid-derived polymer compound, comprising a unit structure of Formula II:

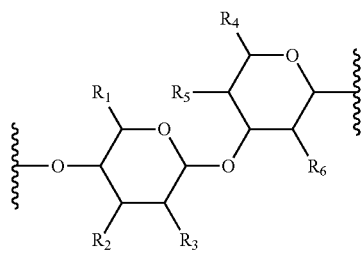

Formula II wherein
$R_1$, $R_2$, $R_3$, $R_4$, $R_5$, and $R_6$ are independently selected from the group consisting of of —OH, —NH$_2$, —CH$_2$OH, —C(O)OH, —NHC(O)—CH$_3$, —O—((CH$_2$)$_a$O)$_b$—H, —O—((CH$_2$)$_a$O)$_b$—(CH$_2$)$_c$H, —O—(C$_{1-5}$alkyl), —NH—((CH$_2$)$_d$NH)$_e$—H, —NH—((CH$_2$)$_d$NH)$_e$—(CH$_2$)$_f$H, —X$^1$—((CH$_2$)$_g$X$^2$)$_h$—H, —X$^1$—((CH$_2$)$_g$X$^2$)$_h$—(CH$_2$)$_i$H, —CH$_2$C(O)—X$^1$—((CH$_2$)$_g$X$^2$)$_h$((CH$_2$)$_j$X$^3$)$_k$—(CH$_2$)$_l$H, and —X$^1$—((CH$_2$)$_g$X$^2$)$_h$((CH$_2$)$_j$X$^3$)$_k$—(CH$_2$)$_l$H;

each instance of a, b, c, d, e, f, g, h, i, j, k, and l is independently selected from an integer of 0, 1, 2, 3, 4, 5, 6, 7, 8, 9, or 10;

each instance of X$^1$, X$^2$, and X$^3$ is independently selected from —O—, —S—, —NH—, C(O)NH—;

at least one of X$^1$, X$^2$, and X$^3$ is represented by one of the following:

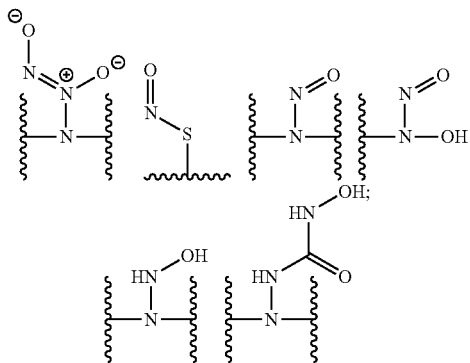

and
wherein the compound has a viscosity of equal to or at least about 10 mPa·s at 20° C. at a concentration of 5% w/w in water.

17. The compound of embodiment 16, wherein Formula II has the stereochemical configuration shown in Formula II':

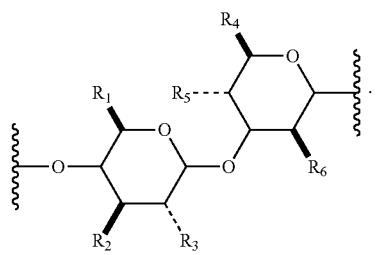

Formula II'

18. The compound of embodiments 16 or 17, wherein at least one of $X^1$, $X^2$, and $X^3$ is represented by one of the following:

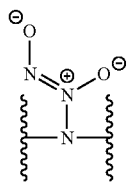

19. The compound of any one of embodiments 16 to 18, wherein $R^1$ is —$CH_2C(O)$—$X^1$—$((CH_2)_gX^2)_h$ $((CH_2)_jX^3)_k$—$(CH_2)_iH$.

20. The compound of any one of embodiments 16 to 19, wherein $R_2$ and $R_3$ are —OH.

21. The compound of any one of embodiments 16 to 20, wherein one or more of $R_1$, $R_2$, $R_3$, $R_4$, $R_5$, $R_6$ are independently selected from the group consisting of:

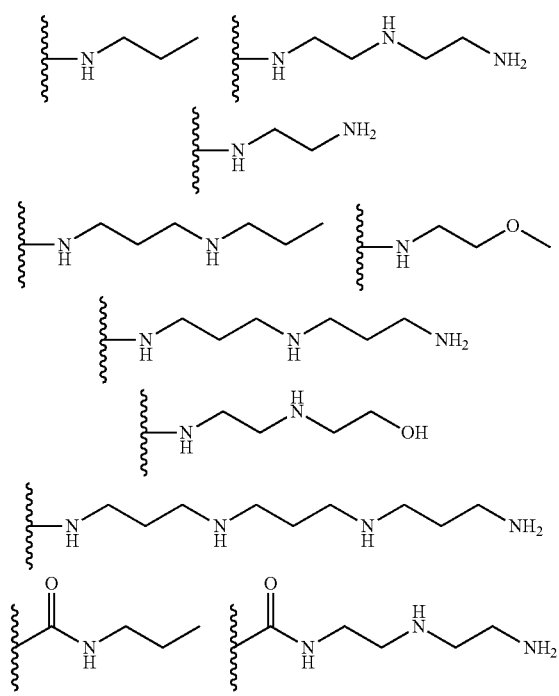

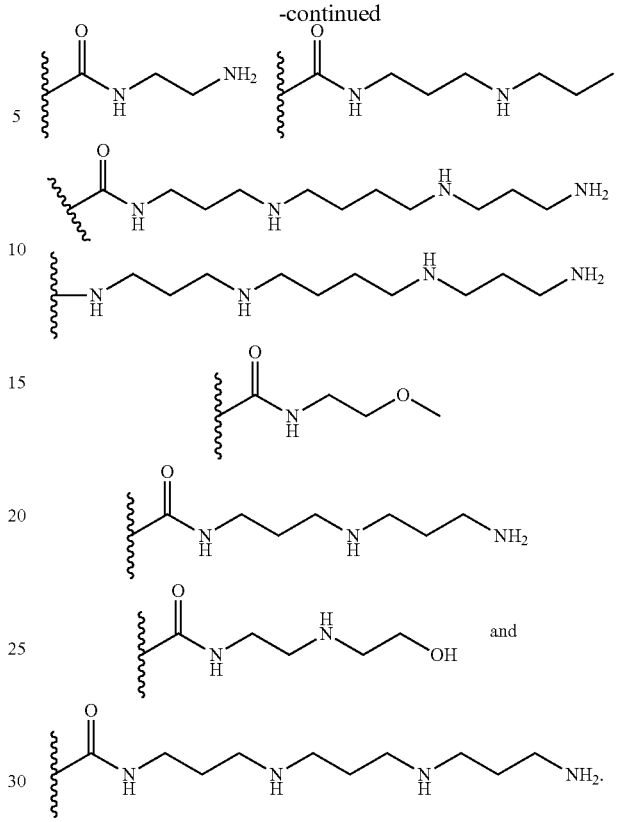

22. The compound of any one of embodiments 16 to 21, wherein the compound has a viscosity of equal to or at least about 20 mPa·s at 20° C. at a concentration of 20% w/w in water.

23. The compound of any one of embodiments 16 to 22, wherein the compound is soluble in water at a concentration of 50 mg/ml.

24. The compound of any one of embodiments 16 to 23, wherein the compound has a total releasable NO storage in a range of 0.1-1.0 μmol of NO per mg of compound.

25. The compound of any one of embodiments 16 to 24, wherein the compound has a NO half-life in the range of 0.1-24 hours.

26. The compound of any one of embodiments 16 to 24, wherein the compound has a total duration of NO release in the range of 1-60 hours.

27. The compound of any one of embodiments 16 to 24, wherein the total NO release after 4 hours is in the range between 0.1-1.0 μmol of NO per mg of compound.

28. The compound of any one of embodiments 1 to 13, wherein the compound has a molecular weight in the range of about 6 kDa and about 90 kDa.

29. A viscosity enhancing agent comprising:
a scaffold comprising a polymer having structural units along a chain of the polymer, one or more structural units being functionalized with one or more instances of each of $R_1$, $R_2$, and $R_3$;
wherein
$R_1$, $R_2$, and $R_3$ are independently selected from the group consisting of —OH, —$NH_2$, —$OCH_3$, —C(O)OH, —$CH_2OH$, —$CH_2OCH_3$, —$CH_2OCH_2CH_2OH$, —$OCH_2C(O)OH$, —$CH_2OCH_2C(O)OH$, —$CH_2C(O)OH$, —NHC(O)—$CH_3$, —$C(O)O((CH_2)_aO)_b$—H, —$C(O)O((CH_2)_aO)_b$—$(CH_2)_cH$, —$C(O)O(C_{1-5}alkyl)$, —C(O)—NH—((CH$_2$)$_d$NH)$_e$—H, —C(O)—NH—((CH$_2$)$_d$NH)$_e$—(CH$_2$)$_f$H, —CH$_2$C(O)—NH—CH$_2$)$_d$NH)$_e$—H, —CH$_2$C(O)—NH—((CH$_2$)$_d$NH)$_e$—(CH$_2$)$_f$H, —C(O)—X$^1$—((CH$_2$)$_g$X$^2$)$_h$—(CH$_2$)$_i$H, —C(O)—X$^1$—((CH$_2$)$_g$X$^2$)$_h$(CH$_2$)$_j$ X$^3$)$_k$—(CH$_2$)$_l$H, —O—((CH$_2$)$_a$O)$_b$—H, —O—((CH$_2$)$_a$O)$_b$—(CH$_2$)$_c$H, —O—(C$_{1-5}$alkyl), —NH—((CH$_2$)$_d$NH)$_e$—H, —NH—((CH$_2$)$_d$NH)$_e$—(CH$_2$)$_f$H, —X$^1$—((CH$_2$)$_g$X$^2$)$_h$—(CH$_2$)$_i$H, —CH$_2$C(O)—X$^1$—((CH$_2$)$_g$X$^2$)$_h$—(CH$_2$)$_i$H, —X$^1$—((CH$_2$)$_g$X$^2$)$_h$((CH$_2$)$_j$X$^3$)$_k$—(CH$_2$)$_l$H, —CH$_2$C(O)—X$^1$—((CH$_2$)$_g$X$^2$)$_h$((CH$_2$)$_j$X$^3$)$_k$—(CH$_2$)$_l$H;

each instance of a, b, c, d, e, f, g, h, i, j, k, and l is independently selected from an integer of 0, 1, 2, 3, 4, 5, 6, 7, 8, 9, or 10;

each instance of X$^1$, X$^2$, and X$^3$ is independently selected from —O—, —S—, —NH—, C(O)NH—; and at least one instance of X$^1$, X$^2$, and X$^3$ is represented by one of the following:

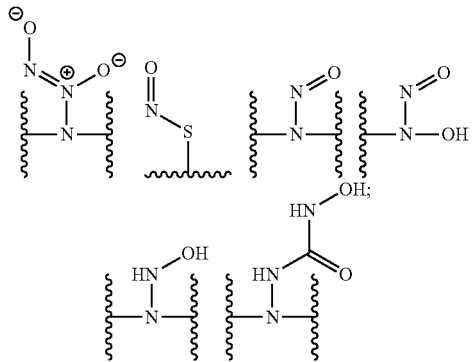

and the scaffold has a viscosity of equal to or at least about 10 mPa·s at 20° C. at a concentration of 5% w/w.

30. The viscosity inducing agent of embodiment 29, wherein the scaffold has a gel firmness of equal to or at least about 1.0 mN at a concentration of 5% w/w.

31. The viscosity inducing agent of embodiment 29, wherein the polymer is a biopolymer.

32. The viscosity inducing agent of embodiment 29, wherein the polymer is a polysaccharide.

33. The viscosity inducing agent of embodiment 32, wherein the one or more structural units are represented by Formula I:

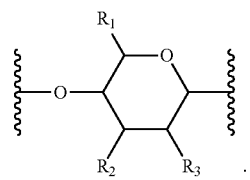

Formula I

34. The viscosity inducing agent of embodiment 33, wherein the structure of Formula I represents a saccharide unit of a carboxymethylcellulose polymer.

35. The viscosity inducing agent of embodiment 33, wherein the structure of Formula I represents a saccharide unit of a hyaluronic acid polymer.

36. The viscosity inducing agent of embodiment 33, wherein the structure of Formula I represents a saccharide unit of a hydroxyethyl cellulose polymer.

37. The viscosity inducing agent of embodiment 33, wherein the structure of Formula I represents a saccharide unit of a methyl cellulose polymer.

38. The viscosity inducing agent of embodiment 33, wherein the structure of Formula I represents a saccharide unit of an alginate polymer.

39. The viscosity inducing agent of embodiment 33, wherein the structure of Formula I represents a saccharide unit of a cyclodextrin ring structure.

40. The viscosity inducing agent of embodiment 29, wherein the polymer comprises a polyaminoglycoside.

41. The viscosity inducing agent of embodiment 40, wherein the polyaminoglycoside is a hyperbranched polyaminoglycoside, comprising a first aminoglycoside of Formula III:

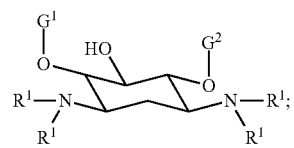

Formula III wherein G$^1$ is selected from the group consisting of:

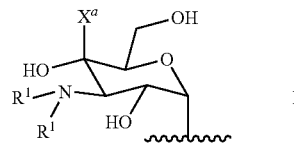 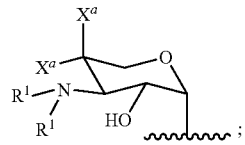

wherein G$^2$ is selected from the group consisting of:

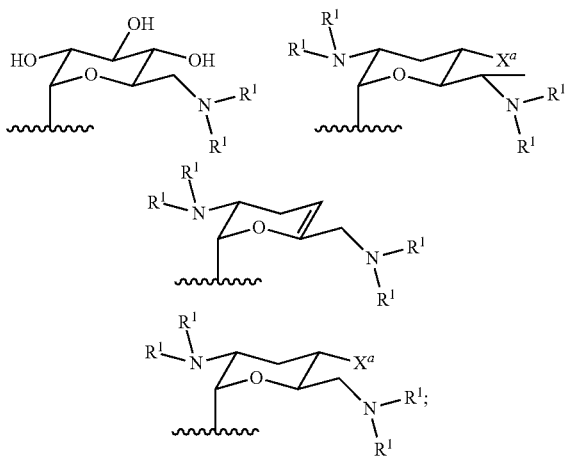

wherein each instance of R$^1$ is independently selected from the group consisting of —H, optionally substituted C$_1$-C$_6$ alkyl, optionally substituted polyamino having 1 to 6 repeat units with intervening C$_1$-C$_6$ alkyl groups, optionally substituted polyether having 1 to 6 repeat units with intervening C$_1$-C$_6$ alkyl groups, or indicates a covalent bond to a linking unit;

wherein each instance of X$^a$ is independently selected from —H, —OH, and C$_1$-C$_6$ alkyl;

wherein at least one instance of R$^1$ indicates a covalent bond to one or more linking units selected from the following:

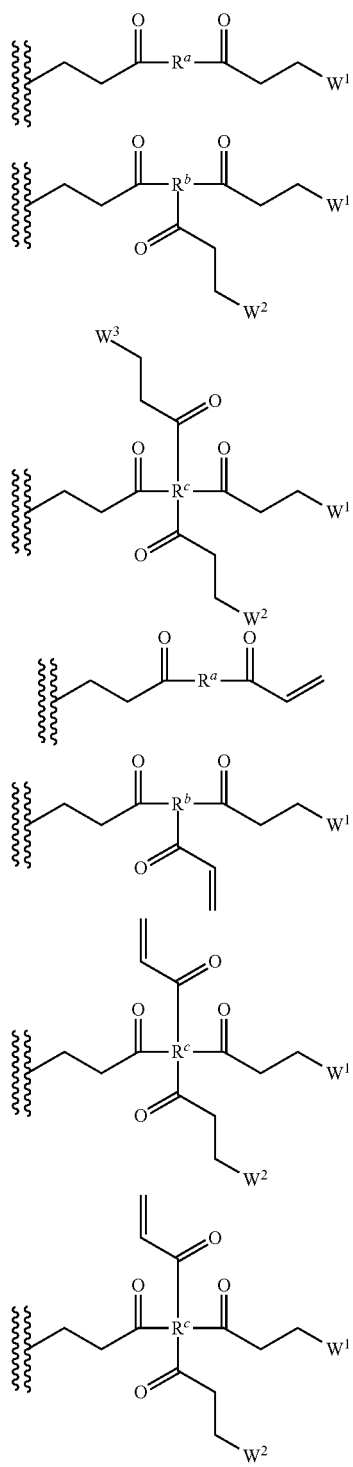

wherein "⌇" indicates an attachment to the first aminoglycoside;

wherein each instance of W¹, where present, is independently selected from one or more additional aminoglycosides or one or more end-capping substituents and at least one linking unit provides a covalent bridge from the first aminoglycoside to a second aminoglycoside;

wherein each instance of $R^a$ is independently selected from the group consisting of optionally substituted $C_1$-$C_6$alkyl, optionally substituted polyamino having 1 to 6 repeat units (with $C_1$-$C_6$ alkyl(s)), or optionally substituted polyether having 1 to 6 repeat units (with $C_1$-$C_6$ alkyl(s)); and wherein the one or more end-capping substituents, where present, independently have a formula of —$X^1$—$((CH_2)_nX^2)_i$—$(CH_2)_j$H.

42. The viscosity inducing agent of embodiment 41, further comprising an end group selected from the group consisting of:

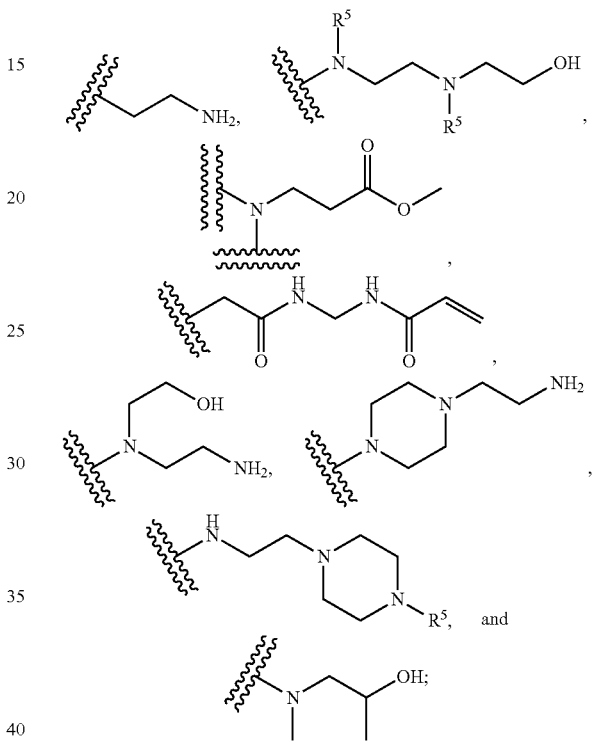

wherein each instance of $R^5$ is H or —$N^+(=N-O^-)O^-$.

43. The viscosity inducing agent of embodiment 41 or 42, further comprising an end group selected from the group consisting of:

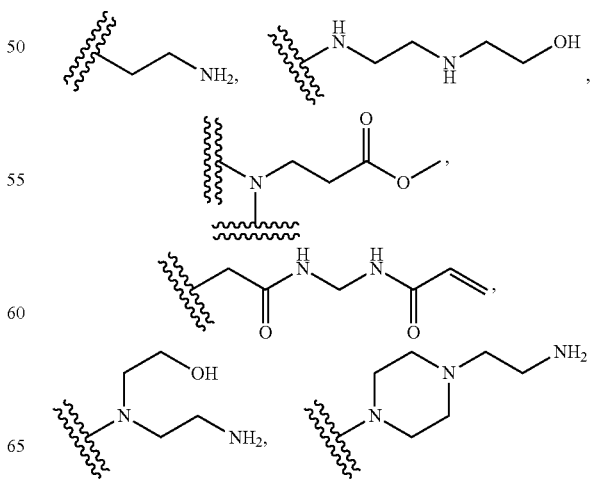

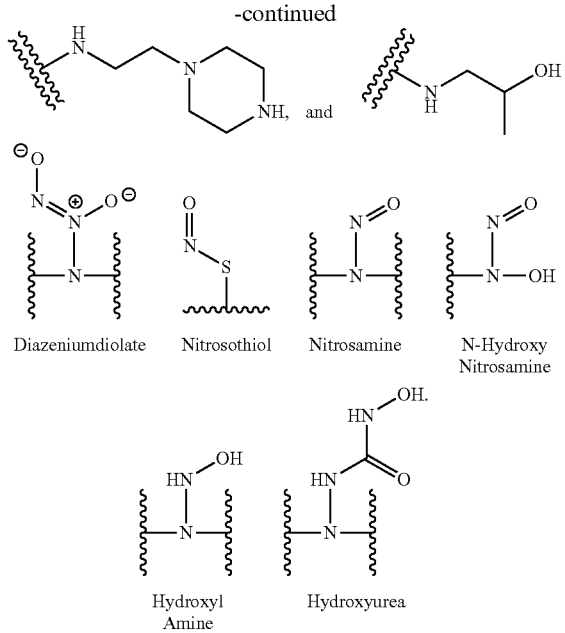
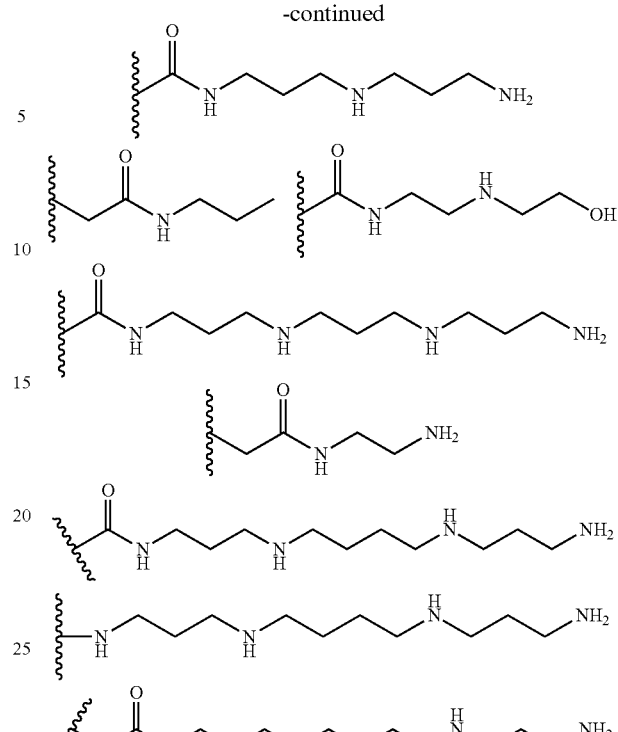
44. The viscosity inducing agent of any one of embodiments 29 to 41, wherein one or more of $R_1$, $R_2$, and $R_3$ are independently selected from the group consisting of:
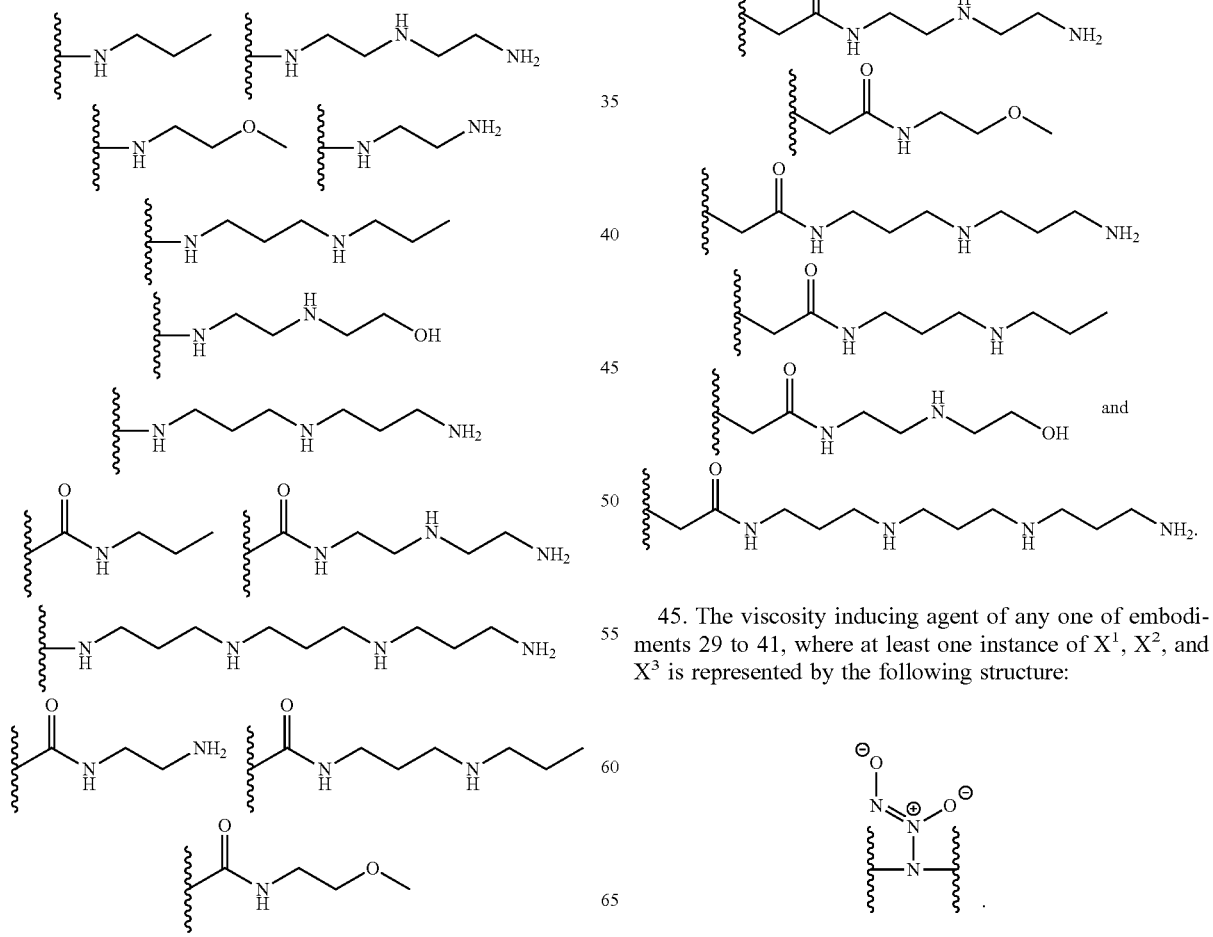
45. The viscosity inducing agent of any one of embodiments 29 to 41, where at least one instance of $X^1$, $X^2$, and $X^3$ is represented by the following structure:
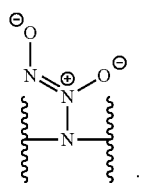 [SMILES: *N(*)/[N+]([O-])=N/[O-]]

46. A method of delivering nitric oxide to a subject in need of treatment, comprising:
administering an effective amount of the compounds or viscosity inducing agents of any one of embodiments 1 to 45 to the subject.

47. The method of embodiment 46, wherein the effective amount of the compounds or viscosity inducing agents is a hydrogel.

48. The method of embodiments 46 or 47, wherein the subject has suffered a wound and the compounds or viscosity inducing agents are administered to aid in wound healing.

49. The method of embodiments 46 or 47, wherein the subject is in need of tissue replacement and the compounds or viscosity inducing agents are administered as a tissue scaffold.

50. A method of treating a disease state, comprising:
administering an effective amount of the compounds or viscosity inducing agents of any one of embodiments 1 to 45 to a subject in need thereof, wherein said disease state is selected from the group consisting of a cancer, a cardiovascular disease, a microbial infection, platelet aggregation and platelet adhesion caused by the exposure of blood to a medical device, pathological conditions resulting from abnormal cell proliferation, transplantation rejections, autoimmune diseases, inflammation, vascular diseases, scar tissue, wound contraction, restenosis, pain, fever, gastrointestinal disorders, respiratory disorders, sexual dysfunctions, and sexually transmitted diseases.

51. A pharmaceutical formulation comprising:
the compounds or viscosity inducing agents of any one of embodiments 1 to 45; and
a pharmaceutically acceptable excipient.

52. A method of reducing or preventing microbial load on a surface comprising,
applying the compounds or viscosity inducing agents of any one of embodiments 1 to 45 to a surface contaminated with a plurality of microbes;
wherein the compounds or viscosity inducing agents of any one of embodiments 1 to 45 generate nitric oxide and induce oxidative and/or nitrosative damage to microbial DNA and membrane structures, thereby preventing or reducing microbial load, and wherein said plurality of microbes comprises two or more of the following: gram-positive bacteria, gram-negative bacteria, fungi, yeast, and viruses.

53. The method according to embodiment 52, wherein the surface is an organic surface.

54. The method of embodiment 52 or 53, wherein the surface is human skin.

55. The method of embodiment 52 or 53, wherein the surface is a wound surface.

56. The method of embodiment 54 or 55, wherein said application does not induce skin irritation.

57. The method of embodiment 52 or 53, wherein the surface is animal skin.

58. The method of embodiment 57, wherein said application does not induce skin irritation.

59. The method of embodiment 52, wherein the surface is an inorganic surface.

60. The method of embodiment 59, wherein the inorganic surface is an external or internal surface of a medical device.

61. The method of embodiment 60, wherein application of the compound generates an anti-microbial coating on the external or internal surface of the medical device.

62. The method of embodiment 60 or 61, wherein the medical device comprises an endoscope.

63. The method according to any one of embodiments 52 to 62, wherein the microbial load comprises drug-resistant bacteria.

64. The method according to any one of embodiments 52 to 63, wherein the microbial load comprises microbes associated with the presence of one or more of human immunodeficiency virus, herpes simplex virus, papilloma virus, parainfluenza virus, influenza, hepatitis, Coxsackie Virus, herpes zoster, measles, mumps, rubella, rabies, pneumonia, hemorrhagic viral fevers, H1N1, prions, parasites, fungi, mold, *Candida* albicans, *Aspergillus niger, Escherichia coli, Pseudomonas aeruginosa*, and *Staphylococcus aureus*, Group A streptococci, *S. pneumoniae, Mycobacterium tuberculosis, Campylobacter jejuni, Salmonella, Shigella*, carbapenem-resistant Enterobacteriaceae Methicillin-resistant *Staphylococcus aureus*, and Burkholderia cepacia.

65. The method according to any one of embodiments 52 to 63, wherein the microbial load comprises Methicillin-resistant *Staphylococcus aureus*.

66. The method according to any one of embodiments 52 to 63, wherein the microbial load comprises carbapenem-resistant Enterobacteriaceae.

67. The method according to any one of embodiments 52 to 63, wherein the microbial load comprises *Staphylococcus aureus*.

68. The method according to any one of embodiments 52 to 63, wherein the microbial load comprises *Pseudomonas aeruginosa*.

69. The method according to any one of embodiments 52 to 63, wherein the microbial load comprises Burkholderia cepacia.

70. A method of manufacturing any one of the compounds or viscosity inducing agents of any one of embodiments 1 to 45, comprising:
selecting a polymer; and
functionalizing the polymer with NO binding moiety.

71. The method of embodiment 70, wherein the polymer is a biopolymer.

72. The method of embodiment 70 or 71, further comprising exposing the compounds or viscosity inducing agents to NO to provide a NO donating compound or viscosity inducing agent.

73. Use of a compound or viscosity inducing agent of any one of embodiments 1 to 45 for the delivery of nitric oxide to a subject in need of treatment of a disease, tissue damage, or reduction of microbial load.

74. Use of a compound or viscosity inducing agent of any one of embodiments 1 to 45 for the manufacture of a medicament configured to deliver nitric oxide to a subject in need of treatment of a disease, tissue damage, or reduction of microbial load.

In several embodiments, polymers as disclosed in each of U.S. Patent Application No. 62/441,742, U.S. Patent Application No. 62/483,505 International Application No. PCT/IB2018/050051, U.S. Patent Application No. 62/447,564, International Application No. PCT/IB2018/052144, U.S. patent application Ser. No. 14/421,525, U.S. Patent Application No. 62/639,119, and U.S. Patent Application No. 62/737,603 are used. Each of these applications and publications is incorporated by reference in its entirety for all purposes.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Exemplary Synthesis Method

Example 1: Hyaluronic Acid Scaffolds

The following examples pertain to the synthesis of N-diazeniumdiolate functionalized nitric oxide (NO)-releasing hyaluronic acid with tunable NO storage and release kinetics. This embodiment has the following features, advantages, and/or uses. The water solubility and biocompatibility of these scaffolds are high at high molecular weight (~90 kDa) and low molecular weight (~6 kDa) of the NO-release scaffold.

In several embodiments, theses scaffolds may be useful in the treatment for chronic wounds with the NO-releasing hyaluronic acid derivatives used for antibacterial therapy and cell proliferation. In several embodiments, these scaffolds could also be used as a therapeutic for cystic fibrosis with the NO-releasing material acting as an antibacterial agent.

Synthesis Details

Materials. Low molecular weight (80-110 kDa) and ultra low molecular weight (<6 kDa) hyaluronic acid (HA) were obtained from Lotioncrafter (Eastsound, WA). Bis(3-aminopropyl)amine (DPTA), diethylenetriamine (DETA), N-propyl-1,3-propanediamine (PAPA), N-(2-hydroxyethyl)ethylenediamine (HEDA), 1-ethyl-3-(3-dimethylaminopropyl) carbodiimide hydrochloride (EDC), N-hydroxysuccinimide (NHS), neomycin sulfate, phenazine methosulfate (PMS), and hyaluronidase (from bovine testes, Type I-S) were purchased from Millipore Sigma (St. Louis, MO). 3-(4,5-dimethylthiazol-2-yl)-5-(3-carboxymethoxyphenyl)-2-(4-sulfophenyl)-2H-tetrazolium inner salt (MTS) was purchased from BioVision (Milpitas, CA). Common laboratory salts and solvents were purchased from Fisher Scientific (Fair Lawn, NJ). Unless otherwise specified, all reagents were used as received without further purification. Tryptic soy broth (TSB) and tryptic soy agar (TSA) were obtained from Becton, Dickinson, and Company (Franklin Lakes, NJ). Trypsin, penicillin streptomycin (PS), Dulbecco's modified Eagle's medium (DMEM), and L929 murine fibroblasts (ATCC CCL1) were purchased from the UNC Tissue Culture Facility (Chapel Hill, NC). *Pseudomonas aeruginosa* (*P. aeruginosa*; ATCC #47085), *Escherichia coli* (*E. coli*; ATCC #43888), *Staphylococcus aureus* (*S. aureus*; ATCC #29213), *Enterococcus faecalis* (*E. faecalis*; ATCC #29212), multidrug-resistant *P. aeruginosa* (ATCC #BAA-2110), and methicillin-resistant *S. aureus* (MRSA; ATCC #33591) were obtained from the American Type Tissue Culture Collection (Manassas, VA). Argon (Ar), carbon dioxide ($CO_2$), nitrogen ($N_2$), oxygen ($O_2$), nitric oxide (NO) calibration (25.87 ppm balance $N_2$), and pure NO (99.5%) gas cylinders were purchased from Airgas National Welders (Raleigh, NC). Distilled water was purified to a resistivity of 18.2 MΩ·cm and a total organic content of ≤6 ppb using a Millipore Milli-Q UV Gradient A10 system (Bedford, MA).

Synthesis of alkylamine-modified hyaluronic acid (HAMW-alkylamine). Hyaluronic acid (90 kDa or 6 kDa) materials were modified with either N-propyl-1,3-propanediamine (PAPA), N-(2-hydroxyethyl)ethylenediamine (HEDA), bis(3-aminopropyl)amine (DPTA), or diethylenetriamine (DETA) (Scheme 1a). Briefly, HA (1 g) was dissolved in 40 mL (6 kDa HA) or 100 mL (90 kDa HA) of distilled water. A 4:1 molar ratio of 1-ethyl-3-(3-dimethylaminopropyl)carbodiimide hydrochloride (EDC) and N-hydroxysuccinimide (NHS), with respect to the carboxylic acid moieties on the HA scaffold, was added, and the solution was titrated to a pH of 3.0 using 0.5 M HCl. Following a 20 min activation period at room temperature, an 8:1 molar ratio of PAPA, DPTA, or DETA or 4:1 molar ratio of HEDA was added dropwise to the reaction solution. The solution was stirred at room temperature for 48 h. Amine-modified HA was precipitated in ethanol, collected via centrifugation, washed twice with ethanol, and dried in vacuo to yield a white solid for each modification.

Characterization of alkylamine-modified hyaluronic acid. Elemental (carbon, hydrogen, and nitrogen; CHN) analysis was conducted using a PerkinElmer Elemental Analyzer Series 2400 Instrument (Waltham, MA) (Table 1). Gel permeation chromatography (GPC) measurements were conducted in 0.1 M phosphate buffer (pH 7.4) containing 0.1 M sodium nitrate and 0.02 wt % sodium azide using an aqueous GPC system equipped with a Waters 2414 refractive index detector (Milford, MA) coupled to a Wyatt miniDawn TREOS multi-angle light scattering detector (Santa Barbara, CA). The presence of unreacted starting materials was assessed using high-performance liquid chromatography (HPLC; Agilent Technologies 1260 Infinity II LC System; Santa Clara, CA) equipped with a diode array detector (DAD) and an evaporative light scattering detector (ELSD). Aliquots (20 µL) of 0.1 mg $mL^{-1}$ HA, EDC, or NHS samples were analyzed using a Synergi 4 µm Hydro-RP column (250×4.6 mm; Phenomenex; Torrance, CA) and a mobile phase composed of 80:20 acetonitrile:water at a flow rate of 1 mL $min^{-1}$. Elution was monitored via ELSD. $^1H$ and $^{13}C$ nuclear magnetic resonance (NMR) spectra were recorded on a Bruker (600 MHz) spectrometer (Billerica, MA).

Representative $^1H$ and $^{13}C$ NMR of HA and the alkylamine-modified HA derivatives included the following peaks:

HA90 and HA6: $^1H$ NMR (600 MHz, $D_2O$, δ) 2.00 (NHC(O)$CH_3$), 3.50 (CHC$H_2$OH), 3.60-4.50 (OCHCH(OH)CH(OH)), (OCHCH(OH)CH(OH), 4.50-4.60 (NHCOCH), 5.30 (OCH(CHOH)O), 6.30 (NHCHCH(OH)). $^{13}C$ NMR (600 MHz, $D_2O$, δ) 24.0 (NHC(O)$CH_3$), 65.0 (CHC$H_2$OH), 70.0-81.0 (OCHCH(OH)CH(OH)CH(OH)CH(O)), 95.0 (NHCHCH(OH)), 110.0 (OCHCH(OH)), 175.0 (CHC(O)OH).

HA90-DETA and HA6-DETA: $^1H$ NMR (600 MHz, $D_2O$, δ) 2.60-3.30 (C$H_2$C$H_2$NHC$H_2$C$H_2$N$H_2$), 2.00 (NHC(O)$CH_3$), 3.50 (CHC$H_2$OH), 3.60-4.50 (OCHCH(OH)CH(OH)), (OCHCH(OH)CH(OH), 4.50-4.60 (NHCOCH), 5.30 (OCH(CHOH)O), 6.10 (NHCHCH(OH)). $^{13}C$ NMR (600 MHz, $D_2O$, δ) 24.0 (NHC(O)$CH_3$), 40.0-49.0 (C(O)NHC$H_2$C$H_2$NHC$H_2$C$H_2$N$H_2$), 65.0 (CHC$H_2$OH), 70.0-81.0 (OCHCH(OH)CH(OH)CH(OH)CH(O)), 95.0 (NHCHCH(OH)), 110.0 (OCHCH(OH)), 170.0 (CHC(O)NH), 175.0 (CHC(O)OH).

HA90-DPTA and HA6-DPTA: $^1H$ NMR (600 MHz, $D_2O$, δ) 1.70-1.80 (C$H_2$C$H_2$C$H_2$NHC$H_2$C$H_2$C$H_2$N$H_2$), 2.00

(NHC(O)CH$_3$), 2.50-2.40 (CH$_2$CH$_2$CH$_2$NHCH$_2$CH$_2$CH$_2$NH$_2$), 2.70-3.20 (CH$_2$CH$_2$CH$_2$NHCH$_2$CH$_2$CH$_2$NH$_2$), 3.50 (CHCH$_2$OH), 3.60-4.50 (OCHCH(OH)CH(OH)), (OCHCH(OH)CH(OH), 4.50-4.60 (NHCOCH), 5.30 (OCH(CHOH)O), 6.10 (NHCHCH(OH)). $^{13}$C NMR (600 MHz, D$_2$O, δ) 24.0 (NHC (O)CH$_3$), 32.0 NHCH$_2$CH$_2$CH$_2$NH$_2$), 38.0 (C(O) NHCH$_2$CH$_2$CH$_2$NH), 39.0 (C(O)NHCH$_2$CH$_2$CH$_2$NH), 46.0 (C(O)NHCH$_2$CH$_2$CH$_2$NH, NHCH$_2$CH$_2$CH$_2$NH$_2$), 65.0 (CHCH$_2$OH), 70.0-81.0 (OCHCH(OH)CH(OH)CH (OH)CH(O)), 95.0 (NHCHCH(OH)), 110.0 (OCHCH(OH)), 170.0 (CHC(O)NH), 175.0 (CHC(O)OH).

HA90-PAPA and HA6-PAPA: $^1$H NMR (600 MHz, D$_2$O, δ) 0.80-0.90 (NHCH$_2$CH$_2$CH$_3$), 1.40-1.50 (NHCH$_2$CH$_2$CH$_3$), 1.70-1.80 (CH$_2$CH$_2$CH$_2$NHCH$_2$CH$_2$CH$_3$), 2.00 (NHC(O)CH$_3$), 2.50-3.20 (CH$_2$CH$_2$CH$_2$NHCH$_2$CH$_2$CH$_3$), 3.50 (CHCH$_2$OH), 3.60-4.50 (OCHCH(OH)CH(OH)), (OCHCH(OH)CH(OH), 4.50-4.60 (NHCOCH), 5.30 (OCH(CHOH)O), 6.10 (NHCHCH(OH)). $^{13}$C NMR (600 MHz, D$_2$O, δ) 11.0 (NHCH$_2$CH$_2$CH$_3$), 23.0 (NHCH$_2$CH$_2$CH$_3$), 24.0 (NHC(O) CH$_3$), 24.0-30.0 (C(O)NHCH$_2$CH$_2$CH$_2$NH, NHCH$_2$CH$_2$CH$_3$), 46.0-52.0 (C(O)NHCH$_2$CH$_2$CH$_2$NH, NHCH$_2$CH$_2$CH$_3$), 65.0 (CHCH$_2$OH), 70.0-81.0 (OCHCH (OH)CH(OH)CH(OH)CH(O)), 95.0 (NHCHCH(OH)), 110.0 (OCHCH(OH)), 170.0 (CHC(O)NH), 175.0 (CHC(O) OH).

HA90-HEDA and HA6-HEDA: $^1$H NMR (600 MHz, D$_2$O, δ) 1.75 (C(O)NHCH$_2$CH$_2$CH$_2$NH), 2.50-3.20 (C(O) NHCH$_2$CH$_2$CH$_2$NH), 2.70-3.50 (NHCH$_2$CH$_2$OH), 2.00 (NHC(O)CH$_3$), 3.50 (CHCH$_2$OH), 3.60-4.50 (OCHCH (OH)CH(OH)), (OCHCH(OH)CH(OH), 4.50-4.60 (NHCOCH), 5.30 (OCH(CHOH)O), 6.10 (NHCHCH(OH)). $^{13}$C NMR (600 MHz, D$_2$O, δ) 24.0 (NHC(O)CH$_3$), 29.0 (C(O)NHCH$_2$CH$_2$CH$_2$NH), 38.0 (C(O) NHCH$_2$CH$_2$CH$_2$NH), 46.0 (C(O)NHCH$_2$CH$_2$CH$_2$NH), 52.0 (NHCH$_2$CH$_2$OH), 61.0 (NHCH$_2$CH$_2$OH), 65.0 (CHCH$_2$OH), 70.0-81.0 (OCHCH(OH)CH(OH)CH(OH) CH(O)), 95.0 (NHCHCH(OH)), 110.0 (OCHCH(OH)), 170.0 (CHC(O)NH), 175.0 (CHC(O)OH).

Figure 2:
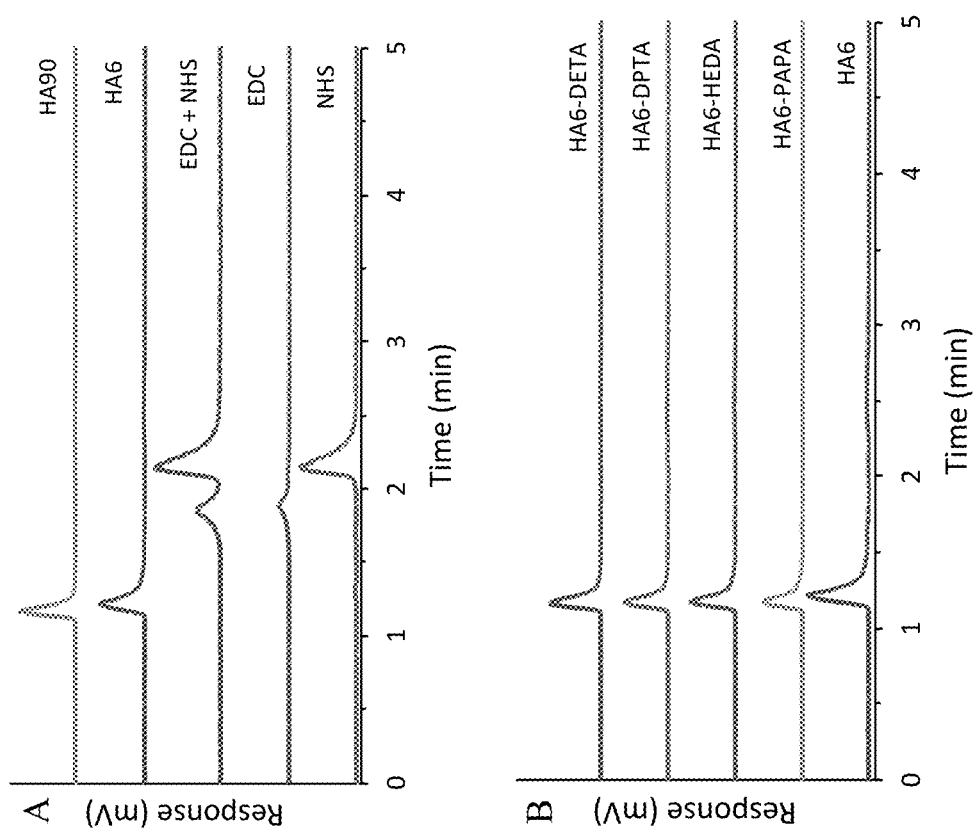
FIG. 2 shows purity analysis of amine-functionalized hyaluronic acid derivatives. (A) shows analysis of unreacted starting materials, (B) shows analysis of amine-modified 6 kDa HA derivatives, and (C) shows analysis of amine-modified 90 kDa HA derivatives via HPLC-ELSD. The amine-modified HA derivatives contain no detectable amounts of EDC and NHS reactants.
Figure 2:
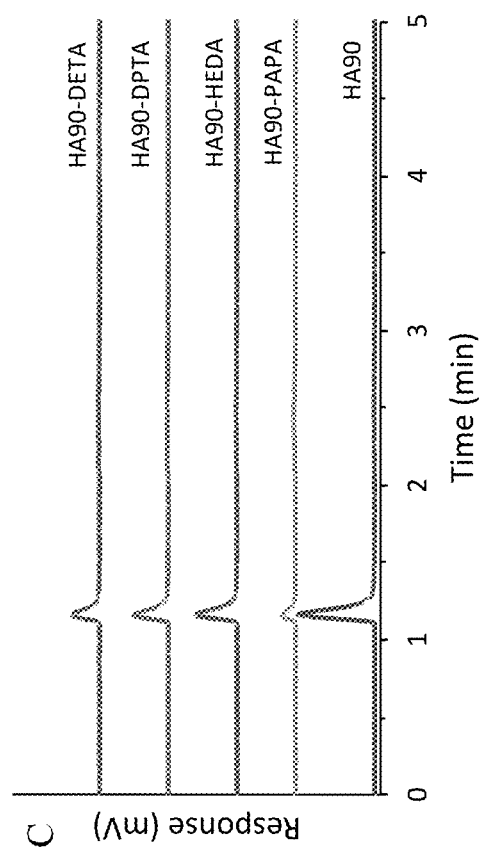
Figure 3:
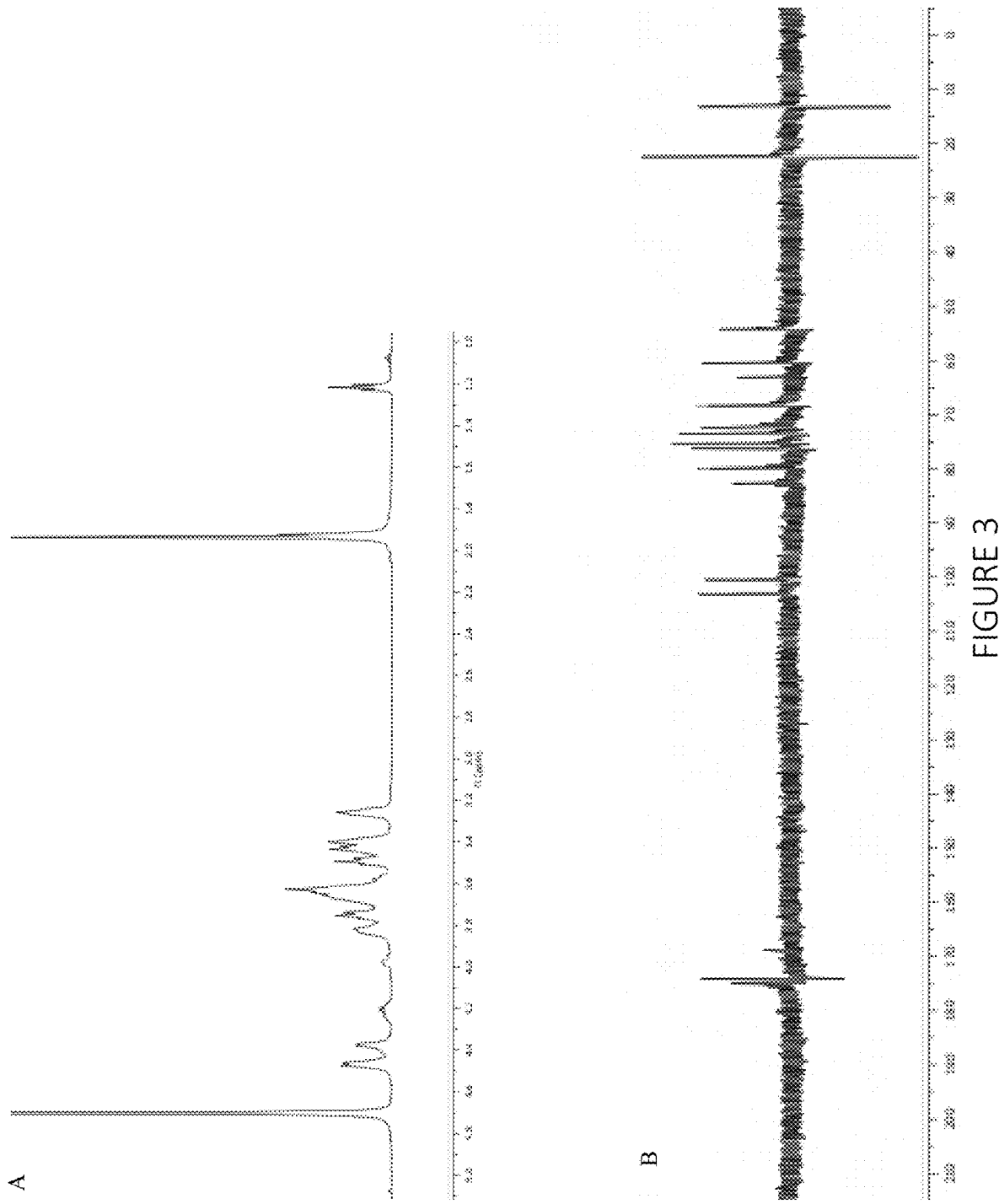
FIG. 3 shows representative $^1$H NMR and $^{13}$C NMR spectra of unmodified hyaluronic acid. (A) shows representative $^1$H NMR and (B) shows representative $^{13}$C NMR spectra of HA6 in $D_2O$.
Figure 4:
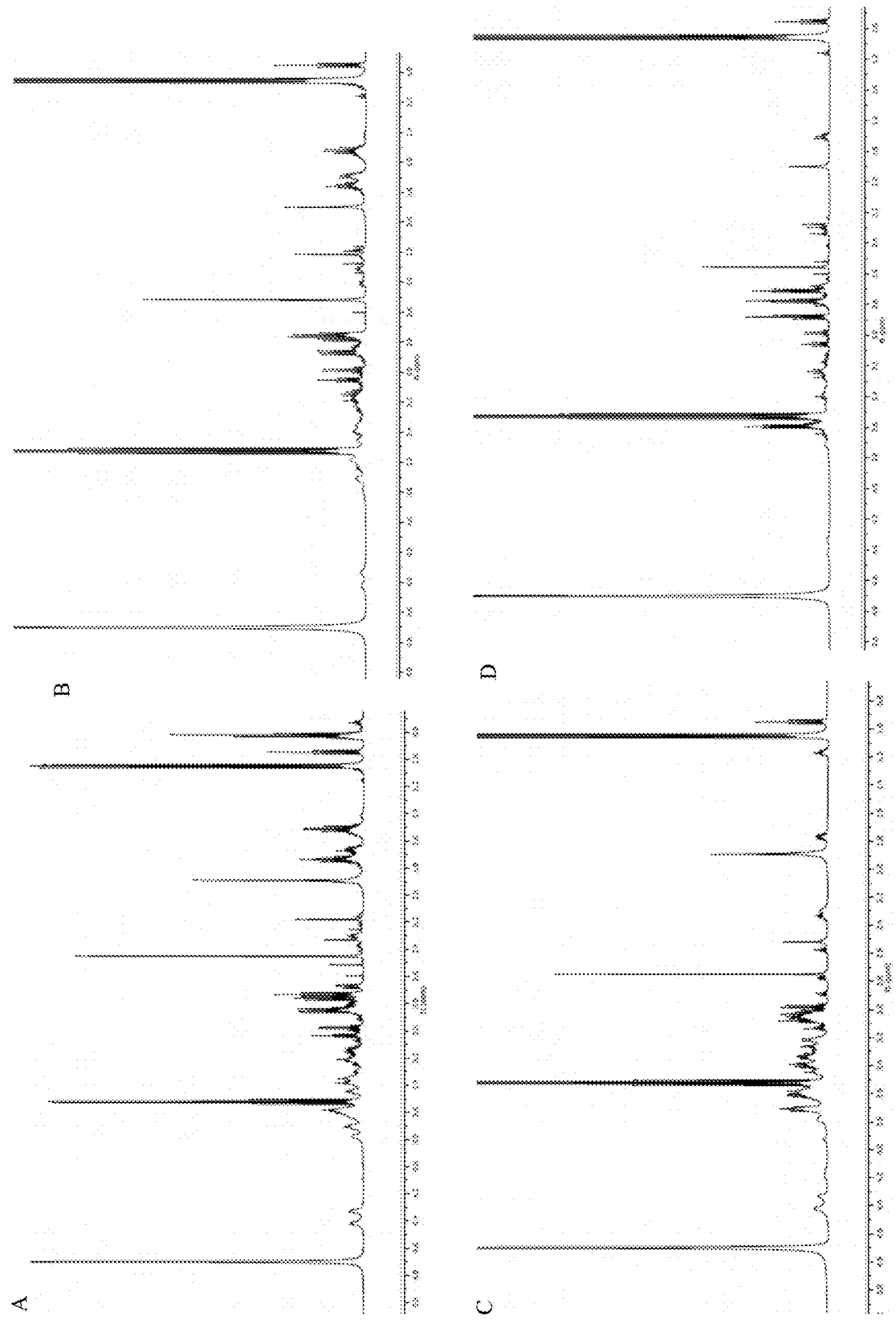
FIG. 4 shows representative $^1$H NMR spectra of secondary amine-functionalized hyaluronic acid. (A) shows representative $^1$H NMR of HA6-PAPA, (B) shows representative $^1$H NMR of HA90-PAPA, (C) shows representative $^1$H NMR of HA6-HEDA, (D) shows representative $^1$H NMR of HA90-HEDA, (E) shows representative $^1$H NMR of HA6-DPTA, (F) shows representative $^1$H NMR of HA90-DPTA, (G) shows representative $^1$H NMR of HA6-DETA, and (H) shows representative $^1$H NMR of HA90-DETA, in $D_2O$.
Figure 4:
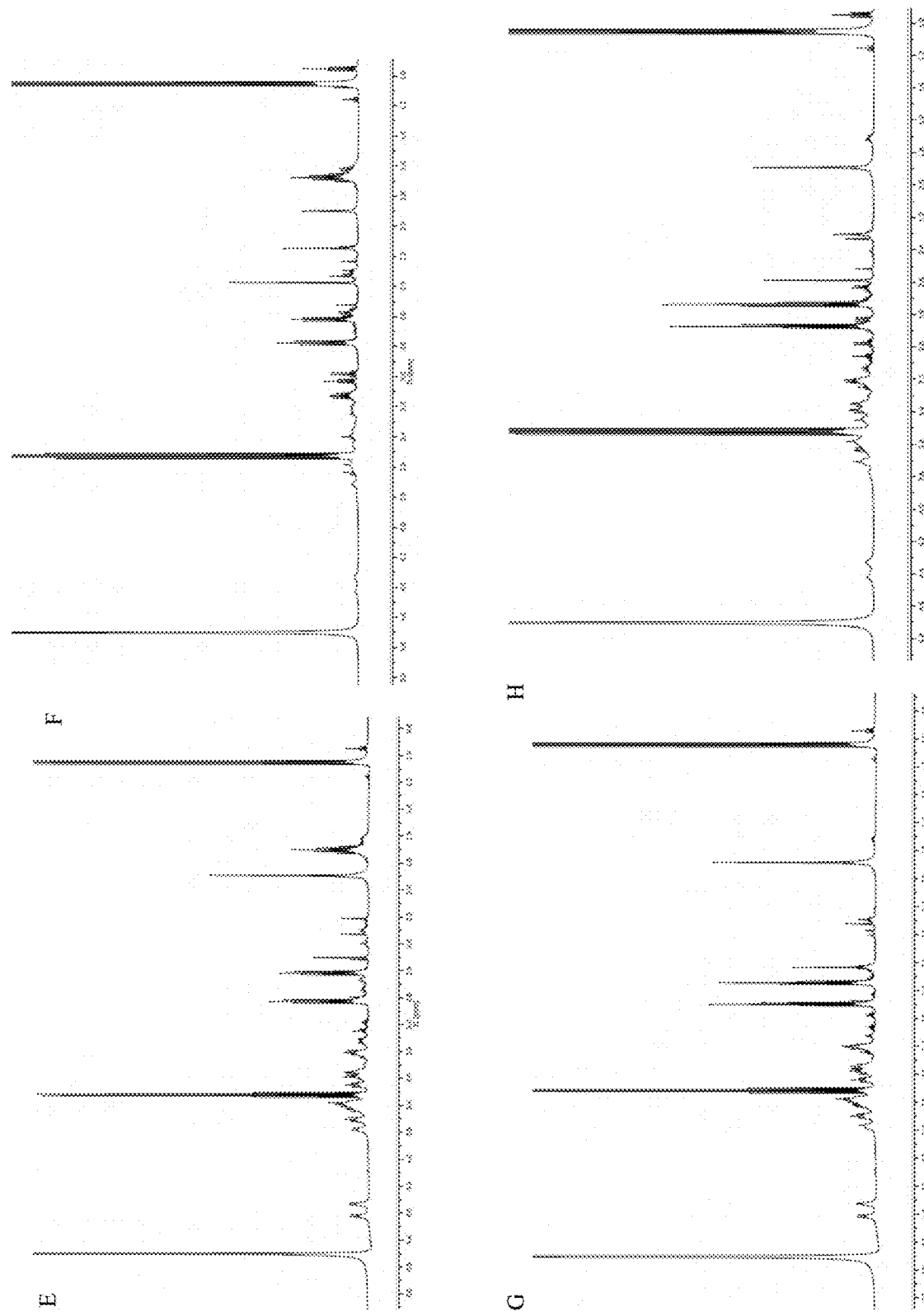
Figure 5:
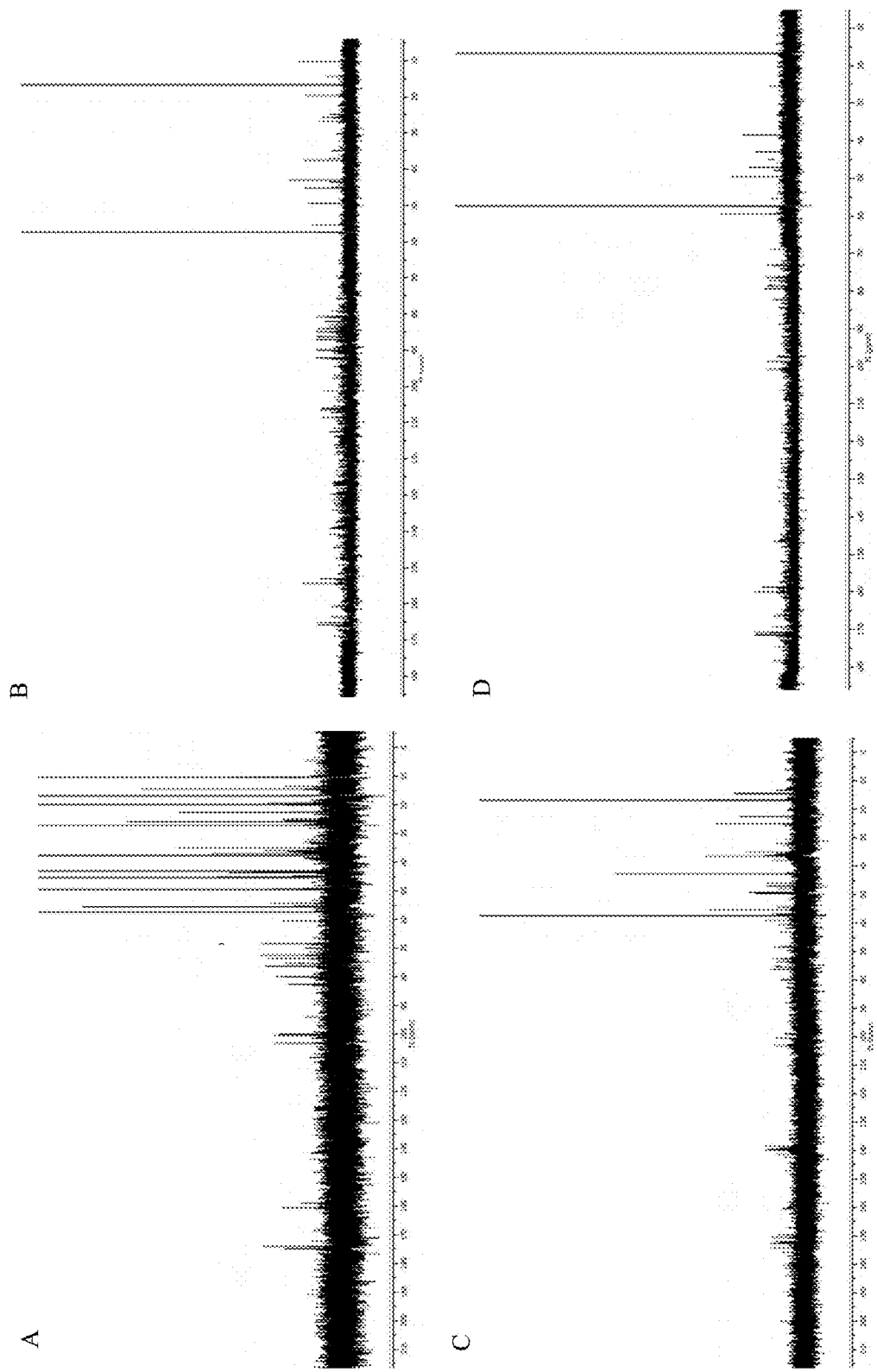
FIG. 5 shows representative $^{13}$C NMR spectra for secondary amine-functionalized hyaluronic acid, and a comparison of representative $^{13}$C NMR for unmodified and amine-modified hyaluronic acid. (A) shows representative $^{13}$C NMR of HA6-PAPA, (B) shows representative $^{13}$C NMR of HA90-PAPA, (C) shows representative $^{13}$C NMR of HA6-HEDA, (D) shows representative $^{13}$C NMR of HA90-HEDA, (E) shows representative $^{13}$C NMR of HA6-DPTA, (F) shows representative $^{13}$C NMR of HA90-DPTA, (G) shows representative $^{13}$C NMR of HA6-DETA, and (H) shows representative $^{13}$C NMR of HA90-DETA, in $D_2O$. (I) shows representative $^{13}$C NMR of unmodified and amine-modified hyaluronic acid.
Figure 5:
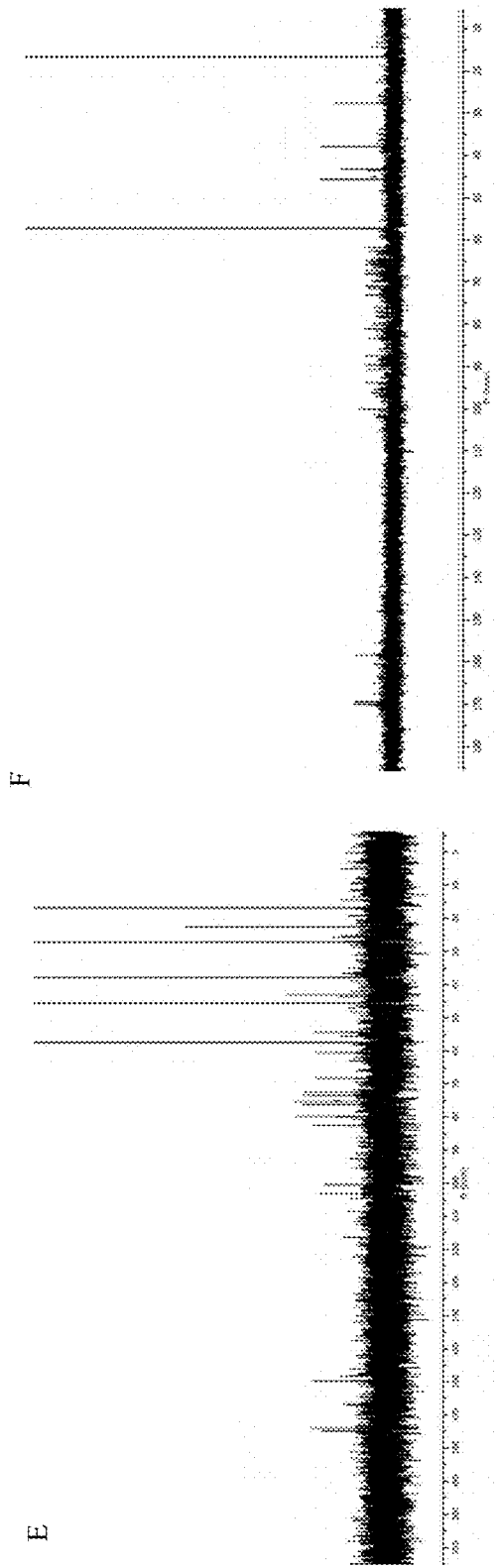
Figure 5:
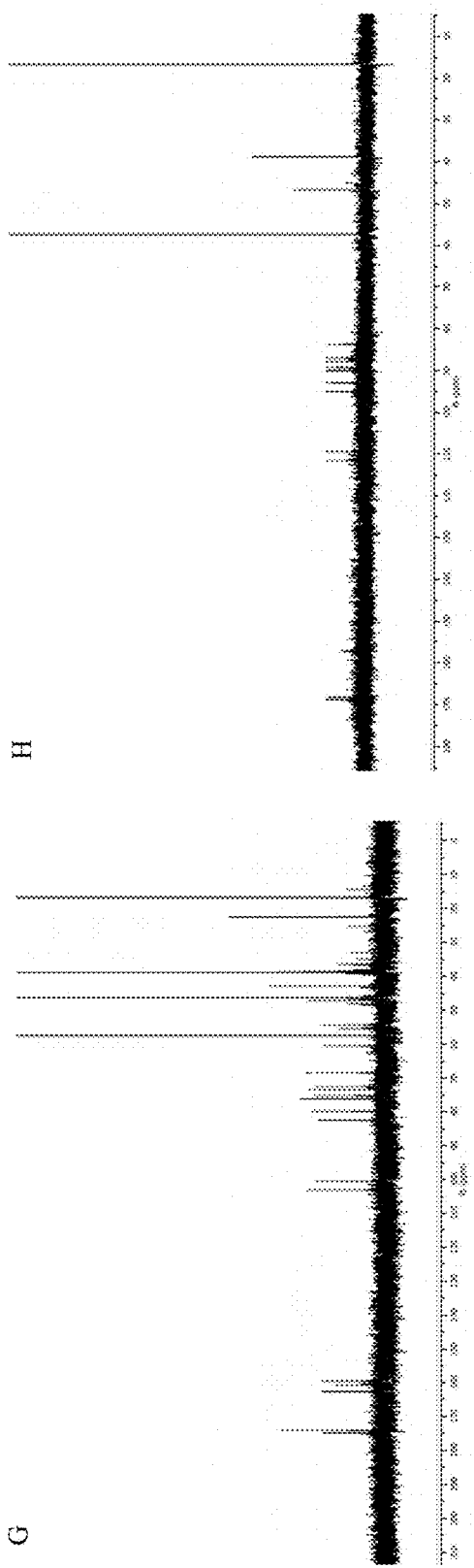
Figure 5:
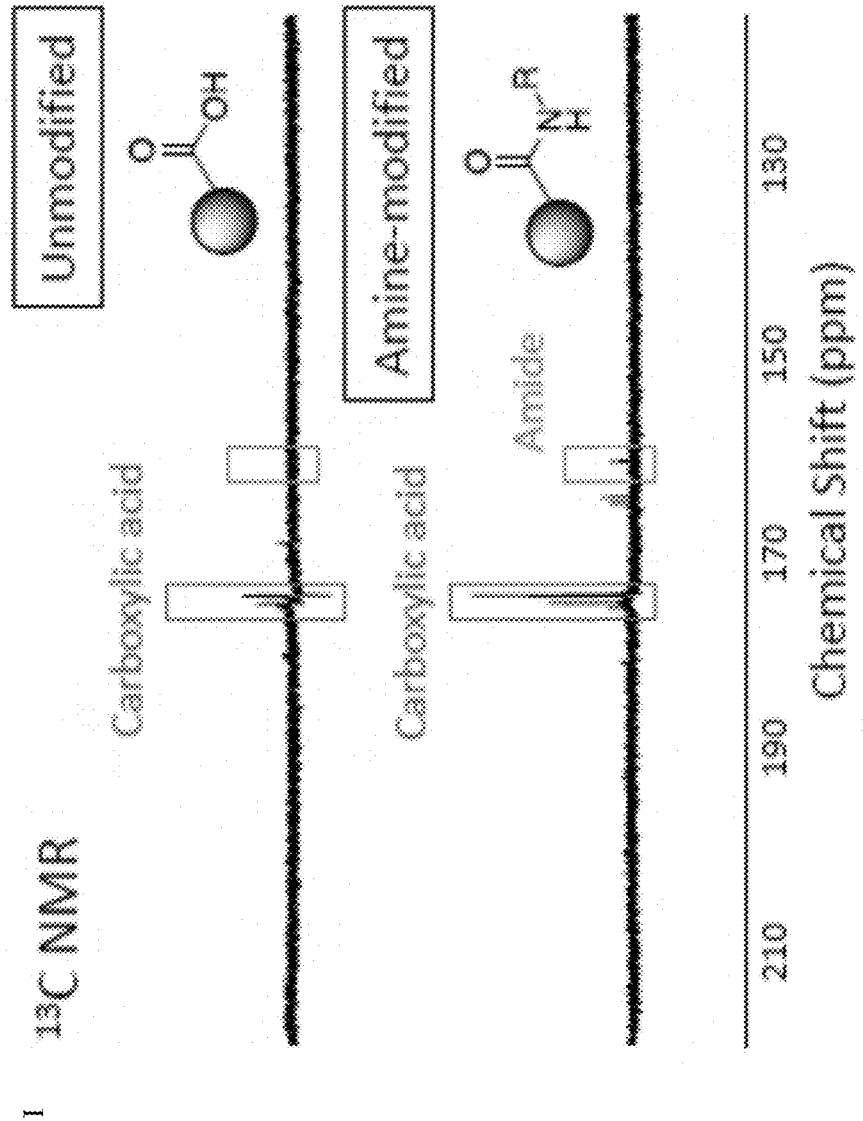

Purity analysis of amine-functionalized hyaluronic acid derivatives is set forth in FIG. 2. Representative $^1$H NMR and $^{13}$C NMR spectra of unmodified hyaluronic acid is set forth in FIG. 3. Representative $^1$H NMR spectra of secondary amine-functionalized hyaluronic acid is set forth in FIG. 4. Representative $^{13}$C NMR spectra for secondary amine-functionalized hyaluronic acid is set forth in FIG. 5 as well as a comparison of representative $^{13}$C NMR for unmodified and amine-modified hyaluronic acid. The presence of amide peak and increased nitrogen content confirm alkylamine modification.

Figure 6:
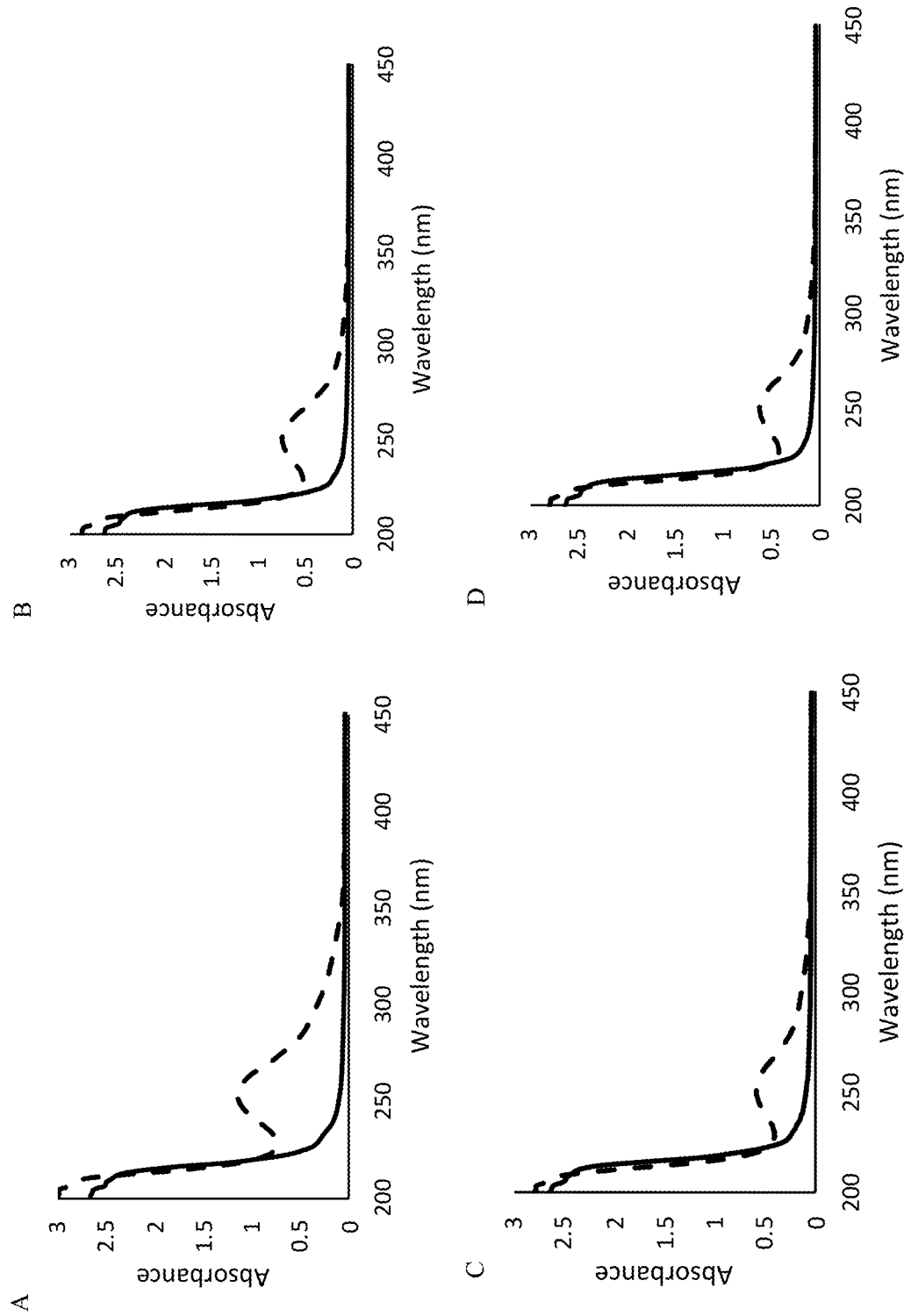
FIG. 6 shows representative UV-Vis spectra for the following secondary amine-functionalized and NO-releasing hyaluronic acid: (A) HA6-PAPA, (B) HA90-PAPA, (C) HA6-HEDA, (D) HA90-HEDA, (E) HA6-DPTA, (F) HA90-DPTA, (G) HA6-DETA, and (H) HA90-DETA. Modifications include: representative UV-Vis spectra of control (-) and NO-releasing (- -) hyaluronic acid.
Figure 6:
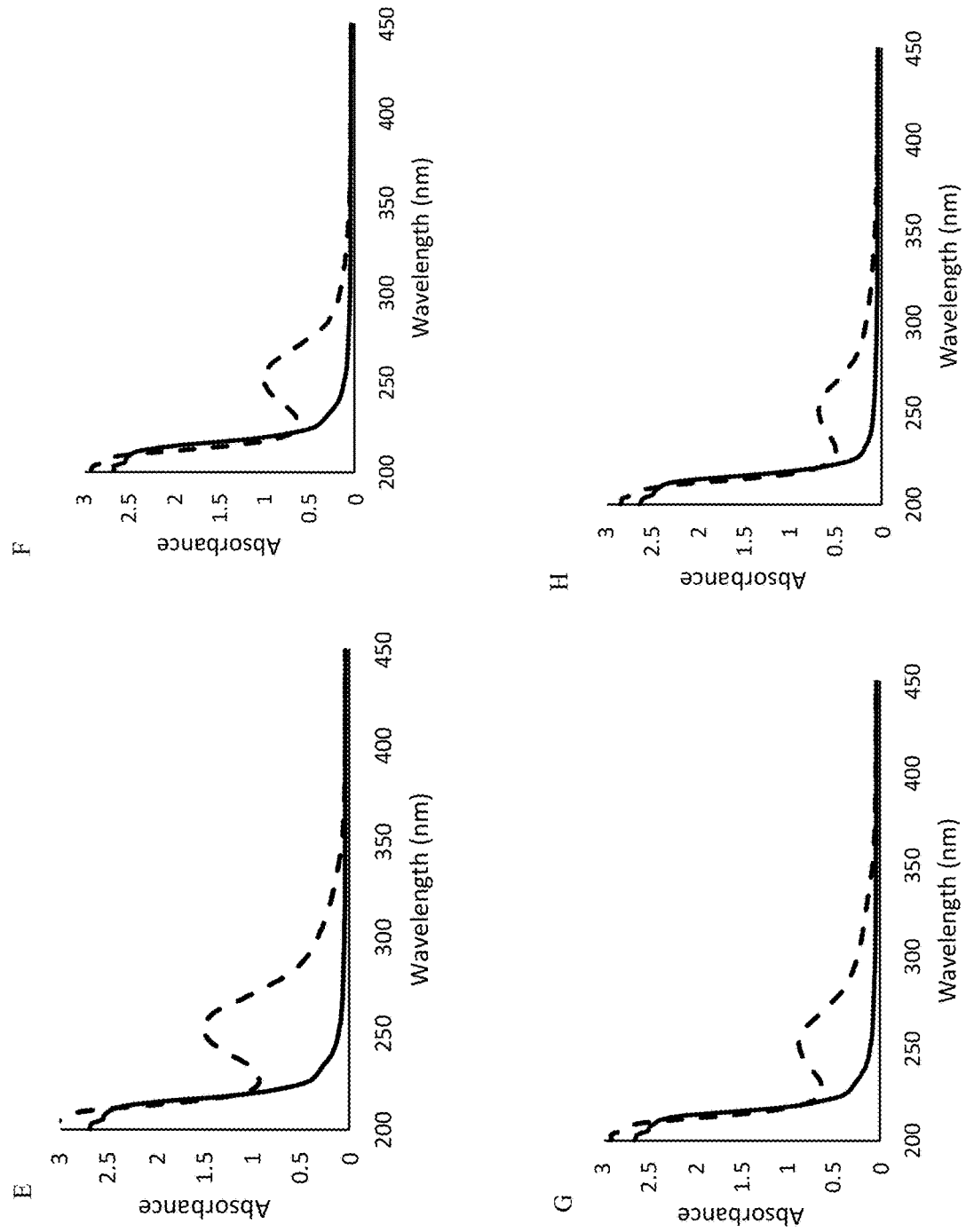

Synthesis of NO-releasing hyaluronic acid. Alkylamine-modified HA (45 mg) was dissolved in 7:3 methanol:water (3 mL) with sodium methoxide (75 µL; 5.4 mM in methanol) in a 1-dram glass vial. The open vials were placed in a stainless-steel reaction vessel and stirred continuously via magnetic stirring. The vessel was purged with argon (10 s, 7 atm) three times followed by three additional long purges (10 min, 7 atm) to remove excess oxygen. The vessel was then pressurized to 20 atm with NO gas (Scheme 1b). After 3 days, the same argon purging protocol was followed to remove unreacted NO. The resulting NO-releasing HA was then precipitated in ethanol, collected by centrifugation, dried in vacuo, and stored in vacuum sealed bags at –20° C. as a white/yellow powder. Representative UV-Vis spectra for secondary amine-functionalized and NO-releasing hyaluronic acid are set forth in FIG. 6.

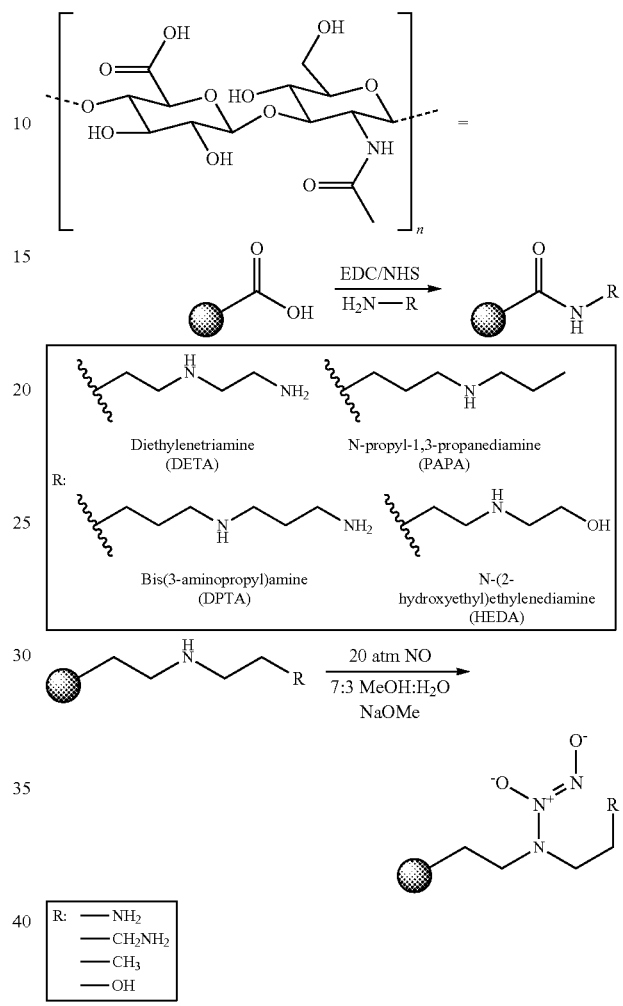

Scheme 1.
(A) Modification of hyaluronic acid with secondary amines to synthesize amine-functionalized hyaluronic acid (B) Formation of N-diazeniumdiolates on secondary amine-modified hyaluronic acid.

TABLE 1

Elemental analysis of bare and amine-modified hyaluronic acid and reaction conversion of carboxylic acid moieties on hyaluronic acid to secondary amine-bearing amide groups.[a]

| Modification | % C | % H | % N | Conversion Efficiency |
|---|---|---|---|---|
| HA6 | 39.2 ± 0.8 | 6.2 ± 0.3 | 3.0 ± 0.1 | — |
| HA6-PAPA | 41.6 ± 0.7 | 7.7 ± 0.2 | 6.9 ± 0.2 | 67% |
| HA6-HEDA | 40.6 ± 0.5 | 7.6 ± 0.2 | 8.2 ± 0.5 | 86% |
| HA6-DPTA | 40.9 ± 0.9 | 7.6 ± 0.1 | 8.2 ± 0.8 | 62% |
| HA6-DETA | 39.7 ± 0.2 | 6.9 ± 0.4 | 9.6 ± 0.4 | 73% |
| HA90 | 37.0 ± 0.2 | 6.1 ± 0.2 | 3.0 ± 0.0 | — |
| HA90-PAPA | 41.2 ± 1.2 | 7.6 ± 0.3 | 6.6 ± 0.4 | 62% |
| HA90-HEDA | 40.2 ± 0.7 | 7.1 ± 0.3 | 7.4 ± 0.1 | 73% |
| HA90-DPTA | 40.6 ± 1.5 | 7.4 ± 0.3 | 7.8 ± 0.5 | 57% |
| HA90-DETA | 39.9 ± 1.0 | 7.3 ± 0.6 | 9.0 ± 0.1 | 66% |

[a]Error represents standard deviation for n ≥ 3 separate syntheses.

Figure 7:
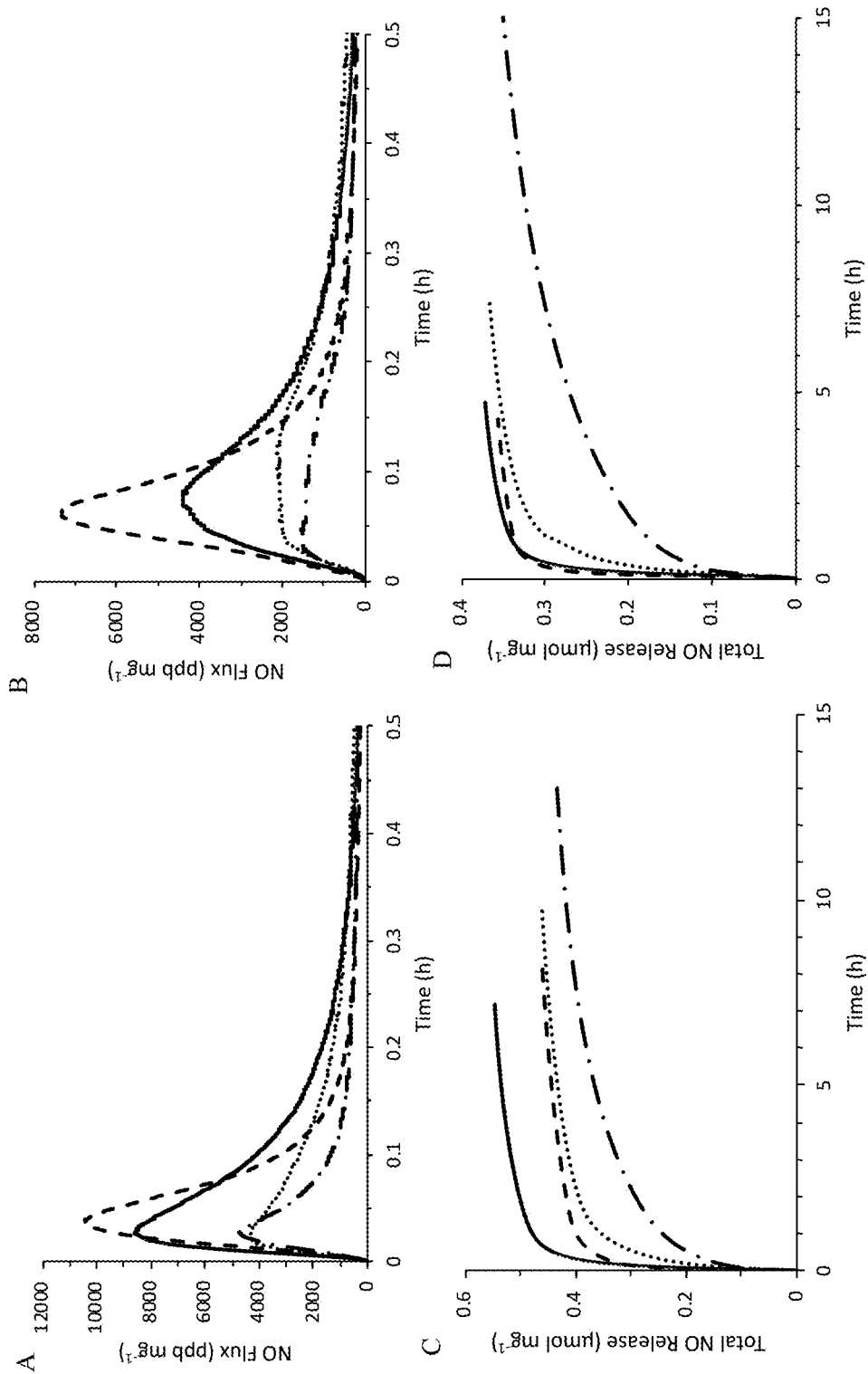
FIG. 7 shows real-time NO-release profiles and cumulative NO release of 6 and 90 kDa NO-releasing hyaluronic acid. (A-B) shows real-time NO-release profiles for the initial 30 minutes of release and (C-D) cumulative NO-release totals for (A, C) 6 kDa and (B, D) 90 kDa NO-releasing hyaluronic acid in PBS (10 mM, pH 7.4, 37° C.), wherein modifications include PAPA (- -), HEDA (-), DPTA ( ) and DETA (- -). (E) also shows real-time measurement of NO release.
Figure 7:
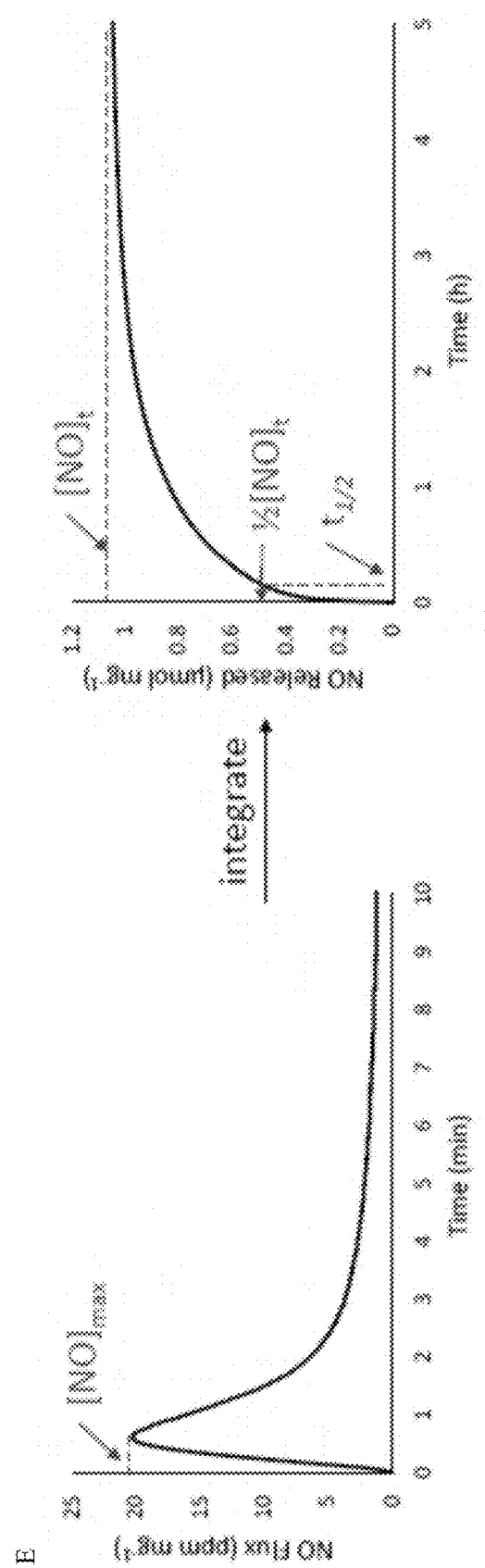

Characterization of NO storage and release. Absorbance measurements were made in 50 mM sodium hydroxide (NaOH) with a Molecular Devices SpectraMax M2 (San Jose, CA) to confirm the presence of the N-diazeniumdiolate functional group. Real-time nitric oxide release was evaluated using a Sievers 280i Nitric Oxide Analyzer (NOA; Boulder, CO). Before use, samples were analyzed to ensure stability of the stored material. The NOA was calibrated with air passed through a NO zero filter (0 ppm NO) and 25.87 ppm of NO calibration gas (balance $N_2$) prior to analysis. In a typical experiment, NO-releasing HA (~1 mg) was dissolved in 30 mL of deoxygenated PBS (10 mM, pH 7.4, 37° C.). The solution was purged with nitrogen gas at a flow rate of 200 mL $min^{-1}$ to carry liberated NO to the instrument. Analysis was terminated when NO levels fell below the detection limit of the instrument (10 ppb NO $mg^{-1}$ HA). Analysis of nitric oxide-release properties of the NO-releasing hyaluronic acid is set forth in Table 2 and FIG. 7. Analysis of control NO-release properties of unmodified hyaluronic acid and primary amine-modified hyaluronic acid is set forth in Table 3.

MALS, where measurements were conducted in 0.1 M phosphate buffer (pH 7.4) containing 0.1 M sodium nitrate and 0.02 wt % sodium azide.

Exemplary Synthesis Method

Example 2: Carboxymethylcellulose Scaffolds

These examples pertain to the synthesis of N-diazeniumdiolate functionalized nitric oxide (NO)-releasing carboxymethylcellulose with tunable NO storage and release kinetics. This embodiment has the following features, advantages, and/or uses. The water solubility and biocompatibility of this scaffold is high at high molecular weight of the NO-release scaffold.

In several embodiments, this scaffold may be useful in the treatment of bacterial infections.

TABLE 2

Nitric oxide-release properties of NO-releasing hyaluronic acid in PBS (10 mM, pH 7.4, 37° C.).[a]

| Modification | $[NO]_t$ ($\mu mol\ mg^{-1}$)[b] | $[NO]_{max}$ ($ppb\ mg^{-1}$)[c] | $t_{1/2}$ (min)[d] | $t_d$ (h)[e] | $[NO]_{t,\ 4\ h}$ ($\mu mol\ mg^{-1}$)[f] |
|---|---|---|---|---|---|
| HA6-PAPA/NO | 0.46 ± 0.02 | 9440 ± 1450 | 5 ± 1 | 8.4 ± 0.7 | 0.43 ± 0.02 |
| HA6-HEDA/NO | 0.53 ± 0.08 | 7060 ± 1350 | 10 ± 3 | 7.4 ± 1.8 | 0.50 ± 0.06 |
| HA6-DPTA/NO | 0.53 ± 0.11 | 4470 ± 1680 | 21 ± 8 | 11.2 ± 2.2 | 0.48 ± 0.09 |
| HA6-DETA/NO | 0.46 ± 0.11 | 4610 ± 1390 | 61 ± 15 | 16.3 ± 3.3 | 0.35 ± 0.08 |
| HA90-PAPA/NO | 0.29 ± 0.05 | 5150 ± 1860 | 7 ± 2 | 3.4 ± 0.7 | 0.29 ± 0.05 |
| HA90-HEDA/NO | 0.40 ± 0.08 | 3450 ± 840 | 13 ± 4 | 6.4 ± 1.5 | 0.39 ± 0.08 |
| HA90-DPTA/NO | 0.39 ± 0.06 | 1700 ± 390 | 28 ± 8 | 8.1 ± 0.5 | 0.36 ± 0.05 |
| HA90-DETA/NO | 0.32 ± 0.07 | 1970 ± 580 | 64 ± 20 | 14.1 ± 3.7 | 0.23 ± 0.03 |

[a]Error represents the standard deviation for n ≥ 3 separate syntheses.
[b]Total NO released over full duration.
[c]Maximum instantaneous NO concentration.
[d]Half-life of NO release.
[e]Duration of NO release.
[f]Total NO released over 4 h.

TABLE 3

Elemental analysis and nitric oxide release-properties of bare and ethylenediamine-modified 6 kDa and 90 kDa hyaluronic acid following exposure to 20 bar NO gas under basic conditions.[a]

| Modification | % N | $[NO]_t$ ($\mu mol\ mg^{-1}$)[b] |
|---|---|---|
| HA6 | 3.0 ± 0.1 | 0.13 ± 0.00 |
| HA6-EDA | 9.4 ± 0.3 | 0.23 ± 0.04 |
| HA90 | 3.0 ± 0.0 | 0.00 ± 0.00 |
| HA90-EDA | 8.6 ± 0.1 | 0.13 ± 0.02 |

[a]Error represents standard deviation for n ≥ 3 separate syntheses.
[b]Measured via chemiluminescence in phosphate buffered saline (10 mM, pH 7.4, 37° C.).

Enzymatic degradation of alkylamine-modified and NO-releasing HA. Enzymatic degradation of hyaluronic acid was carried out using a procedure adapted from Turner et al. Briefly, 50 mg of HA90, amine-modified HA90, or NO-releasing HA90 was dissolved in 5 mL of pH 5.0 buffer containing 0.15 M NaCl, 0.1 M $CH_3COONa$, and 1 mM $Na_2EDTA$ at 37° C. for 30 min with magnetic stirring. Hyaluronidase (2.5 mg) was dissolved in 1 mL of the same buffer and added directly to the HA solution. The mixture was incubated at 37° C. with vigorous stirring for 30 min. Following digestion, the reaction was terminated by placing the vial in a boiling water bath for 10 min, and then the solution was cooled to room temperature. Insoluble enzyme fragments were removed via centrifugation (7500 rpm, 15 min). The supernatant was filtered and analyzed via GPC- Periodontal diseases encompass a class of inflammatory infections of the gums and surrounding tissue affecting a significant portion of the population. Disease progression is caused by a shift in the microbial composition of healthy dental plaque biofilms resulting in an overabundance of Gram-negative bacteria. The Gram-negative bacteria, such as *Porphyromonas gingivalis*, induce inflammation in dental tissue (e.g., gums, periodontal ligaments, and alveolar bone tissue) leading to the development of periodontal pockets in which these bacteria can continue to thrive. If left untreated, chronic periodontitis eventually results in oral tissue degradation including tooth and bone resorption. Furthermore, studies have shown connections between periodontitis and other systemic inflammatory conditions including cardiovascular disease, coronary heart disease, and adverse pregnancy outcomes, attributable to the spread of pathogenic gram-negative oral bacteria to the bloodstream and other areas of the body.

The primary treatment for periodontal disease is scaling and root planing (SRP), a process of physically scraping dental plaque from the tooth surface. While this is effective at removing much of the plaque, it neither directly kills pathogenic bacteria nor prevents recolonization of the tooth surface. For this reason, patients with severe chronic periodontitis often receive SRP along with adjunct antibacterial therapies. Antibacterial implants incorporating drugs such as chlorhexidine, one of the most commonly prescribed oral antibacterial agents, have been used for such purposes but face a host of issues impacting their effectiveness. Undesirable side effects of chlorhexidine, including tooth and gum discoloration, altered taste, and toxicity toward healthy cells, can inhibit its utility and hinder patient compliance. Further, localized drug delivery to the periodontal pocket can be challenging due to gingival crevicular fluid (GCF) flow which constantly displaces fluid from the periodontal pocket into the oral cavity. As a result, there is a need for both potent antibacterial agents with limited side effects and materials capable of delivering antibacterial agents to the periodontal pocket to effectively eradicate periodontal pathogens.

Nitric oxide (NO) is an endogenous antibacterial agent that plays a key role in the mammalian immune response. It demonstrates broad spectrum antibacterial activity due to its multitude of killing mechanisms involving the formation of reactive byproducts capable of exerting both nitrosative and oxidative stress on bacteria. As a result, NO is less likely to foster bacterial resistance than many conventional antibacterial agents. Challenges in effective localized delivery of gaseous NO have necessitated the development of NO donors capable of storing and releasing nitric oxide. Among the numerous NO donors that have been developed, N-diazeniumdiolates represent an attractive option for dental therapeutics due to their proton-mediated release of NO in aqueous environments. With release kinetics dependent on external conditions (i.e., pH and temperature) and the chemical structure of the NO donor itself, a range of kinetic profiles can be realized. Furthermore, the ability to modify secondary amine-containing structures to impart NO-release is advantageous as the resulting material is capable of acting as both the delivery scaffold and the therapeutic agent. Thus, a structure possessing the desired properties for localizing delivery of NO to the periodontal pocket can be designed.

Carboxymethylcellulose (CMC), a water-soluble synthetic derivative of cellulose, is an attractive scaffold for use in the periodontal pocket due to its biocompatibility, adhesivity, and high solution viscosity. It has been widely used as a thickening and stabilizing additive in many industries and has also seen utility in dental applications. Thus, CMC can enhance retention in the periodontal pocket while its water-solubility enables natural clearance over time. Further, CMC can be produced with a range of molecular weights and degrees of substitution, enabling additional tunability toward its intended end use. The presence of carboxylic acid moieties allows for effective modification of the polymer in aqueous solution under mild reaction conditions, which is critical to impart antibacterial properties to the scaffold.

In order to form N-diazeniumdiolate NO donors on the CMC polymer backbone, it must be chemically modified with secondary amine moieties. Carbodiimide crosslinking reactions using EDC and NHS are effective for aqueous modifications of carboxylic acid-containing polysaccharides as demonstrated previously, enabling modification of CMC with four alkylamines (Scheme 2A). After secondary amine modification, N-diazeniumdiolates can be formed by exposing the polymer to high pressures of gaseous NO under basic conditions (Scheme 2B).

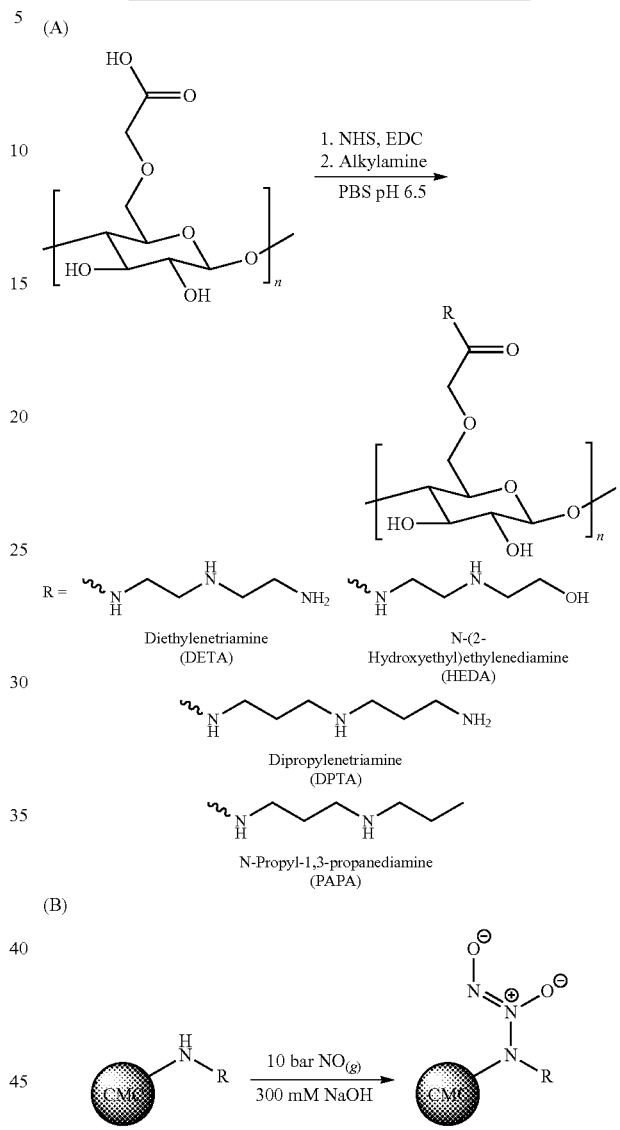

Scheme 2.
(A) Modification of CMC with alkylamines and
(B) N-diazeniumdiolate formation on CMC-amines.

Synthesis Details:

Materials and Methods—Carboxymethylcellulose (CMC, Mw 90 kDa, DS=0.7), diethylenetriamine (DETA), bis(3-aminopropyl)amine (DPTA), N-(2-hydroxyethyl)ethylenediamine (HEDA), N-propyl-1,3-propanediamine (PAPA), 1-Ethyl-3-(3-dimethylaminopropyl)carbodiimide (EDC), and N-hydroxysuccinimide (NHS) were purchased from Millipore Sigma (St. Louis, MO). *Aggregatibacter actinomycetemcomitans* (ATCC #43717) was purchased from the American Type Culture Collection (Manassas, VA). *Porphyromonas gingivalis* strain A7436 was provided by the UNC School of Dentistry, Chapel Hill, NC Brain heart infusion (BHI) broth and agar, CDC anaerobe 5 vol % sheep blood agar, and GasPak EZ campy sachets were purchased from Becton, Dickinson, and Company (Franklin Lakes, NJ). Wilkins-Chalgren (W—C) broth was purchased from Thermo Fisher Scientific (Waltham, MA). Human gingival fibroblasts (HGF-1) and FibroLife S2 media were purchased from Lifeline Cell Technology LLC (Frederick, MD). Pure nitric oxide (99.5%), argon, nitrogen, nitric oxide calibration gases (25.87 ppm in nitrogen), and anaerobic gas mixture (10% hydrogen, 5% carbon dioxide, balance nitrogen) were purchased from Airgas (Durham, NC). MTS reagent was purchased from BioVision (Milpitas, CA) and phenazine methosulfate (PMS) was purchased from Millipore Sigma. Common laboratory salts and solvents were purchased from Thermo Fisher Scientific (Waltham, MA).

Synthesis of amine-modified carboxymethylcellulose. Solutions of CMC were first prepared by dissolving 100 mg 90 kDa CMC in 10 mL pH 6.5 phosphate buffered saline (10 mM PBS 6.5). After fully dissolving the solid with magnetic stirring, a 5:1 molar excess of NHS, relative to the number of carboxylates on CMC, was added followed by an equivalent molar excess of EDC. The mixture was stirred for 20 minutes before the respective alkylamine was added as a bolus at a 1:1 molar ratio to EDC. Solutions were stirred overnight (16 h) and then transferred into dialysis tubing (MWCO 10 kDa) and dialyzed against deionized water for 3 d with frequent water changes. The final solutions were transferred into plastic tubes, frozen at −80° C., and freeze dried on a Labconco FreeZone −50° C. lyophilizer (Labconco, Kansas City, MO) to yield a fibrous white solid.

Formation of amine bonds were qualitatively confirmed using a Perkin Elmer Spectrum 100 FTIR (Perkin Elmer, Waltham, MA) and modification efficiencies were quantified with a Perkin Elmer Series II CHNS/O Analyzer (Perkin Elmer, Waltham, MA). Molecular weights were determined using a Breeze 2 size exclusion chromatography instrument (Waters, Milford, MA) coupled with a 2414 refractive index detector (Waters, Milford, MA) and miniDAWN TREOS multi-angle light scattering detector (Wyatt Technology, Santa Barbara, CA). Briefly, 0.1 wt. % solutions of CMC were prepared in the mobile phase buffer consisting of 0.1 M acetate (pH 4.6) with 0.1 M NaNO3 and 0.02 wt % NaN3. A 50 μL aliquot of each sample was injected and run through two columns in series (2× Shodex OHpak LB804, Showa Denko America, New York, NY) at a flow rate of 0.6 mL min-1.

Synthesis of N-diazeniumdiolate-modified carboxymethylcellulose. Solutions of amine-modified CMC were prepared at 2 wt. % in 300 mM NaOH. The solutions were placed in a Parr hydrogenation reactor and purged with argon six times (three short purges followed by three 10-minute purges) before being pressurized with 10 bar NO gas for 3 d. The reaction chamber was then purged again six times with argon and the N-diazeniumdiolate-modified CMC was precipitated in cold ethanol and dried under reduced pressure. All NO-releasing samples were stored at −20° C. prior to use.

Nitric oxide release from CMC scaffolds was characterized using a Zysense 280i Nitric Oxide Analyzer (NOA, Zysense, Frederick, CO). In a typical experiment, 1 mg NO-releasing sample was submerged in 25 mL deoxygenated PBS (10 mM, pH 7.4, 37° C.). Nitrogen gas was flowed through the solution at 200 mL min-1 to transport NO released from the scaffold to the NOA. Release was measured until NO levels fell below 10 ppb NO per mg scaffold.

Analysis of the Synthesized CMC Scaffolds:

Four different amine-modified CMCs were prepared through aqueous carbodiimide crosslinking reactions between 90 kDa CMC and small molecule amines. Reaction of CMC with diethylenetriamine (DETA), bis(3-aminopropyl)amine (DPTA), N-(2-hydroxyethyl)ethylenediamine (HEDA), and N-propyl-1,3-propanediamine (PAPA) produced CMC-DETA, CMC-DPTA, CMC-HEDA, and CMC-PAPA, respectively.

Figure 8:
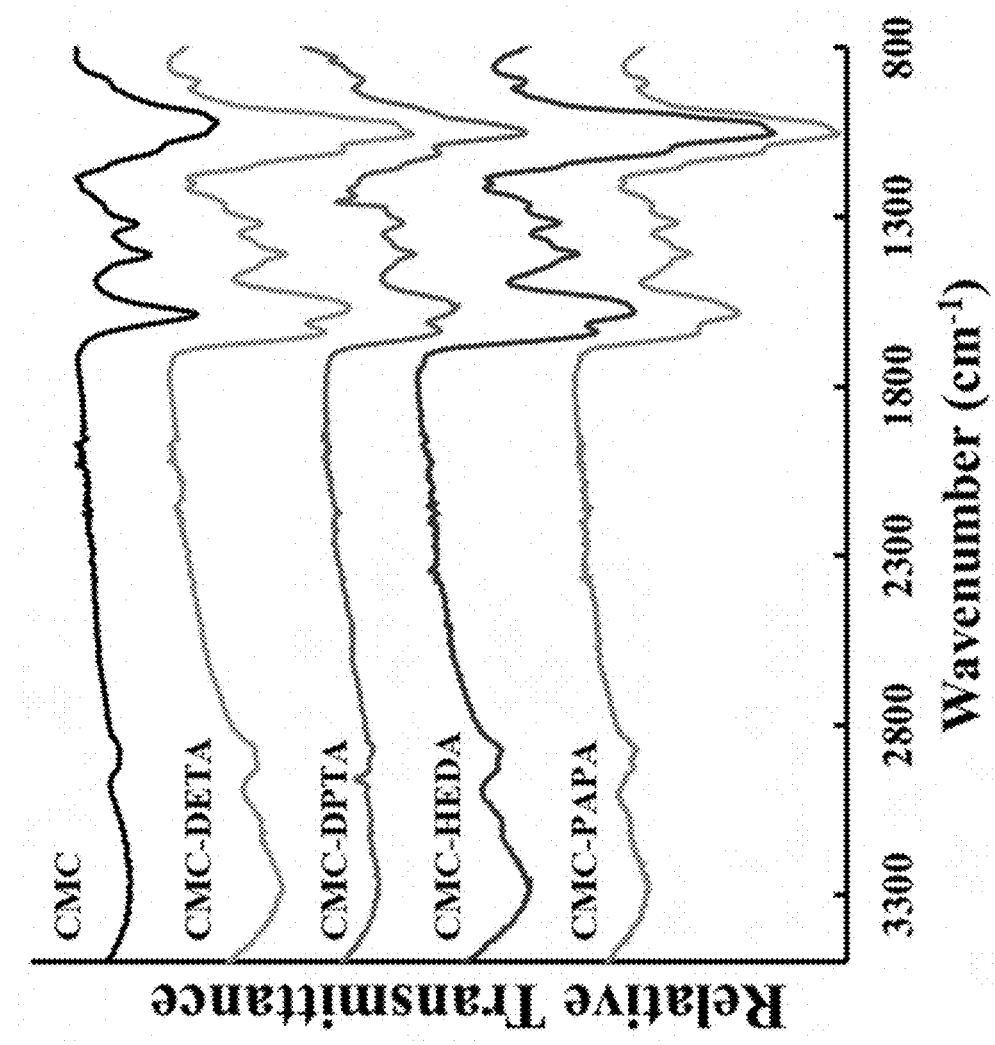
FIG. 8 shows FTIR spectra of unmodified and amine-modified CMC scaffolds.

In order to qualitatively determine the successful amine conjugation, CMC-amines were analyzed using FTIR spectroscopy (FIG. 8). Unmodified CMC displays a single peak at 1590 cm$^{-1}$, indicative of a carbonyl C=O stretch. Upon modification with each amine sample, the singular carbonyl stretching signal is overtaken by two new peaks emerging at 1560 cm$^{-1}$ and 1630 cm$^{-1}$, characteristic of N—H bending and C=O stretching, respectively. While this FTIR analysis supports that amide bonds were formed and thus the amines were successfully conjugated to CMC, elemental analysis was required in order to quantify the extent of modification. Determination of the nitrogen percentage within each sample using a CHNS/O elemental analyzer enabled an estimate of carboxylate modification of the CMC backbone in addition to primary amine content (only for DETA and DPTA since HEDA and PAPA lack an additional primary amine after modification) as shown in Table 4. Notably, the modification efficiencies remained relatively consistent despite differences in the amine identities.

TABLE 4

Extent of CMC modification from CHN elemental analysis

| Sample | % N | % COOH modified | Primary amine content (μmol mg$^{-1}$) |
|---|---|---|---|
| CMC-DETA | 7.11 ± 0.22 | 63 ± 2 | 1.69 ± 0.05 |
| CMC-DPTA | 7.11 ± 0.92 | 68 ± 9 | 1.69 ± 0.22 |
| CMC-HEDA | 6.99 ± 0.28 | 67 ± 3 | 0 |
| CMC-PAPA | 7.04 ± 0.25 | 59 ± 2 | 0 |

Next, the molecular weights ($M_w$) of each scaffold were determined with SEC-MALS and compared with theoretical $M_w$ calculated based on elemental analysis (Table 5).

TABLE 5

Molecular weights ($M_w$) of scaffold compared with theoretical $M_w$

| Sample | Theoretical $M_w$ (kDa)$^a$ | Measured $M_w$ (kDa)$^b$ | Đ$^b$ |
|---|---|---|---|
| CMC | 90,000 | 86,450 | 2.39 |
| CMC-DETA | 110,400 | 155,600 | 2.20 |
| CMC-DPTA | 117,900 | 116,100 | 1.86 |
| CMC-HEDA | 111,700 | 139,700 | 1.30 |
| CMC-PAPA | 111,800 | 105,100 | 1.59 |

Figure 21:
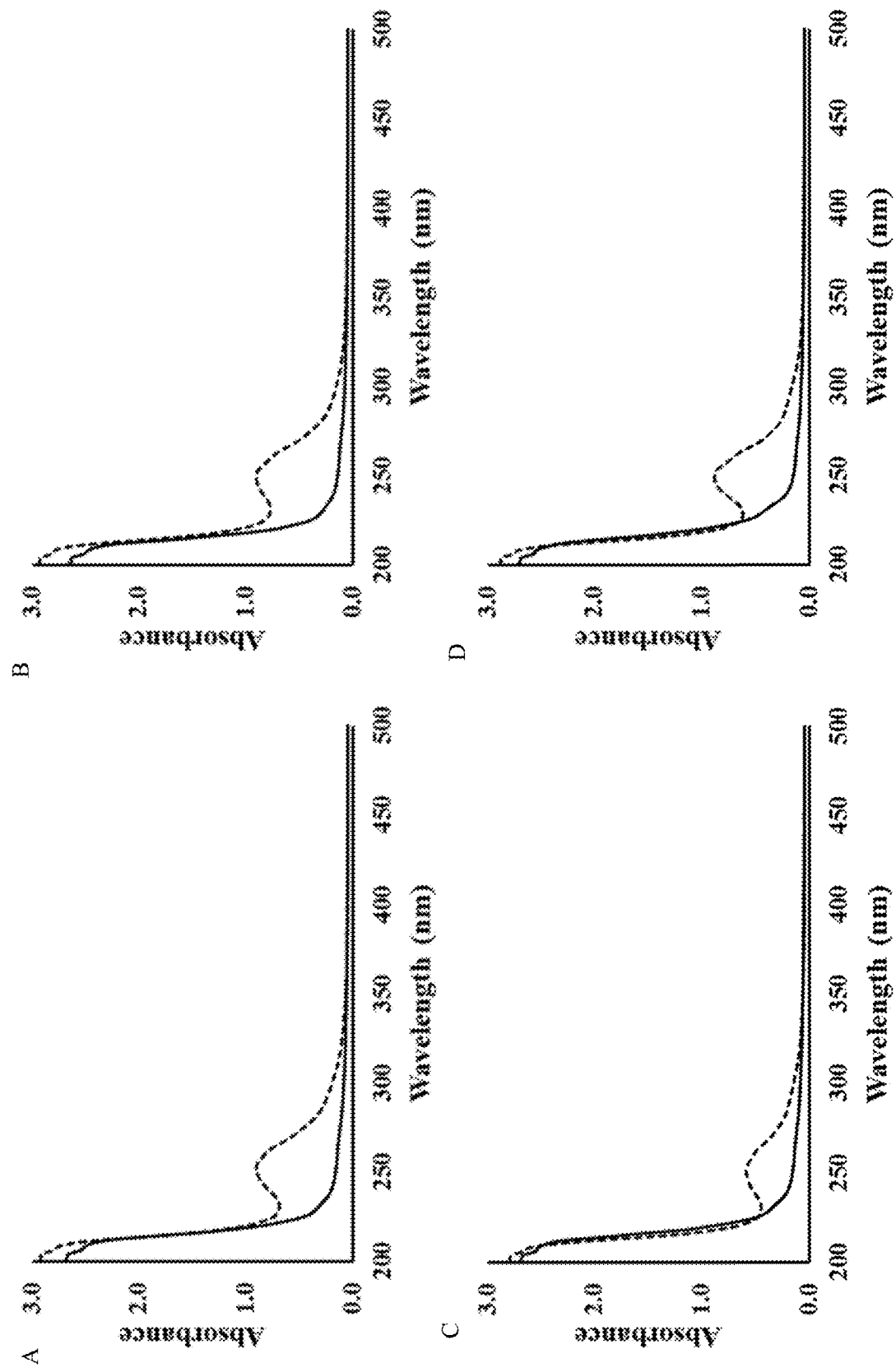
FIG. 21 shows UV-vis absorption spectra of A) CMC-DETA (solid line) and CMC-DETA/NO (dashed line), B) CMC-DPTA (solid line) and CMC-DPTA/NO (dashed line), C) CMC-HEDA (solid line) and CMC-HEDA/NO (dashed line), and D) CMC-PAPA (solid line) and CMC-PAPA/NO (dashed line), in 50 mM NaOH.

A clear increase in $M_w$ was observed for all CMC-amines relative to the unmodified biopolymer. For CMC-DETA, the experimentally determined $M_w$ was much higher than the theoretical, likely indicative of some crosslinking due to the presence of two reactive amine end groups. However, a similar increase is not observed for DPTA, also possessing two amine end groups, possibly as a result of higher steric hindrance resulting from its greater molar mass. The increased $M_w$ for CMC-HEDA was attributed to stronger hydrogen bonding originating from the hydroxyl end groups. Surprisingly, dispersity of the samples decreased after modification, potentially as a result of sample interactions arising from the introduction of cationic charges onto the polymer backbone. Nitric oxide-release capabilities were imparted onto CMC-amines through the formation of N-diazeniumdiolates. These modifications were achieved by reacting the scaffolds with pressurized (10 bar) NO gas in basic aqueous solution for 3 d. Successful N-diazeniumdiolate formation was confirmed using UV-vis spectroscopy in order to verify the presence of a characteristic absorbance peak at 250 nm (FIG. 21). Further, NO release characteristics were determined in real-time using a chemiluminescence-based nitric oxide analyzer. The full extent of NO release characterization under physiological conditions (37° C., pH 7.4), shown in Table 6, demonstrates the range of kinetics attainable for CMC-amines as a function of the chemical structure of the amine modification. CMC-DETA/NO possesses the longest half-life (~3 h) as a result of primary amine stabilization of diazeniumdiolate stemming from intramolecular ring formation. CMC-DPTA/NO has similar primary amine interaction with the diazeniumdiolate, but its longer chain length results in a less favorable intramolecular stabilization and thus has a shorter NO-release half-life. Interestingly, CMC-HEDA/NO has a similar half-life to that of CMC-DPTA/NO despite the lack of a primary amine. This is attributed to both stronger hydrogen bonding between the primary hydroxyl group and the diazeniumdiolate relative to a primary amine and HEDA having a more similar alkyl chain length to DETA. Finally, with its alkyl terminal group having very little interaction with the NO-releasing moiety, CMC-PAPA/NO demonstrated the most rapid NO release of the four systems.

TABLE 6

Characterization of nitric oxide release from N-diazeniumdiolate-modified CMCs

| Sample | t[NO]$^a$ (μmol mg$^{-1}$) | $t_{1/2}$$^b$ (min) | $t_d$$^c$ (h) |
|---|---|---|---|
| CMC-DETA/NO | 0.29 ± 0.07 | 179.0 ± 6.2 | 11.6 ± 2.1 |
| CMC-DPTA/NO | 0.27 ± 0.05 | 24.0 ± 2.6 | 6.7 ± 1.9 |
| CMC-HEDA/NO | 0.45 ± 0.03 | 25.0 ± 5.4 | 4.6 ± 0.2 |
| CMC-PAPA/NO | 0.38 ± 0.11 | 11.3 ± 2.4 | 2.2 ± 0.8 |

$^a$Total amount of NO released from the scaffold.
$^b$Half-life of NO release.
$^c$Duration of NO release before reaching 10 ppb mg$^{-1}$.

Exemplary Method of Using

Example 3A—Hyaluronic Acid Scaffolds

The following examples pertain to the use of N-diazeniumdiolate functionalized nitric oxide (NO)-releasing hyaluronic acid as antibacterial agent in, for example, wound healing. The scaffolds generated in Example 1 are used in the following experiments against various bacterial cultures:

Planktonic bactericidal assay. Bacterial cultures of *P. aeruginosa*, *E. coli*, *E. faecalis*, *S. aureus*, multidrug-resistant (MDR) *P. aeruginosa*, and methicillin-resistant *S. aureus* were grown from frozen (−80° C.) stocks overnight in TSB (3 mL) at 37° C. An aliquot (1 mL) of the overnight solution was recultured in fresh TSB (50 mL) to a concentration of 10$^8$ CFU mL$^{-1}$ and subsequently diluted to 10$^6$ CFU mL$^{-1}$ in PBS (10 mM, pH 7.4). Weighed samples of control (non-NO-releasing) HA, NO-releasing HA, or neomycin sulfate were dissolved in PBS and titrated with 1 M HCl to adjust the pH to 7.4. Samples were added to a 96-well polystyrene plate and serially diluted in PBS so that each well contained 100 μL of control HA, NO-releasing HA, or neomycin. Bacterial solution containing 10$^6$ CFU mL$^{-1}$ (100 μL; 1 vol % TSB supplemented PBS) was added to each well, giving final HA concentrations in the range of 0.25 to 32 mg mL$^{-1}$ or neomycin concentrations from 0.5 to 1024 μg mL$^{-1}$. The 96-well plate was then incubated at 37° C. for 4 h with gentle shaking. Untreated bacterial solutions were included in each experiment to ensure bacteria viability over the 4 h duration. After the 4 h exposure, bacterial solutions were serially diluted (10-, 100-, and 1000-fold dilutions), spiral plated on TSA plates using an Eddy Jet spiral plater (IUL; Farmingdale, NY), and incubated overnight at 37° C. Viability of bacteria following treatment with HA or neomycin was determined using a Flash & Go colony counter (IUL; Farmingdale, NY). The minimum bactericidal concentration after a 4 h exposure period (MBC$_{4h}$) was defined as the minimum concentration required to achieve a 3-log reduction (≥99.9% reduction) in bacterial viability relative to untreated bacteria (i.e., reduced bacterial counts from 10$^6$ to 10$^3$ CFU mL$^{-1}$). The limit of detection for this counting method is 2.5×10$^3$ CFU mL$^{-1}$. The NO dose required for bactericidal action was calculated by multiplying the MBC$_4$h of the NO-releasing HA samples (mg mL$^{-1}$) with the total NO released in PBS (pH 7.4; μmol NO mg$^{-1}$ HA) at 4 h. The minimum bactericidal concentrations (MBC$_4$h) of NO-releasing hyaluronic acid against various bacteria are set forth in Tables 7 and 9. DPTA-modified HA eradicates all bacteria strains at a dose of ≤2 mg mL$^{-1}$. The doses of NO or neomycin required to elicit a 3-log reduction in bacteria viability following 4 h treatment is set forth in Tables 8 and 10. The antibacterial efficacy of active ingredients NO-releasing hyaluronic acids against the various bacteria are set forth in FIGS. 10 and 13-15. NO is bactericidal against antibiotic-resistant bacteria at low concentrations. All data presented are from n≥3 separate experiments.

TABLE 7

Minimum bactericidal concentrations (MBC$_{4\ h}$) of NO-releasing hyaluronic acid against Gram-negative (*E. coli* and *P. aeruginosa*) and Gram-positive (*S. aureus* and *E. faecalis*) bacteria.$^a$

| | MBC$_{4\ h}$ (mg mL$^{-1}$) | | | |
|---|---|---|---|---|
| Modification | *E. coli* | *P. aeruginosa* | *S. aureus* | *E. faecalis* |
| HA6-PAPA/NO | 0.5 | 1 | 4 | 8 |
| HA6-HEDA/NO | 2 | 2 | 8 | 16 |
| HA6-DPTA/NO | 1 | 1 | 2 | 2 |
| HA6-DETA/NO | 2 | 2 | 16 | 32 |
| HA90-PAPA/NO | 1 | 2 | 8 | >32 |
| HA90-HEDA/NO | 4 | 4 | >32 | >32 |
| HA90-DPTA/NO | 1 | 2 | 2 | 2 |
| HA90-DETA/NO | 8 | 4 | 32 | >32 |

$^a$MBC$_{4\ h}$ determined from n ≥ 3 experiments.

TABLE 8

Doses of NO required to elicit a 3-log reduction in bacteria viability following 4 h treatment to NO-releasing hyaluronic acid.

| | NO Dose (μg mL$^{-1}$)$^a$ | | | |
|---|---|---|---|---|
| Modification | *E. coli* | *P. aeruginosa* | *S. aureus* | *E. faecalis* |
| HA6-PAPA/NO | 7 ± 1 | 13 ± 1 | 52 ± 2 | 103 ± 5 |
| HA6-HEDA/NO | 30 ± 4 | 30 ± 4 | 120 ± 14 | 240 ± 29 |
| HA6-DPTA/NO | 14 ± 3 | 14 ± 3 | 29 ± 5 | 29 ± 5 |
| HA6-DETA/NO | 21 ± 5 | 21 ± 5 | 168 ± 38 | 336 ± 77 |
| HA90-PAPA/NO | 9 ± 2 | 17 ± 3 | 70 ± 12 | N.D.$^b$ |
| HA90-HEDA/NO | 47 ± 10 | 47 ± 10 | N.D.$^b$ | N.D.$^b$ |
| HA90-DPTA/NO | 11 ± 2 | 22 ± 3 | 22 ± 3 | 22 ± 3 |
| HA90-DETA/NO | 55 ± 7 | 28 ± 4 | 221 ± 29 | N.D.$^b$ |

$^a$NO dose derived from the MBC$_{4\ h}$ and the total NO released over the 4 h exposure time in PBS (10 mM, pH 7.4, 37° C.).
$^b$NO dose could not be determined, as the MBC$_{4\ h}$ exceeded the highest HA concentration evaluated.

TABLE 9

Minimum bactericidal concentrations (MBC$_{4\,h}$) of NO-releasing DPTA-modified hyaluronic acid against antibiotic-resistant bacteria.[a]

| Modification | MBC$_{4\,h}$ (mg mL$^{-1}$) | |
|---|---|---|
| | MDR-*P. aeruginosa* | MRSA |
| HA6-DPTA/NO | 1 | 2 |
| HA90-DPTA/NO | 1 | 2 |

[a]MBC$_{4\,h}$ determined from n ≥ 3 experiments.

TABLE 10

Dose of neomycin required to elicit a 3-log reduction in planktonic bacteria viability following 4 h exposure.

| Bacteria | [Neomycin][a] (μg mL$^{-1}$) |
|---|---|
| *E. coli* | 1 |
| *P. aeruginosa* | 32 |
| *S. aureus* | 2 |
| *E. faecalis* | 64 |
| MDR-*P. aeruginosa* | 128 |
| MRSA | >1024 |

[a]Bactericidal neomycin dose determined from n ≥ 3 experiments.

Figure 9:
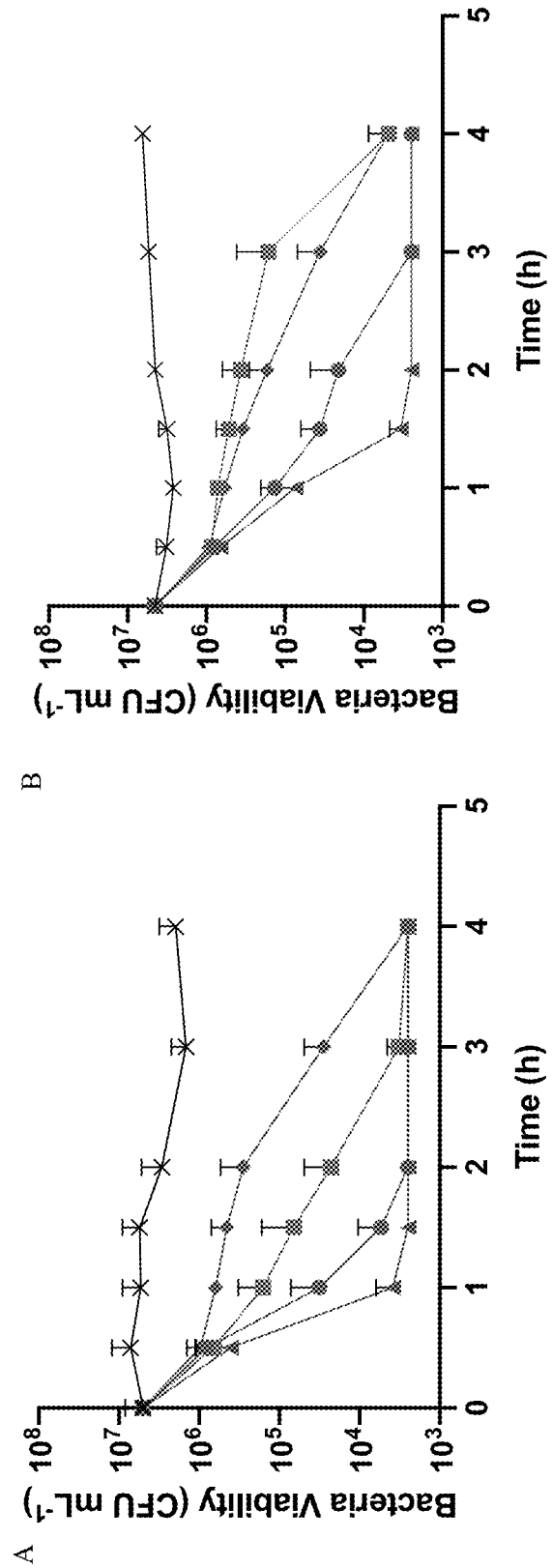
FIG. 9 shows time-based bactericidal assay of 6 kDa NO-releasing HA derivatives against (A) P. aeruginosa and (B) S. aureus. Treatments include HA6-PAPA/NO (blue circle), HA6-HEDA/NO (green square), HA6-DPTA/NO (red triangle), HA6-DETA/NO (purple diamond), and untreated (black cross). All HA derivatives were prepared at equivalent doses of 2 mg mL$^{-1}$ for P. aeruginosa eradication and 16 mg mL$^{-1}$ for S. aureus eradication.
Figure 10:
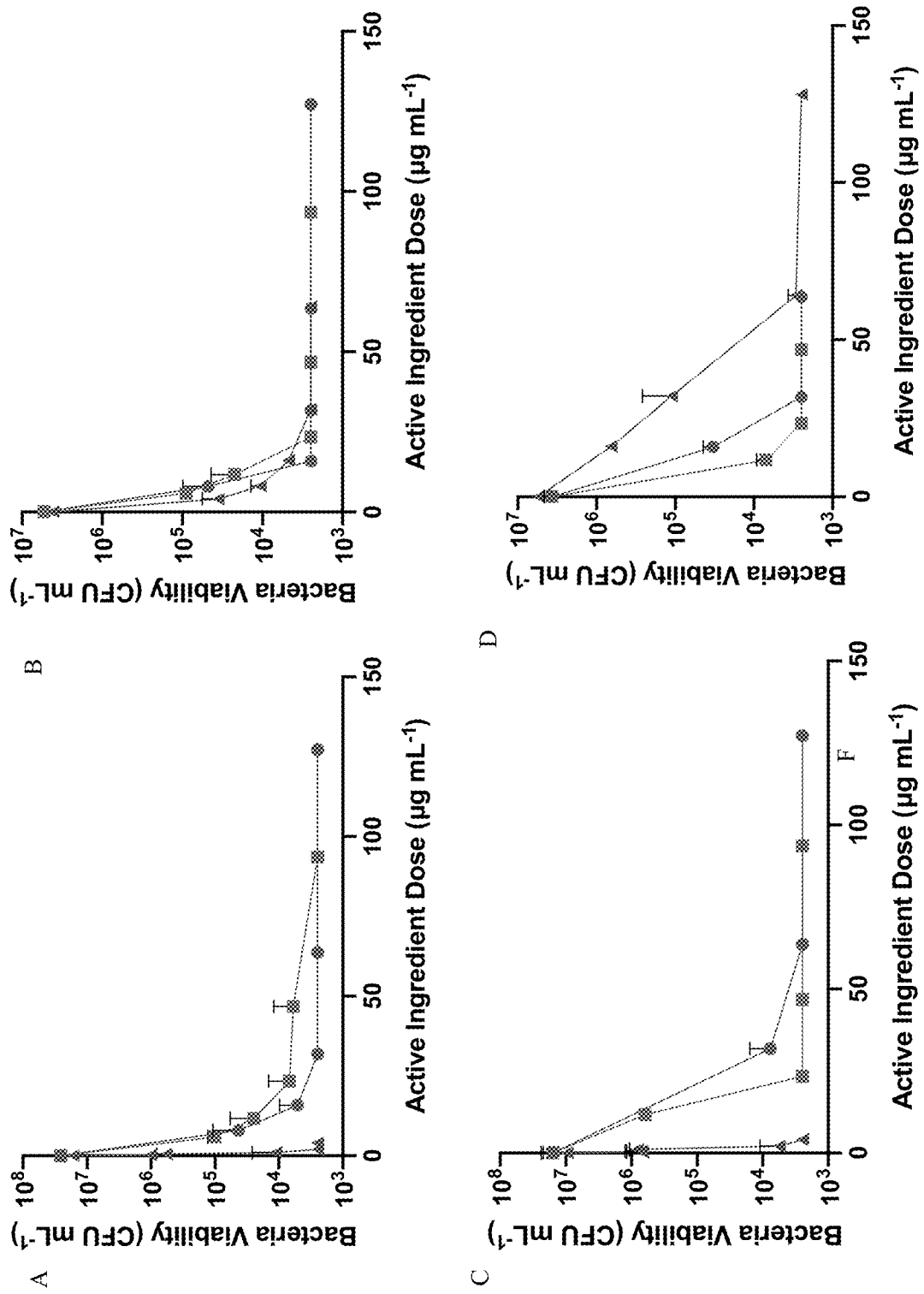
FIG. 10 shows antibacterial efficacy of active ingredient (neomycin or NO) against (A) E. coli, (B) P. aeruginosa, (C) S. aureus, (D) E. faecalis, (E) MDR-P. aeruginosa, and (F) MRSA following treatment with HA6-DPTA/NO (blue circle), HA90-DPTA/NO (green square), or neomycin sulfate (red triangle). The NO dose was calculated from the total NO released over the 4 h exposure time in PBS (10 mM, pH 7.4, 37° C.) for HA6-DPTA/NO and HA90-DPTA/NO.
Figure 10:
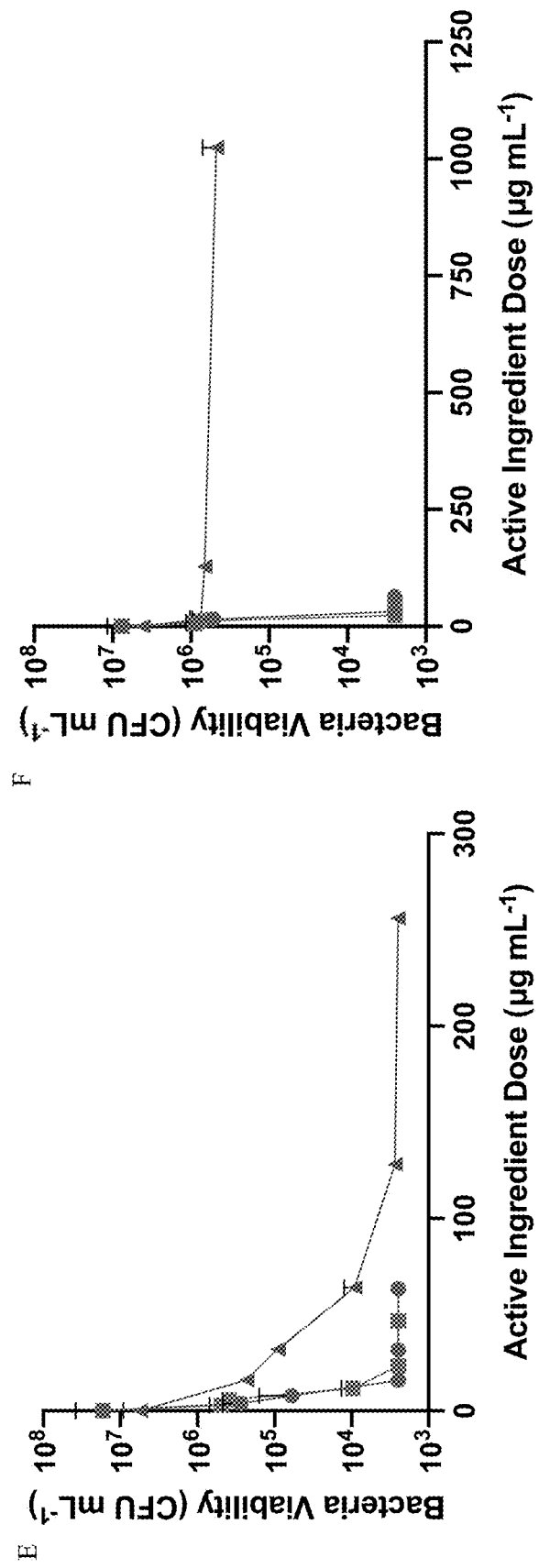

Time-based planktonic bactericidal assay. Bacteria solutions containing 10$^6$ CFU mL$^{-1}$ of *P. aeruginosa* and *S. aureus* were prepared as described for the 4 h planktonic bactericidal assay. Weighed samples of 6 kDa NO-releasing HA were dissolved at 4 mg mL$^{-1}$ or 32 mg mL$^{-1}$ (for *P. aeruginosa* and *S. aureus* treatment, respectively) in PBS and titrated with 1 M HCl to adjust the pH to 7.4. Equivalent volume of 10$^6$ CFU mL$^{-1}$ bacteria solution was added to each vial to bring the final concentration of NO-releasing HA to 2 mg mL$^{-1}$ or 16 mg mL$^{-1}$. Untreated bacteria solutions were included to ensure viability over the 4 h exposure period. The bacteria solutions were incubated at 37° C. with gentle shaking. At pre-determined time points (i.e., 0 h, 0.5 h, 1 h, 1.5 h, 2 h, 3 h, and 4 h), 100 μL aliquots of the bacteria solutions were removed and serially diluted (10- and 100-fold dilutions), plated on TSA plates using an Eddy Jet spiral plater, and incubated overnight at 37° C. Bacteria viability at each time point was determined using a Flash & Go colony counter. The time-based bactericidal assay results of NO-releasing HA derivatives against the bacteria are set forth in FIG. 9. HA-DPTA/NO eradicates bacteria quickly and at low concentrations.

Figure 11:
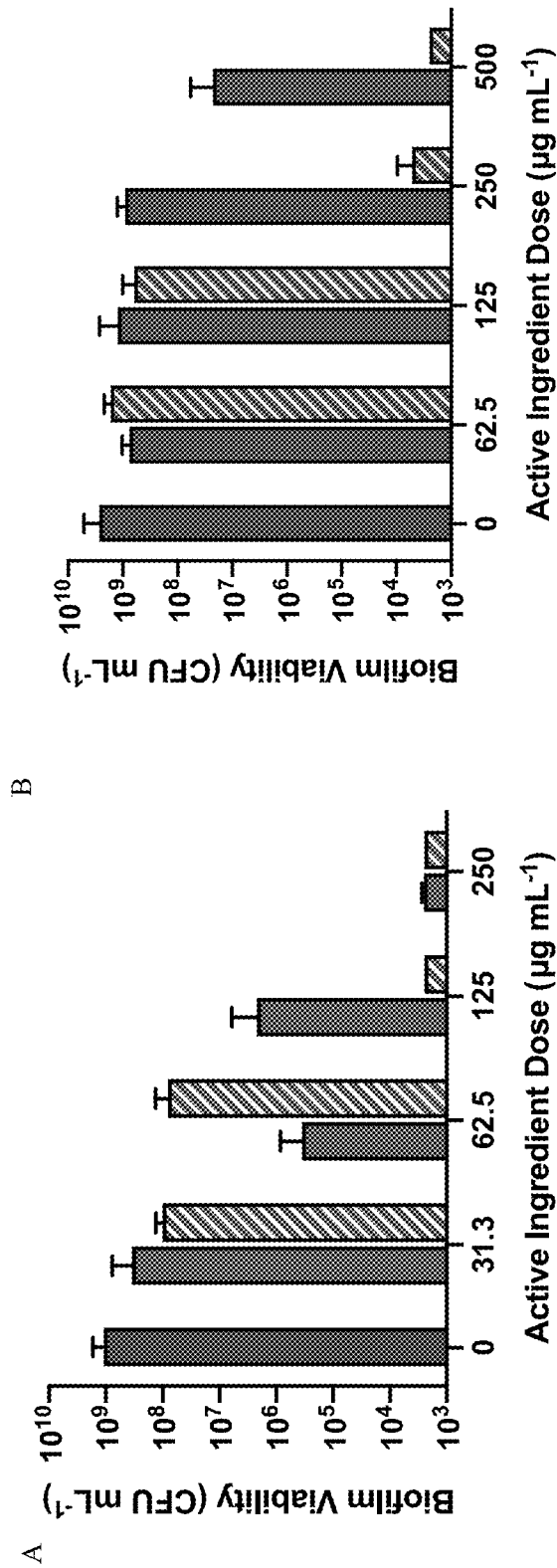
FIG. 11 shows biofilm viability following 24 h treatment of (A) P. aeruginosa and (B) MDR-P. aeruginosa pre-existing biofilms in solution with equivalent active ingredient doses of neomycin sulfate (solid) or HA6-DPTA/NO (striped).
Figure 16:
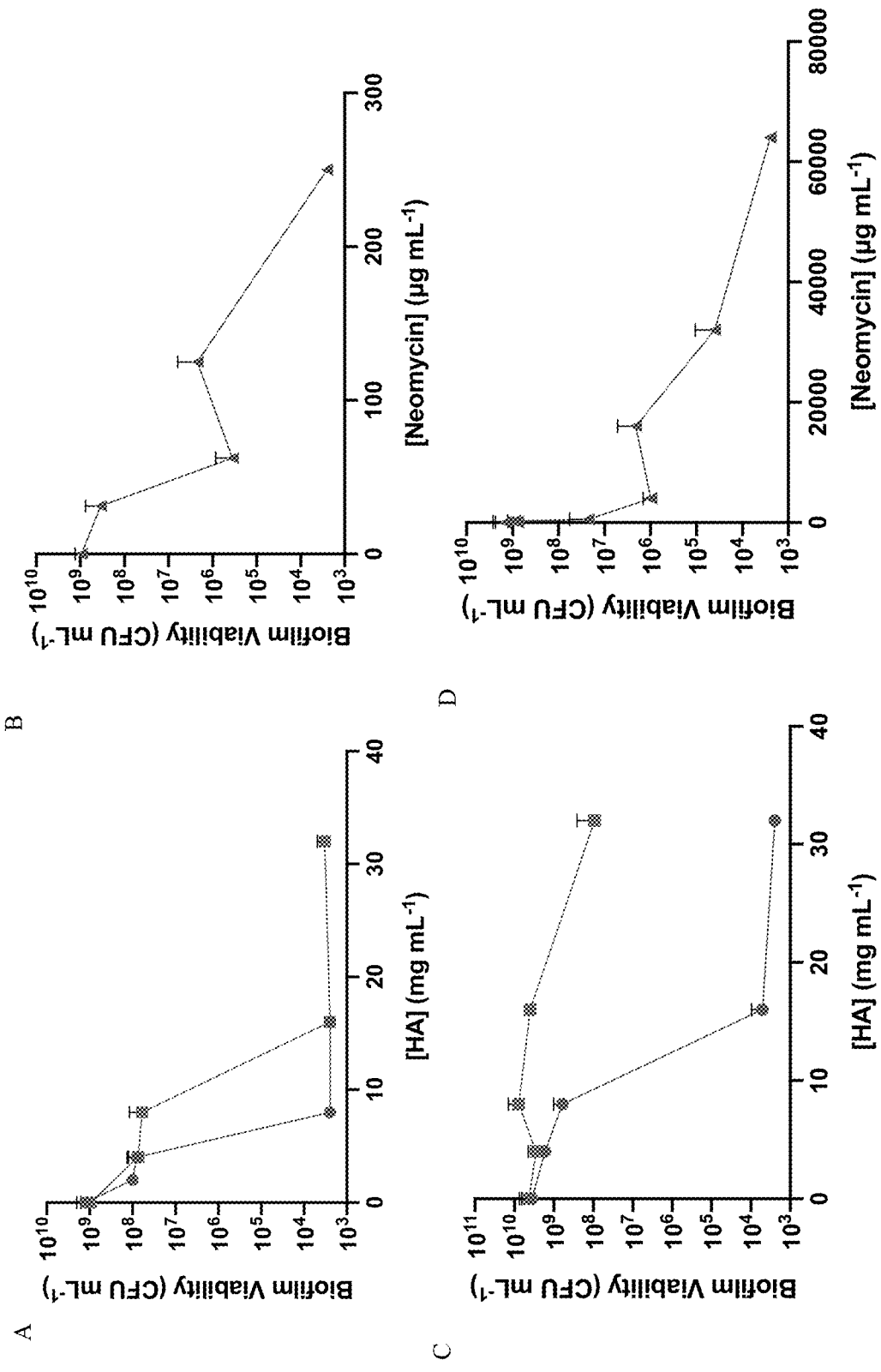
FIG. 16 shows antibiofilm efficacy of 6 and 90 kDa NO-releasing DPTA-modified HA against P. aeruginosa and MDR-P. aeruginosa biofilms. Biofilm viability following 24 h treatment of (A-B) P. aeruginosa and (C-D) MDR-P. aeruginosa biofilms with HA6-DPTA/NO (blue circle), HA90-DPTA/NO (green square), or neomycin sulfate (red triangle) is shown. Another figuration of the biofilm viability of 6 and 90 kDa NO-releasing DPTA-modified HA and neomycin against *P. aeruginosa* and MDR-*P. aeruginosa* biofilms is shown in (E) and (F).
Figure 16:
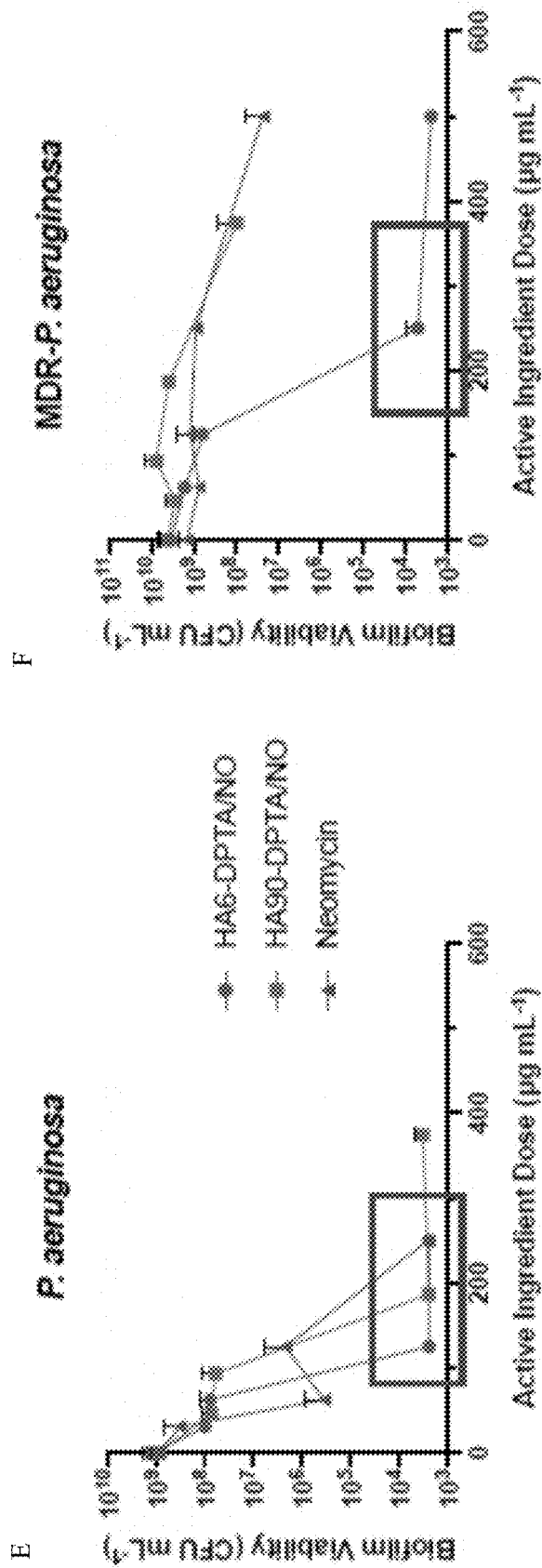
Figure 17:
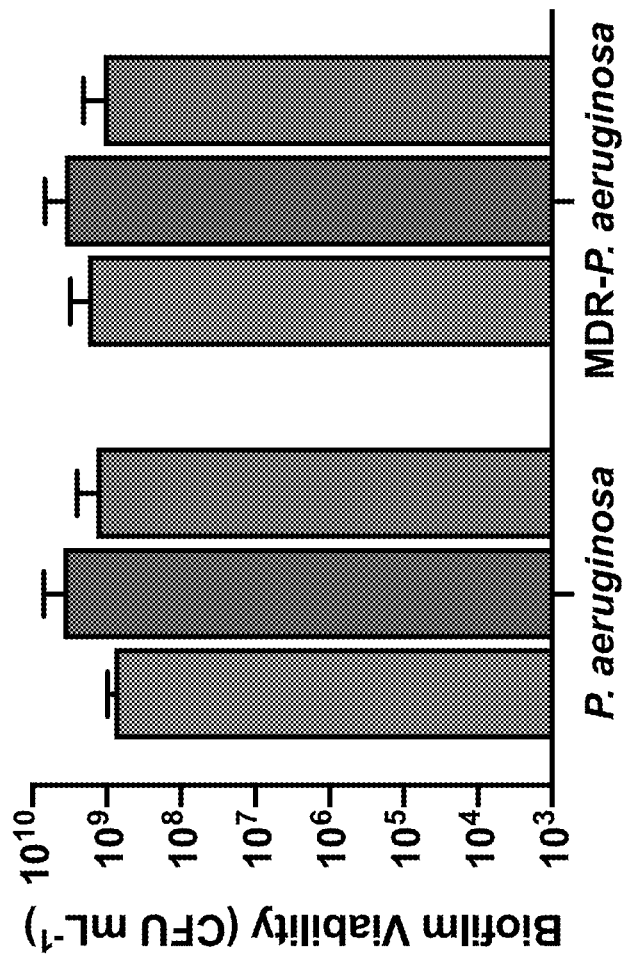
FIG. 17 shows biofilm viability following 24 h exposure of *P. aeruginosa* and MDR-*P. aeruginosa* biofilms to blank (left, gray), control HA6-DPTA (middle, blue), or control HA90-DPTA (right, green) solutions. Solutions of HA were prepared at the $MBEC_{24h}$ for the respective NO-releasing derivative. Of note, HA90-DPTA was prepared at 32 mg $mL^{-1}$ for testing of MDR-*P. aeruginosa* biofilms due to the lack of $MBEC_{24}h$ for the NO-releasing derivative.

Biofilm eradication assay. Bacterial cultures of *P. aeruginosa* and MDR-*P. aeruginosa* were grown from frozen (−80° C.) stocks overnight in TSB (3 mL) at 37° C. and recultured in fresh TSB to a concentration of 10$^8$ CFU mL$^{-1}$. An aliquot of the 10$^8$ solution (18 μL) was added to 1800 μL of fresh TSB in a 24-well polystyrene plate and incubated at 37° C. with gentle shaking for 72 h. Nitric oxide-releasing DPTA-modified HA or neomycin was dissolved in PBS (750 μL, pH 7.4, 10 mM) in 1-dram vials and adjusted to pH 7.4 with 1 M HCl. Biofilms (250 μL) were rinsed with PBS (pH 7.4, 10 mM) and added to the 1-dram vials. Treatment with 4-32 mg mL$^{-1}$ of NO-releasing DPTA-modified HA or 30-240 μg mL$^{-1}$ neomycin sulfate occurred for 24 h at 37° C. with gentle shaking. Untreated biofilms were included in each experiment to ensure biofilm viability over the 24 h duration. Following treatment, biofilms (100 μL) were diluted 10-fold and dispersed via pipetting and vortexing. Biofilm solutions were further diluted (1,000- and 100,000-fold), plated on TSA plates using an Eddy Jet spiral plater, and incubated overnight at 37° C. Biofilm viability following treatment with HA or neomycin was determined using a Flash & Go colony counter. The minimum biofilm eradication concentration after a 24 h exposure period (MBEC$_{24h}$) was defined as the minimum concentration required to achieve a 5-log reduction (≥99.999% reduction) in bacterial viability relative to untreated bacteria (i.e., reduced bacterial counts from 10$^8$ to 10$^3$ CFU mL$^{-1}$). The NO dose required for biofilm eradication was calculated by multiplying the MBEC$_{24h}$ of the NO-releasing HA samples (mg mL$^{-1}$) with the total NO released in pH 7.4 PBS (μmol NO mg$^{-1}$HA). The biofilm viability results after 24h treatment of bacteria pre-existing biofilms with neomycin sulfate or Nitric oxide-releasing DPTA-modified HA is set forth in FIGS. 11, 16, and 17. All data presented are from n≥3 separate experiments. Low molecular weight HA>high molecular weight HA NO>neomycin.

In vitro cytotoxicity assay. L929 murine fibroblasts were grown in DMEM supplemented with 10 vol % FBS and 1 wt % penicillin streptomycin. Cells were incubated in 5 vol % CO$_2$ under humidified conditions at 37° C. After reaching 80% confluency, cells were seeded onto 96-well polystyrene plates at a density of 1×10$^4$ cells well$^{-1}$. After 24 h incubation at 37° C., the supernatant was then aspirated and replaced with 100 μL of either control or NO-releasing HA in fresh grown medium with HA concentrations ranging from 0.25 to 32 mg mL$^{-1}$. The cultures were then incubated for 24 h at 37° C. Following exposure, the supernatant was aspirated, and the wells were washed twice with PBS. A 100 μL mixture of DMEM/MTS/PMS (105/20/1, v/v/v) was added to each well and incubated for 90 min at 37° C. The absorbance of the solution in each well was measured at 490 nm using a Molecular Devices SpectraMax M2 (San Jose, CA). A blank mixture of DMEM/MTS/PMS and untreated cells were used as the blank and control, respectively. Cell viability for each sample was calculated as follows:

$$\% \text{ cell viability} = \frac{(\text{Abs}_{490} - \text{Abs}_{blank})}{(\text{Abs}_{control} - \text{Abs}_{blank})} \times 100 \quad \text{(Eq. 2)}$$

Figure 12:
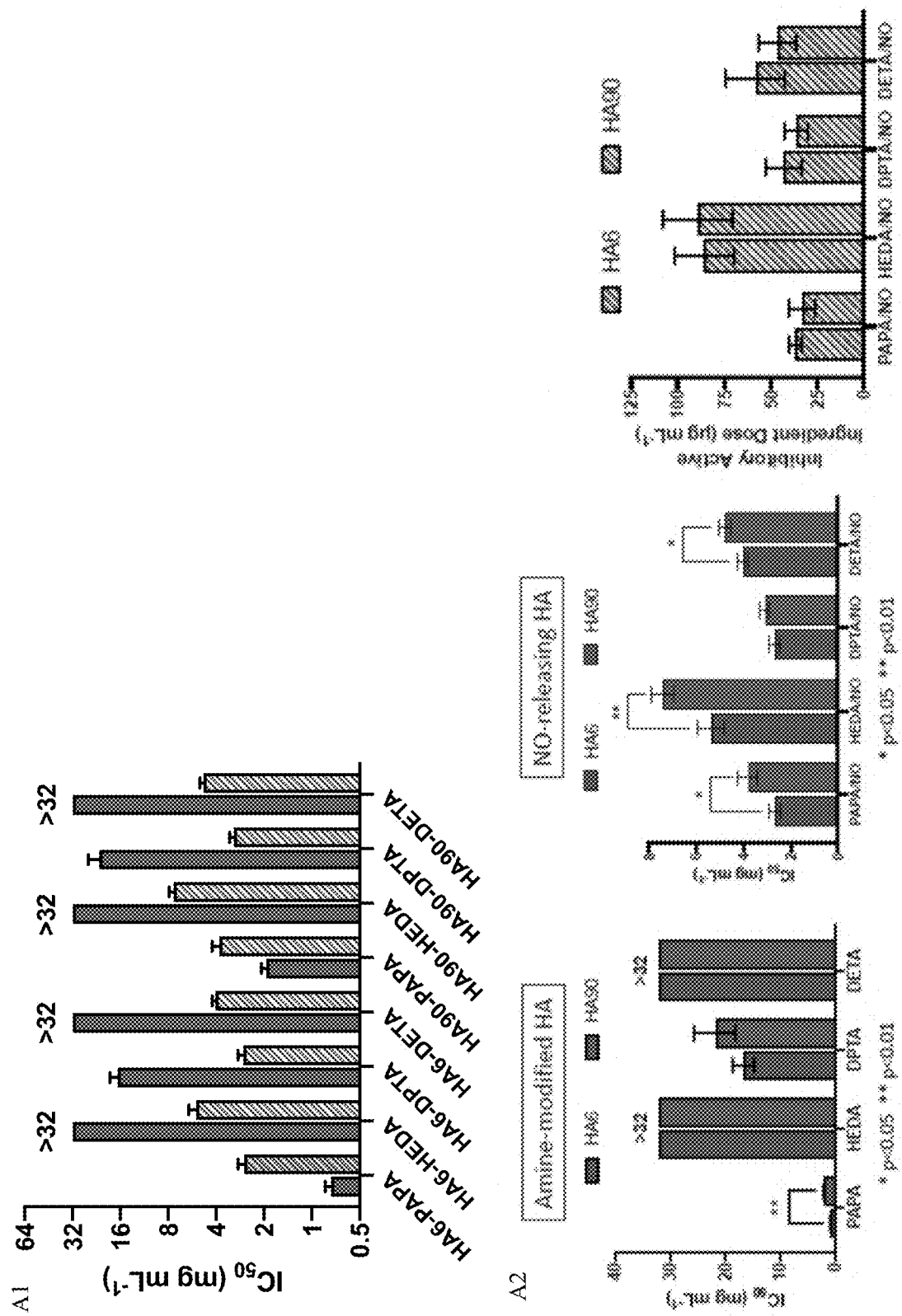
FIG. 12 shows in vitro cytotoxicity results. (A1) shows concentration of amine-modified (solid) and NO-releasing (striped) hyaluronic acid derivatives required to reduce enzymatic activity of L929 murine fibroblasts by 50% ($IC_{50}$). (A2) similarly shows concentration of amine-modified and NO-releasing hyaluronic acid derivatives required to reduce enzymatic activity of L929 murine fibroblasts by 50% ($IC_{50}$), as well as the inhibitory active ingredient dose of the NO-releasing hyaluronic acid.
Figure 12:
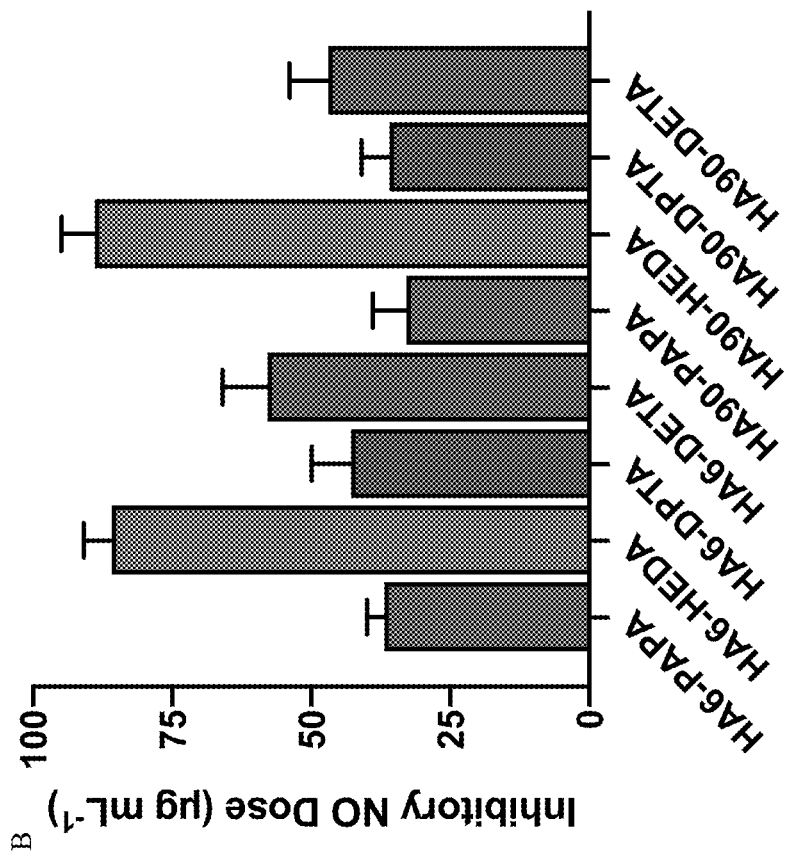
Figure 13:
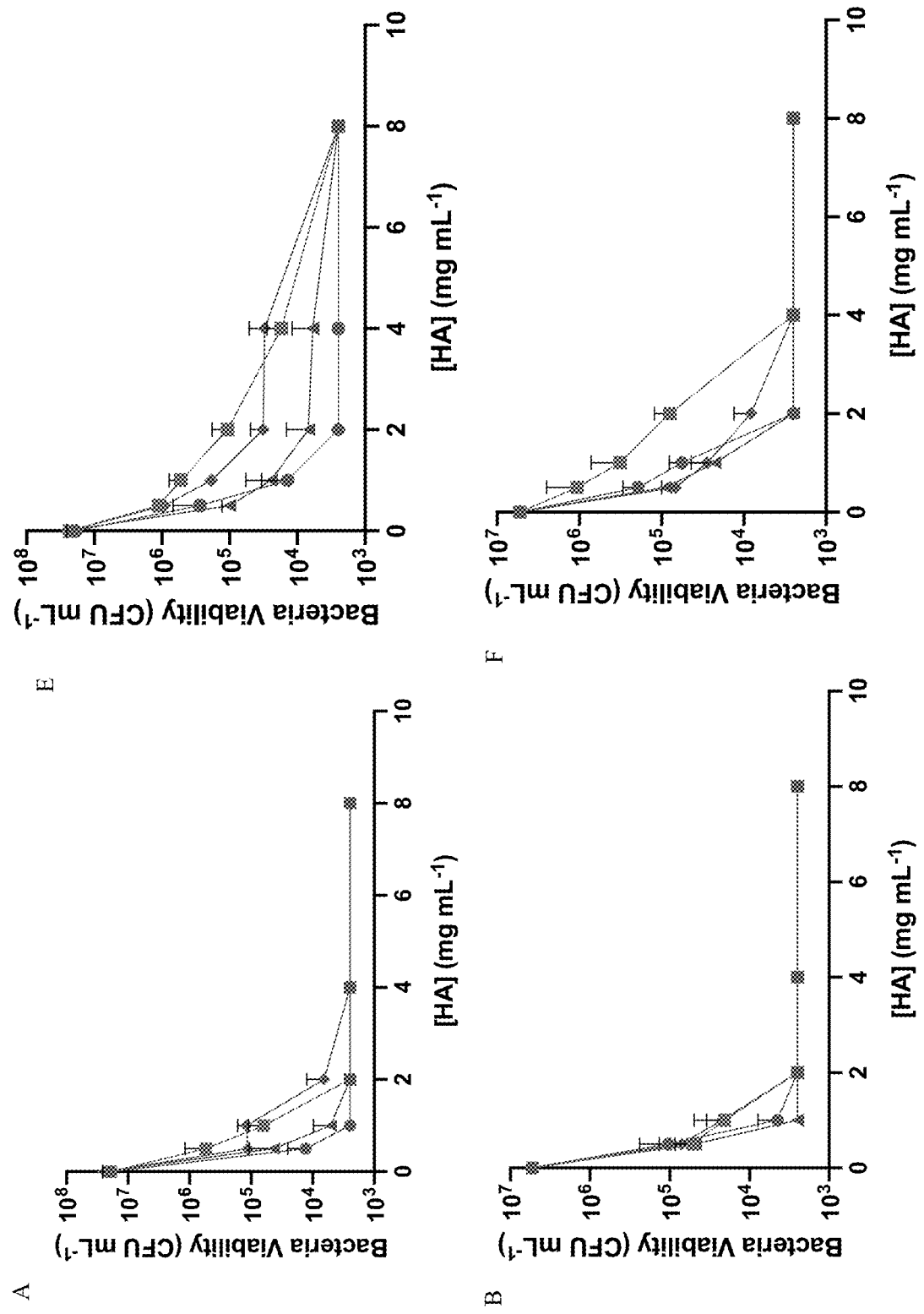
FIG. 13 shows antibacterial efficacy of 6 and 90 kDa NO-releasing hyaluronic acid derivatives against E. coli, P. aeruginosa, S. aureus, and faecalis. Antibacterial efficacy of (A-D) 6 kDa and (E-H) 90 kDa NO-releasing hyaluronic acid against (A, E) E. coli, (B, F) P. aeruginosa, (C) S. aureus, and (D) E. faecalis is shown. Modifications include PAPA (blue circle), HEDA (green square), DPTA (red triangle), and DETA (purple diamond).
Figure 13:
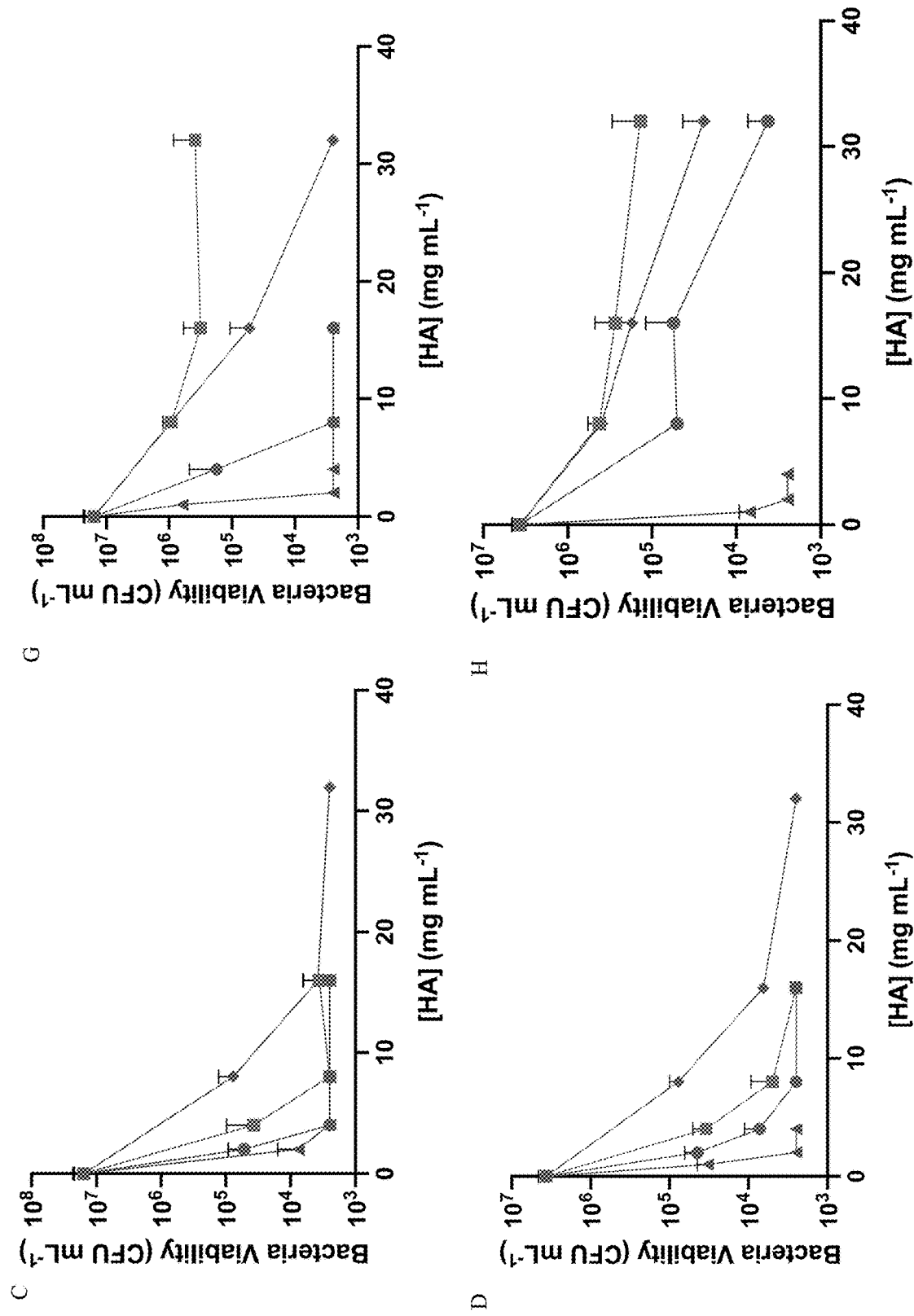
Figure 14:
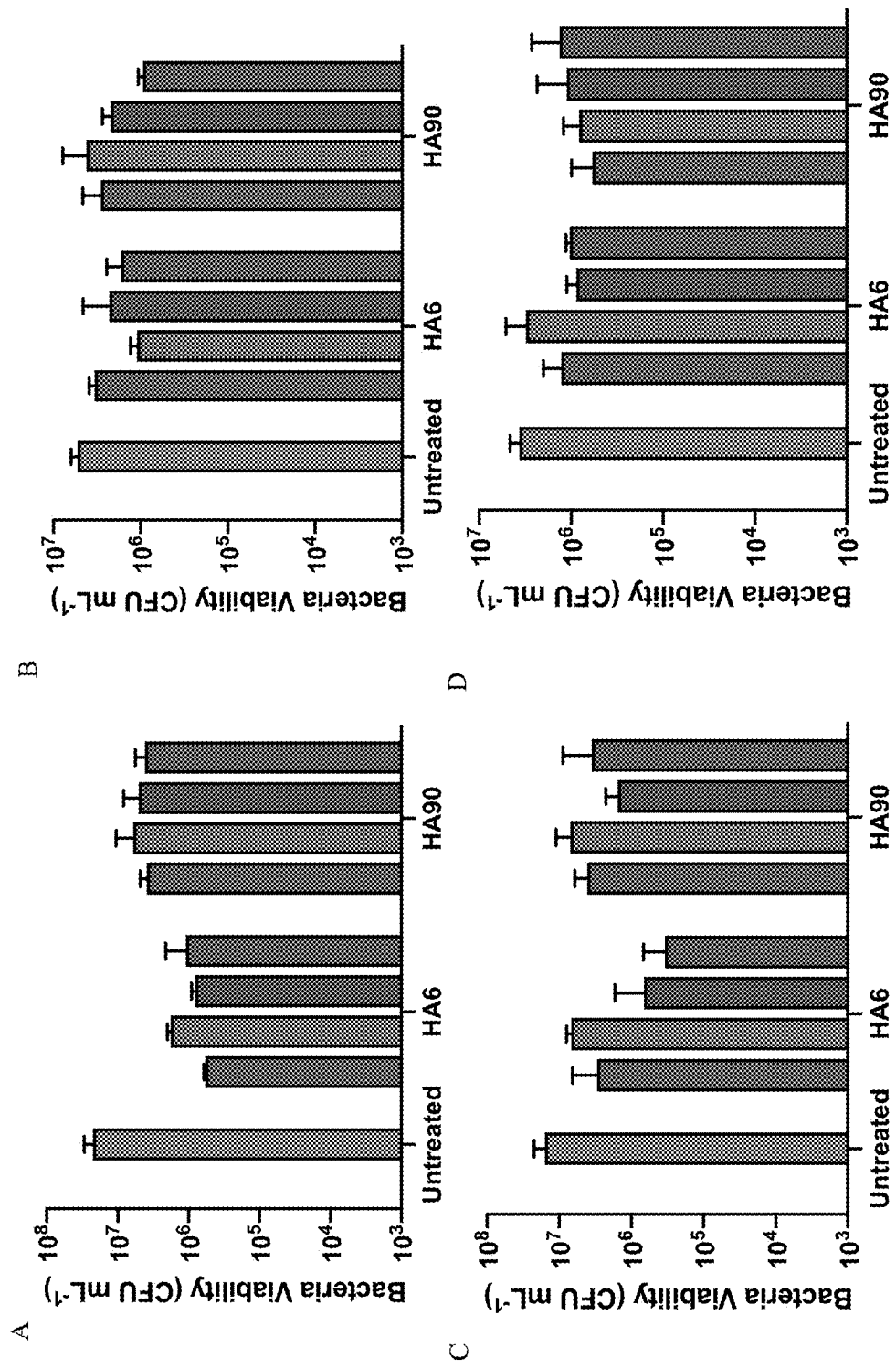
FIG. 14 shows colonies remaining following treatment of E. coli, P. aeruginosa, S. aureus, and E. faecalis with 6 and 90 kDa amine-functionalized (control) hyaluronic acid. Colonies of (A) E. coli, (B) P. aeruginosa, (C) S. aureus, and (D) E. faecalis remaining after 4 h treatment with 6 kDa and 90 kDa amine-modified hyaluronic acid (without NO). Modifications include PAPA (blue), HEDA (green), DPTA (red), and DETA (purple). All modifications were evaluated at 8 mg mL$^{-1}$ for (A) E. coli and (B) P. aeruginosa. Modifications were evaluated at 16 mg mL$^{-1}$ for (C) S. aureus and (D) E. faecalis unless higher doses were necessary for eradication with the NO-releasing derivative. For both S. aureus and E. faecalis, HA6-DETA, HA90-HEDA, and HA90-DETA were evaluated at 32 mg mL$^{-1}$. For E. faecalis, HA90-PAPA was also evaluated at 32 mg mL$^{-1}$. Of note, none of the amine-modified HA derivatives were bactericidal (≥3-log reduction) at the evaluated concentrations.
Figure 15:
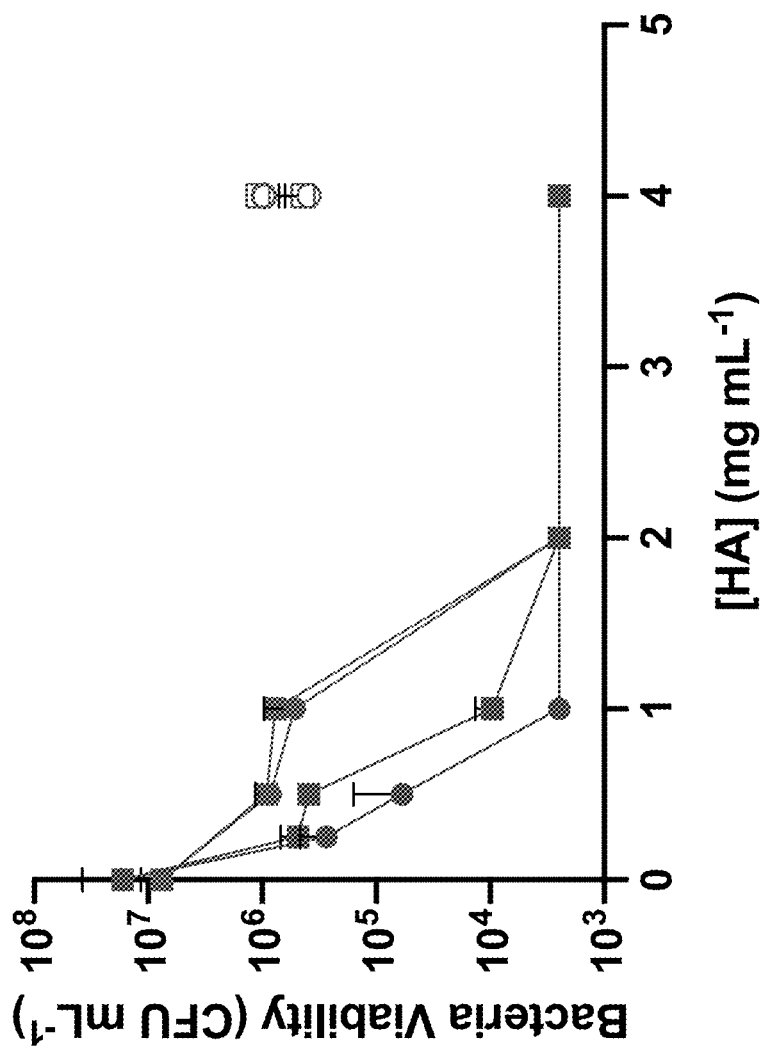
FIG. 15 shows bacteria killing curves for 6 and 90 kDa DPTA-functionalized and NO-releasing hyaluronic acid against MDR-P. aeruginosa and MRSA. Antibacterial efficacy of 6 kDa (circle) and 90 kDa (square) DPTA-modified (hollow) and NO-releasing (solid) hyaluronic acid against antibiotic-resistant bacteria strains, including multidrug-resistant P. aeruginosa (red) and methicillin-resistant S. aureus (blue) is shown.
Figure 18:
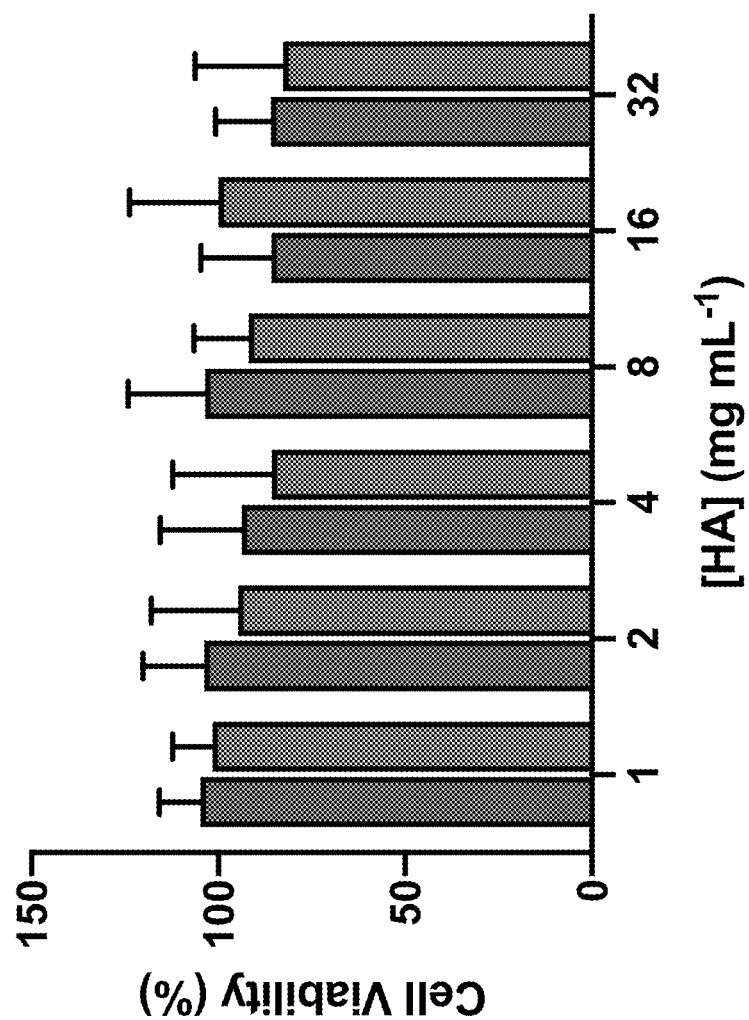
FIG. 18 shows viability of L929 murine fibroblasts following 24 h treatment with unmodified 6 kDa (blue, left) and 90 kDa (green, right) hyaluronic acid.
Figure 19:
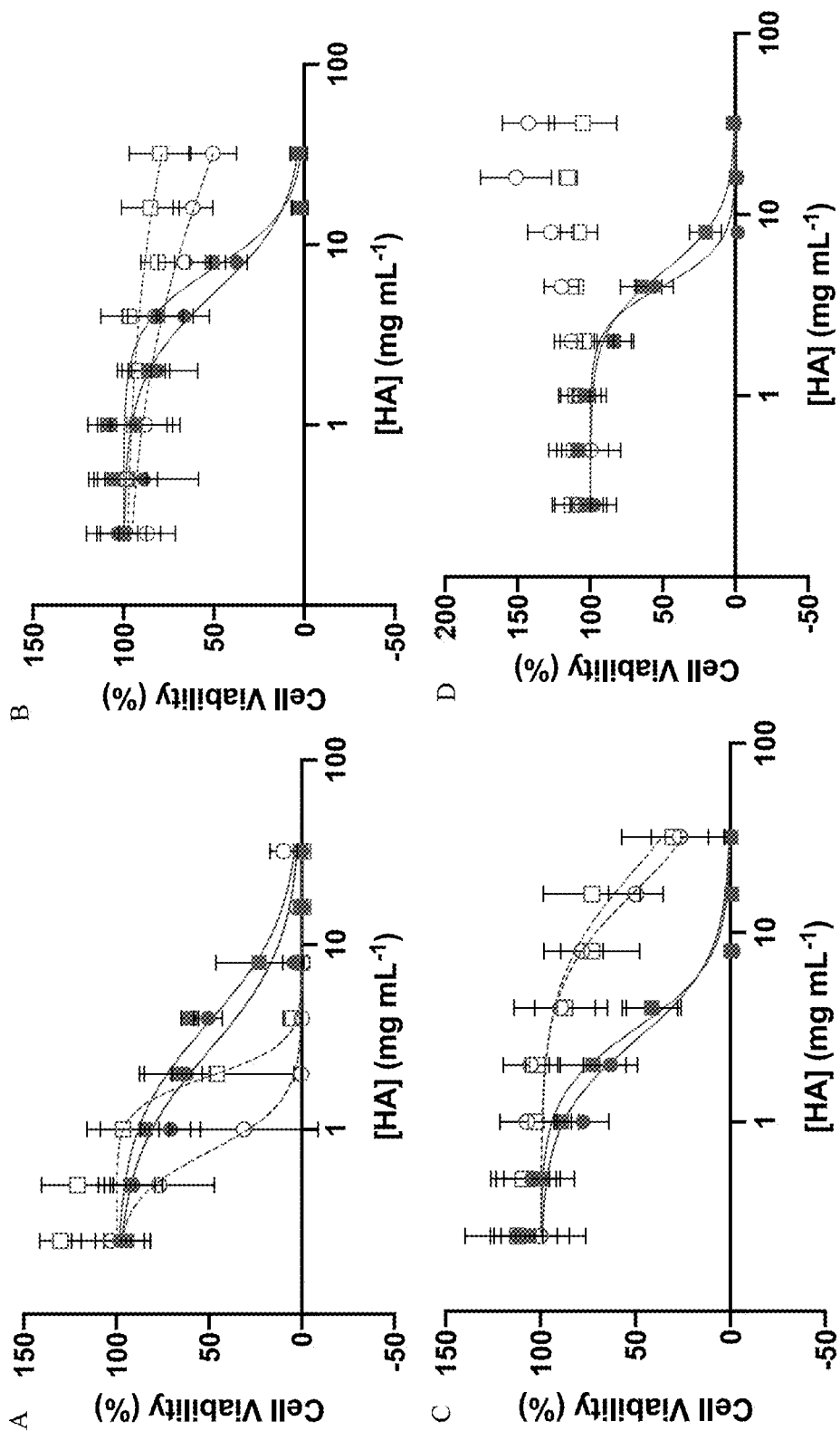
FIG. 19 shows dose-response curves after 24 h treatment of L929 murine fibroblasts with amine-modified (hollow) and NO-releasing (solid) HA derivatives. Modifications of 6 kDa (red circle) and 90 kDa (blue square) HA include (A) PAPA, (B) HEDA, (C) DPTA, and (D) DETA.

Dose-response curves were plotted using GraphPad Prism 8 software (San Diego, CA). Non-linear regression (normalized response with variable slope) analysis was performed to determine the IC$_{50}$ values. The IC$_{50}$ results and the L929 murine fibroblast viability results following treatment with unmodified, amine-modified, and NO-releasing HA are set forth in FIGS. 12, 18, and 19. Cytotoxicity is highly influenced by NO payload, NO-releasing HEDA-modified HA is least toxic to cells. All data presented are from n≥3 separate experiments.

Example 3B—Carboxymethylcellulose Scaffolds

The following examples pertain to the use of NO-releasing carboxymethylcellulose (CMC). The scaffolds generated in Example 2 are used in the following experiments against various bacterial cultures:

Determination of 2 h minimum bactericidal concentrations (MBC$_{2h}$). *P. gingivalis* was reinoculated overnight from a frozen stock in W—C anaerobic broth in an anaerobic chamber (Coy Laboratory Products, Grass Lake, MI). A 300 μL aliquot of bacteria was transferred into fresh broth and grown to 10$^8$ cfu/mL. *A. actinomycetemcomitans* was prepared similarly using brain heart infusion (BHI) broth under microaerophilic conditions using a GasPak EZ campy container system. Bacterial concentrations were confirmed by measuring optical density at 600 nm ($OD_{600}$). Bacteria were diluted to $10^6$ cfu/mL in 1% broth-supplemented PBS 7.4 and exposed to control (i.e., non-NO-releasing) and NO-releasing materials under aerobic conditions for 2 h at 37° C. Bacteriostatic conditions were confirmed for both bacteria when exposed to no material. After the exposure, samples were diluted 10-1000× in PBS 7.4 and plated on their corresponding agar using an IUL Instruments Eddy Jet 2 spiral plater (Neutec Group, Farmingdale, NY). *P. gingivalis* on CDC anaerobe 5 vol % sheep blood agar were incubated in the anaerobic chamber for 3 d and *A. actinomycetemcomitans* on brain heart infusion agar (BHA) were incubated for 3 d under microaerophilic conditions. After incubation, bacterial concentrations were determined using the plate counting method with an IUL Instruments Flash & Go (Neutec Group, Farmingdale, NY).

The antibacterial efficacy of NO-releasing CMC-amines was evaluated against planktonic forms of two prominent periodontopathogens, *P. gingivalis* and *A. actinomycetemcomitans*. Both of these Gram-negative bacteria play essential roles in the propagation of periodontal diseases, with *P. gingivalis* acting as a keystone pathogen in the development of chronic periodontitis and *A. actinomycetemcomitans* instigating more localized, aggressive forms of periodontitis. Antibacterial efficacy, presented in Table 11, was evaluated by determining the minimum bactericidal concentrations (i.e., a 3-log reduction in bacterial viability) for each polymer over a 2 h exposure under static conditions ($MBC_{2h}$).

With the exception of CMC-DETA/NO, the NO-releasing scaffolds possessed similar killing efficacy against both pathogens. Notably, the control (i.e., non-NO-releasing) scaffolds demonstrated minimal bactericidal action, supporting that NO is indeed acting as the bactericidal agent. The slower NO-release half-life of CMC-DETA/NO resulted in lower NO totals at 2 h, the length of the exposure, thus requiring higher scaffold concentrations to elicit bactericidal activity. While both of the periodontopathogens of interest are Gram-negative, the A7436 strain of *P. gingivalis* possesses a capsule which may reduce NO penetration relative to *A. actinomycetemcomitans*, resulting in slightly higher $MBC_{2h}$ for three of the tested polymers.

TABLE 11

Antibacterial efficacy of NO-releasing CMC against prominent periodontopathogens

| | *P. gingivalis* | | *A. actinomycetemcomitans* | |
|---|---|---|---|---|
| Sample | $MBC_{2h}$ (mg mL$^{-1}$) | 2 h NO dose (μmol mL$^{-1}$) | $MBC_{2h}$ (mg mL$^{-1}$) | 2 h NO dose (μmol mL$^{-1}$) |
| CMC-DETA | >16 | — | >16 | — |
| CMC-DETA/NO | 16 | 1.96 | 4 | 0.49 |
| CMC-DPTA | >16 | — | >16 | — |
| CMC-DPTA/NO | 4 | 1.00 | 2 | 0.50 |
| CMC-HEDA | >16 | — | >16 | — |
| CMC-HEDA/NO | 4 | 1.68 | 2 | 0.84 |
| CMC-PAPA | >16 | — | >16 | — |
| CMC-PAPA/NO | 2 | 0.75 | 2 | 0.75 |

Cytotoxicity of modified CMCs against human gingival fibroblasts. HGF-1 cells were cultured in FibroLife S2 media supplemented with 1% penicillin and streptomycin and incubated at 37° C. in humidified 5 vol % $CO_2$. Upon reaching ~80% confluency, cells were trypsinized and placed into tissue-culture treated 96-well polystyrene plates at a density of $10^4$ cells/well. After 24 h of incubation in 96-well plates, media was aspirated and replaced with 100 μL media containing control and NO-releasing CMC. After 24 h exposure at 37° C., media from each well was aspirated, cells were washed with PBS, and 100 μL MTS solution (composed of media/MTS/PMS at 105/20/1 v/v/v) was added. Plates were incubated for 2 h before absorbance of the media in each well was measured at 490 nm with a SpectraMax M2 UV-vis spectrophotometer (Molecular Devices, San Jose, CA). Relative cell viability was determined using a control (untreated cells) and blank (MTS solution) by using the equation:

$$\% \text{ cell viability} = \frac{Abs_{490} - Abs_{blank}}{Abs_{control} - Abs_{blank}} * 100\%$$

Figure 20:
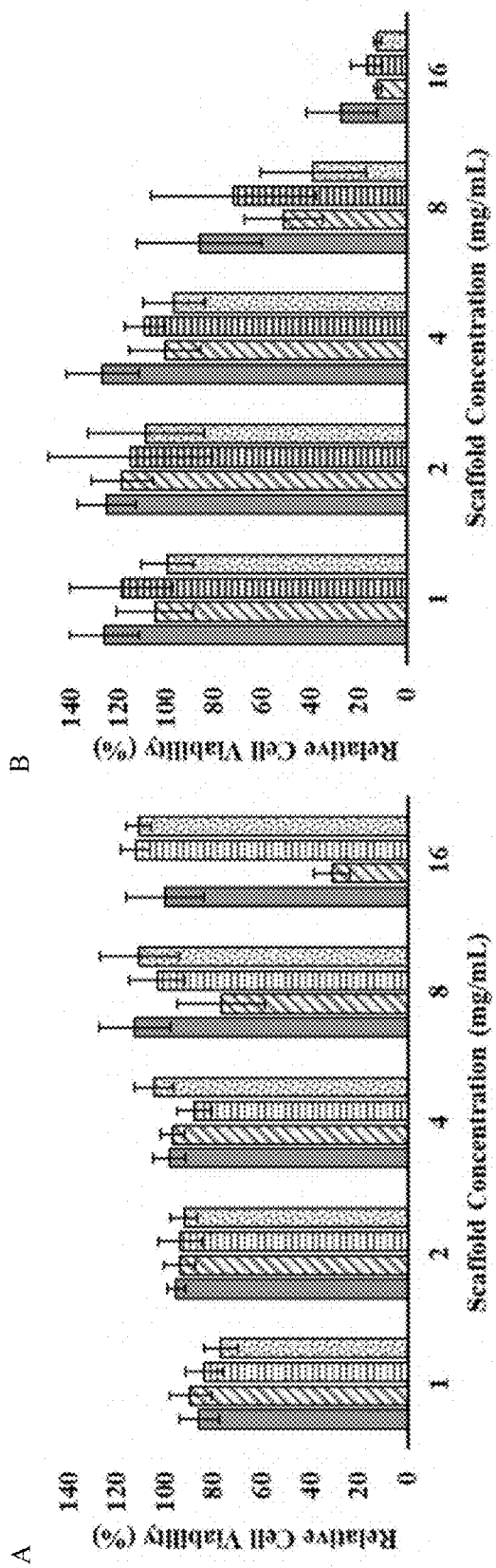
FIG. 20 shows metabolic activity of HGF-1 cells determined via MTS assay after 24 h exposure to (A) CMC-DETA (solid), CMC-DPTA (diagonal stripes), CMC-HEDA (horizontal stripes), and CMC-PAPA (dotted) and (B) CMC-DETA/NO (solid), CMC-DPTA/NO (diagonal stripes), CMC-HEDA/NO (horizontal stripes), and CMC-PAPA/NO (dotted).

Toxicities of the CMC scaffolds against mammalian cells were evaluated by exposing human gingival fibroblasts (HGF) to both NO-releasing and non-NO-releasing materials for 24 h in FIG. 20. Metabolic activity was determined at the endpoint using an MTS assay and correlated to cell viability, with untreated cells representing 100% viability. For the amine-modified CMCs, only CMC-DPTA resulted in significant decreases in HGF viability, decreasing to ~80% at 8 mg/mL and ~30% at 16 mg/mL. More significant differences were observed for the NO-releasing CMC polymers. Up to 4 mg/mL, CMC-DETA/NO resulted in consistently higher apparent cell viabilities than baseline, either as a result of proliferative effects of NO or increased cell metabolism. Above 4 mg/mL, cell viability decreased for all materials, likely in response to the increasing NO doses exerting oxidative and nitrosative stress on the fibroblasts. Notably, high cell viability is maintained for 24 h at the $MBC_{2h}$ of all scaffolds with the exception of CMC-DETA/NO.

This demonstrates the potency of NO-releasing carboxymethylcellulose as an antibacterial agent against two prominent periodontopathogens, *P. gingivalis* and *A. actinomycetemcomitans*. In vitro results showed that faster NO-release kinetics resulted in lower $MBC_{2h}$, enabling all scaffolds other than CMC-DETA/NO to achieve 3-log reduction in bacteria at concentrations that were not significantly cytotoxic to HGF-1 cells.

Example 4

Prophetic Example

A solution of CMC-DETA as disclosed in Example 2 is prepared at a concentration of 10 mg/ml in PBS. The solution is injected via a syringe into an open laceration from a knife wound of an adult male patient. Upon reaching the internal surfaces of the wound, the viscous solution forms a firm gel. The gel is covered with a bandage. As a control, another patient with a similar wound is treated by flushing the wound, application of bacitracin application and covering it with a bandage. The experimental and control antibacterial formulations are reapplied and the new bandages are applied daily.

After three days, the experimental patient shows no sign of infection. The control patient has redness around the wound, indicative of bacterial invasion.

After one week, the experimental patient's wound is healed and all that is left is a scar. The control patient's wound heals after a period of 17 days.

Example 4

Prophetic Example

A solution of HA6-DPTA/NO as disclosed in Example 1 is prepared at a concentration of 5 mg/ml in PBS. A solution of CMC-DETA as disclosed in Example 2 is prepared at a concentration of 10 mg/ml in PBS. The two solutions are mixed and form a firm gel. This gel is applied to a diabetic foot sore that is infected with MRSA and that has previously been treated with antibiotics. The gel is covered with a bandage. The gel is reapplied along with a fresh bandage daily.

After six days, the patient shows no sign of infection. After three weeks, the patient's wound is healed.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering an NO-donating composition" include "instructing the administration of an NO-donating composition." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 one millipascal-second" includes "10 one millipascal-second."

What is claimed is:

1. An NO releasing carboxymethylcellulose-derived polymer compound, comprising a unit structure of Formula I:

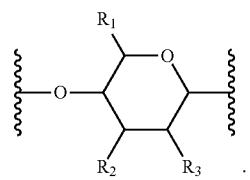

Formula I wherein, $R_1$ is $-CH_2-O-CH_2C(O)-X^1-((CH_2)_gX^2)_h((CH_2)_jX^3)_k-(CH_2)_iH$;

$R_2$ and $R_3$ are independently selected from the group consisting of $-OH$, $-CH_2OH$, $-OCH_2C(O)OH$, $-CH_2OCH_2C(O)OH$, $-C(O)-O-((CH_2)_aO)_b-H$, $-C(O)-O-((CH_2)_aO)_b-(CH_2)_cH$, $-C(O)-O-(C_{1-5}alkyl)$, $-C(O)-NH-((CH_2)_dNH)_e-H$, $-C(O)-NH-((CH_2)_dNH)_e-(CH_2)_fH$, $-CH_2C(O)-NH-((CH_2)_dNH)_e-H$, $-CH_2C(O)-NH-((CH_2)_dNH)_e-(CH_2)_fH$, $-C(O)-X^1-((CH_2)_gX^2)_h-(CH_2)_iH$, $-CH_2C(O)-X^1-((CH_2)_gX^2)_h-(CH_2)_iH$, $-C(O)-X^1-((CH_2)_gX^2)_h((CH_2)_jX^3)_k-(CH_2)_iH$, $-O-((CH_2)_aO)_b-H$, $-O-((CH_2)_aO)_b-(CH_2)_cH$, $-O-(C_{1-5}alkyl)$, $-NH-((CH_2)_dNH)_e-H$, $-NH-((CH_2)_dNH)_e-(CH_2)_fH$, $-X^1-((CH_2)_gX^2)_h-(CH_2)_iH$, $-X^1-((CH_2)_gX^2)_h((CH_2)_jX^3)_k-(CH_2)_iH$, and $-CH_2C(O)-X^1-((CH_2)_gX^2)_h((CH_2)_jX^3)_k-(CH_2)_iH$;

each instance of a, b, c, d, e, f, g, i, j, and k, is independently 0, 1, 2, 3, 4, 5, 6, 7, 8, 9, or 10;

h and l are in each instance independently 1, 2, 3, 4, 5, 6, 7, 8, 9, or 10;

each instance of $X^1$, $X^2$, and $X^3$ is independently selected from the group consisting of $-O-$, $-S-$, $-NH-$, $C(O)$ $NH-$, and a nitric oxide donating moiety;

wherein at least one of $X^1$, $X^2$, and $X^3$ in said NO releasing carboxymethylcellulose-derived polymer compound is present as said nitric oxide donating moiety represented by one of the following:

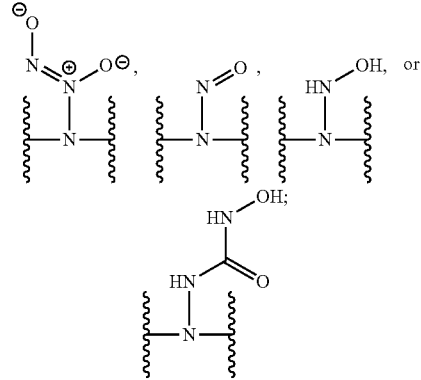

and wherein the compound has a viscosity of equal to or at least about 10 mPa·s at 20° C. at a concentration of 5% w/w in water.

2. The compound of claim 1, wherein Formula I has the stereochemical configuration shown in Formula I':

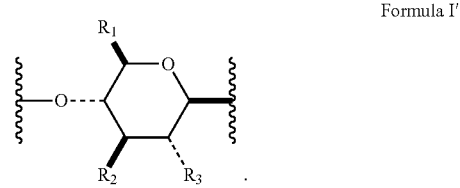

Formula I'

3. The compound of claim 1, wherein at least one of $X^1$, $X^2$, and $X^3$ is represented by the following:

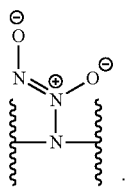

4. The compound of claim 1, wherein $R_1$ is —$CH_2$—O—$CH_2C(O)$—NH—$((CH_2)_gX^2)_h$ $((CH_2)_jX^3)_k$—$(CH_2)_lH$, and at least one of $X^2$ and $X^3$ is present as

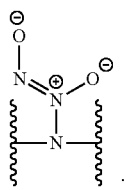 [SMILES: *N(*)/[N+]([O-])=N/[O-]]

5. The compound of claim 1, wherein $R_2$ and $R_3$ are —OH.

6. The compound of claim 1, wherein $R_1$ is

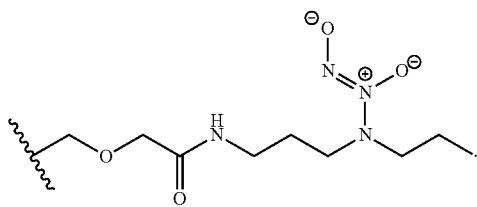

7. The compound of claim 1, wherein the compound has a viscosity of equal to or at least about 20 mPa·s at 20° C. at a concentration of 20% w/w in water.

8. The compound of claim 1, wherein the compound is soluble in water at a concentration of 50 mg/ml.

9. The compound of claim 1, wherein the compound has a total releasable NO storage in a range of 0.1-1.0 µmol of NO per mg of compound.

10. The compound of claim 1, wherein the compound has a NO half-life in the range of 0.1-24 hours.

11. The compound of claim 9, wherein the compound has a total duration of NO release in the range of 1-60 hours.

12. The compound of claim 9, wherein the total NO release after 4 hours is in the range between 0.1-1.0 µmol of NO per mg of compound.

13. The compound of claim 1, wherein more than 15% of the repeat units in the compound are monomers of Formula I.

14. The compound of claim 1, wherein the compound has a molecular weight in the range of about 90 kDa and about 700 kDa.

15. The compound of claim 1, wherein the compound comprises two or more different covalently modified monomers of Formula I.

16. A method of reducing or preventing microbial load on a surface comprising: applying the compound of claim 1 to a surface contaminated with microbes, wherein the microbes are selected from the group consisting of gram-positive bacteria, gram-negative bacteria, fungi, yeast, and viruses.

17. The method of claim 16, wherein the surface is contaminated with two or more of the microbes.

18. The method of claim 16, wherein the surface is an organic surface.

19. The method of claim 16, wherein the surface is human skin.

20. The method of claim 16, wherein the surface is an inorganic surface.

* * * * *